US008822548B2

(12) United States Patent
Olsson et al.

(10) Patent No.: US 8,822,548 B2
(45) Date of Patent: Sep. 2, 2014

(54) COMPOUNDS WITH ACTIVITY AT ESTROGEN RECEPTORS

(75) Inventors: Roger Olsson, Bunkeflo Strand (SE); Lene Hyldtoft, Lyngby (DK); Fabrice Piu, San Diego, CA (US); Magnus Gustafsson, Frederiksberg (DK); Vladimir Sherbukhin, Bronshoj (DK); Birgitte Winther Lund, Bagsvaerd (DK)

(73) Assignee: Acadia Pharmaceuticals Inc., San Diego, CA (US)

( * ) Notice: Subject to any disclaimer, the term of this patent is extended or adjusted under 35 U.S.C. 154(b) by 820 days.

(21) Appl. No.: 12/915,354

(22) Filed: Oct. 29, 2010

(65) Prior Publication Data

US 2011/0046237 A1 Feb. 24, 2011

Related U.S. Application Data

(60) Division of application No. 11/269,913, filed on Nov. 8, 2005, now Pat. No. 7,825,265, which is a continuation-in-part of application No. 11/120,397, filed on May 3, 2005, now abandoned.

(60) Provisional application No. 60/658,332, filed on May 4, 2004.

(51) Int. Cl.
| A61K 31/055 | (2006.01) |
| A61K 31/05 | (2006.01) |
| C07C 37/055 | (2006.01) |
| C07C 37/62 | (2006.01) |
| C07D 263/32 | (2006.01) |
| C07C 39/42 | (2006.01) |

(52) U.S. Cl.
CPC ............... *C07C 37/055* (2013.01); *C07C 37/62* (2013.01); *C07D 263/32* (2013.01); *C07C 39/42* (2013.01)
USPC ........................................................ 514/729

(58) Field of Classification Search
CPC ...... C07C 25/24; C07C 37/055; C07C 37/62; C07C 39/42; C07D 263/32
USPC ................................................. 514/719, 729
See application file for complete search history.

(56) References Cited

U.S. PATENT DOCUMENTS

| 2,342,294 | A | 2/1944 | Niederl et al. |
| 3,517,071 | A | 6/1970 | Caldwell et al. |
| 3,829,462 | A | 8/1974 | Krimm et al. |
| 3,872,105 | A | 3/1975 | Grisar et al. |
| 4,082,913 | A | 4/1978 | Suzuki et al. |
| 4,201,878 | A | 5/1980 | Mark et al. |
| 4,247,484 | A | 1/1981 | Mark et al. |
| 4,554,309 | A | 11/1985 | Mark et al. |
| 5,283,374 | A | 2/1994 | Jeffries, III |
| 5,691,351 | A | 11/1997 | Kolasa et al. |
| 5,707,798 | A | 1/1998 | Brann |
| 6,043,279 | A | 3/2000 | Boehm et al. |
| 6,150,362 | A | 11/2000 | Henkin et al. |
| 6,255,439 | B1 | 7/2001 | Avadhani et al. |
| 6,265,402 | B1 | 7/2001 | Ina et al. |
| 6,518,306 | B1 | 2/2003 | Christensen, IV |
| 6,586,431 | B1 | 7/2003 | Liras et al. |
| 2005/0256210 | A1 | 11/2005 | Olsson et al. |
| 2006/0122278 | A1 | 6/2006 | Olsson et al. |

FOREIGN PATENT DOCUMENTS

| BE | 627224 A | 7/1963 |
| EP | 0995737 A1 | 4/2000 |
| GB | 1410275 A | 10/1975 |
| JP | 2000072695 A | 3/2000 |
| WO | 0010958 A1 | 3/2000 |
| WO | 0039091 A1 | 7/2000 |
| WO | 0110385 A2 | 2/2001 |
| WO | 0218334 A2 | 3/2002 |
| WO | 2004048309 A1 | 6/2004 |
| WO | 2005037755 A2 | 4/2005 |

OTHER PUBLICATIONS

Glossary of medical education terms, Institute of International Medical Education. http://www.iime.org/glossary.htm Accessed in Mar. 2013.*
Pavelka K. Symptomatic treatment of osteoarthritis: paracetamol or NSAIDs? Int J Clin Pract Suppl 144:5-12, 2004.*
Forinash et al. New hormonal contraceptives: a comprehensive review of the literature. Pharmacotherapy 23:1573-1591, 2003.*
McDonnell et al. Definition of the Molecular and Cellular Mechanisms Underlying the Tissue-selective Agonist/Antagonist Activities of Selective Estrogen Receptor Modulators. Recent Prog Horm Res 57:295-316, 2002.*
Aeberli et al., Synthesis and antiinflammatory acitivity of 2-aryl-2-alpha-piperidyl-1,3-dioxanes. J Med Chem. Jan. 1969;12(1):51-54.
Behl, Estrogen can protect neurons: modes of action. J Steroid Biochem Mol Biol Dec. 2003;83(1-5):195-197.
Coleman et al., QSAR Models of the in vitro Strogen Activity of Bisphenol A Analogs. QSAR Comb Sci.,2003;22:78-88.
Non-Final Office Action issued by the United States Patent and Trademark Office in U.S. Appl. No. 11/120,397 dated Oct. 29, 2007.
Non-Final Office Action issued by the United States Patent and Trademark Office in U.S. Appl. No. 11/269,913 dated Oct. 29, 2007.
Couse and Korach, Estrogen Receptor Null Mice: What Have We Learned and Where Will They Lead Us? Endocr Rev. Jun. 1999;20(3):358-417.
Database Beilstein, Accession Nos. 3156998, 3519057, 3156998, and 3519057, Accessed in 2010.
Database Beilstein, Accession Nos. 8372608, 9453634, 9455728, 8372608, and 9455728, Accessed in 2010.

(Continued)

*Primary Examiner* — Brandon Fetterolf
*Assistant Examiner* — Yih-Horng Shiao
(74) *Attorney, Agent, or Firm* — Sam K. Tahmassebi; TechLaw LLP

(57) ABSTRACT

Disclosed herein are methods of treatment and prevention of diseases and disorders related to estrogen receptors comprising administering novel di-aromatic compounds to patients in need thereof.

21 Claims, 4 Drawing Sheets

(56) References Cited

OTHER PUBLICATIONS

Erlandsson et al., Role of oestrogen receptors alpha and beta in immune organ development and in oestrogen-mediated effects on thymus. Immunology. May 2001;103(1):17-25.

Evans, The Steroid and Thyroid Hormone Receptor Superfamily. Science May 13, 1998;240(4854):889-895.

Gallegos Saliner et al., Molecular Quantum Similarity Analysis of Estrogenic Activity. J Chem Inf Comput Sci. Jul.-Aug. 2003;43(4):1166-1176.

Green et al., Human oestrogen receptor cDNA: sequence, expression and homology to v-erb-A. Nature Mar. 13-19, 1986;320(6058):134-139.

Greene et al., Sequence and Expression of Human Estrogen Receptor Complementary DNA. Science Mar. 1986 7;231(4742):1150-1154.

Grisar et al., Hypolipidemic Substituted 1,3-Benzodioxole-2-carboxylates. J Med Chem. Jul. 1974;17(7):721-725.

Harris et al., Characterization of the Biological Roles of the Estrogen Receptors, ERalpha and ERbeta, in Estrogen Target Tissues in Vivo Through the Use of an ERalpha-Selective Ligand. Endocrinology Nov. 2002;143(11):4172-4177.

Harris et al., Evaluation of an Estrogen Receptor-Beta Agonist in Animal Models of Human Disease. Endocrinology. Oct. 2003;144(10):4241-4249.

Hewitt, Estrogen receptor transcription and transactivation: Estrogen receptor knockout mice: what their phenotypes reveal about mechanisms of estrogen action. Breast Cancer Res 2000;2(5):345-352.

Koehler et al., Reflections on the Discovery and Significance of Estrogen Receptor Beta. Endocr Rev. May 2005;26 (3):465-478.

Kuiper and Gustafsson, The novel estrogen receptor-beta subtype: potential role in the cell- and promoter-specific actions of estrogens and anti-estrogens. FEBS Lett, Jun. 23, 1997;410(1):87-90.

Kuiper, Cloning of a novel receptor expressed in rat prostate and ovary. Proc Natl Acad Sci USA. Jun. 11, 1996;93(12):5925-5930.

Lindberg et al., Two Different Pathways for the Maintenance of Trabecular Bone in Adult Male Mice. J Bone Miner Res Apr. 2002;17(4):555-562.

Matthews and Gustafsson, Estrogen Signaling: A Subtle Balance Between ER alpha and ER beta. Mol Interv Aug. 2003;3(5):281-292.

McElvain and Berger, The Condensation of 4-Piperidones and Piperidinols with Phenols. J Amer Chem Soc. 1955;77: 2848-2850.

McMurry and Scott. A Method for the Regiospecific Synthesis of Enol Triflates by Enolate Trapping. Tetrahedron letters, 1983;24(10):979-982.

Muthyala et al., Exploration of the Bicyclo[3.3.1]nonane System as a Template for New Ligands for the Estrogen Receptor. Bioorg Med Chem Lett. Dec. 15, 2003;13(24):4485-4488.

Muthyala et al., Bridged Bicyclic Cores Containing a 1,1-Diarylethylene Motif are High-Affinity Subtype-Selective Ligands for the Estrogen Receptor. J Med Chem. Apr. 24, 2003;46(9):1589-1602.

Niederl et al., Steric Hindrance in Ketone-Phenol Condensations. The Condensation of Guaiacol with Cyclic Ketones. J Am Chem Soc. 1940;62:320-322.

Nilsson and Koehler, Oestrogen Receptors and Selective Oestrogen Receptor Modulators: Molecular and Cellular Pharmacology. Basic Clin Pharmacol Toxicol. Jan. 2005;96(1):15-25.

Osborne and Schiff, Estrogen-Receptor Biology: Continuing Progress and Therapeutic Implications. J Clin Oncol Mar. 10, 2005;23(8):1616-1622.

Osterlund and Hurd, Estrogen receptors in the human forebrain and the relation to neuropsychiatric disorders. Prog Neurobiol Jun. 2001;64(3):251-267.

Ostlund et al., Estrogen Receptor Gene Expression in Relation to Neuropsychiatric Disorders. Ann NY Acad Sci Dec. 2003;1007:54-63.

Patrone et al., Regulation of Postnatal Lung Development and Homeostasis by Estrogen Receptor Beta. Mol Cell Biol Dec. 2003;25(23):8542-8552.

Rodionov et al., High-performance liquid chromatography of 1,1-diarylcycloalkanes. Zhurnal Analiticheskoi Knimii 1987;42(8):1485-1488; ZCAPLUS printout, ISSN: 0044-4502, compound RN:91663-14-8.

Uehara et al., The Effect of a Para Substituent on the Conformational Preference of 2,2-Diphenyl-1,3-dioxanes: Evidence for the Anomeric Effect from X-ray Crystal Structure Analysis(1). J Org Chem. Mar. 5, 1999;64(5):1436-1441.

Wang et al., Estrogen receptor (ER)beta knockout mice reveal a role for ERbeta in migration of cortical neurons in the developing brain. Proc Natl Acad Sci U S A. Jan. 21, 2003;100(2):703-708.

Wang et al., Morphological abnormalities in the brains of estrogen receptor beta knockout mice. Proc Natl Acad Sci U S A. Feb. 27, 2001;98(5):2792-2796.

Windahl et al., Elucidation of estrogen receptor function in bone with the use of mouse models. Trends Endocrinol Metab. Jul. 2002;13(5):195-200.

Wise, Estrogens and neuroprotection. Trends Endocrinol Metab Aug. 2002;13(6):229-230.

Wolff, Burger's Medicinal Chemistry, Fifth Edition, vol. I: Principles and Practice. John Wiley & Sons, 1995: 975-977.

Yamasaki et al., Comparative study of the uterotrophic potency of 14 chemicals in a uterotrophic assay and their receptor-binding affinity. Toxicol Lett. Jan. 15, 2004;146(2):111-120.

Yamasaki et al., Comparison of the reporter gene assay for ER-alpha antagonists with the immature rat uterotrophic assay of 10 chemicals. Toxicol Lett. Apr. 30, 2003;142(1-2):119-131.

Zimmerman et al. Photochemical Migratory Aptitudes in Cyclohexenones. Mechanistic and Exploratory Photochemistry. XXII. J Amer Chem Soc. Apr. 26, 1967;89(9):2033-2047.

* cited by examiner

COMPOUNDS WITH ACTIVITY AT ESTROGEN RECEPTORS

RELATED APPLICATION

This application is a divisional of U.S. application Ser. No. 11/269,913, filed Nov. 8, 2005, entitled "COMPOUNDS WITH ACTIVITY AT ESTROGEN RECEPTORS," which in turn is a continuation-in-part of U.S. application Ser. No. 11/120,397, filed May 3, 2005, entitled "COMPOUNDS WITH ACTIVITY AT ESTROGEN RECEPTORS," which claims priority to U.S. Provisional Application Ser. No. 60/568,332, filed May 4, 2004, entitled "IDENTIFICATION OF COMPOUNDS WITH ACTIVITY ON ESTROGEN RECEPTORS," all of which are incorporated herein by reference in their entirety.

FIELD OF THE INVENTION

This invention relates to the fields of organic chemistry, pharmaceutical chemistry, biochemistry, molecular biology and medicine. In particular it relates to compounds that modulate the activity of the Estrogen receptors, and to the use of the compounds for the treatment and prevention of diseases and disorders related to the Estrogen beta receptor.

DESCRIPTION OF THE RELATED ART

Estrogen receptors (ER) belong to the family of nuclear hormone receptors. Nuclear hormone receptors define a superfamily of ligand activated transcription factors (Evans, 1988, Science 240:889). Members of this family are typically characterized by the presence of conserved modular domains: a zinc finger DNA binding domain (DBD) triggers the interaction of the receptor with specific response elements at the DNA site, a ligand binding domain (LBD) adjacent to the DBD, and two transcriptional activation domains AF-1 and AF-2 ligand-independent and ligand-dependent, respectively (Nilsson, 2002, SERMs: Research and clinical applications, Eds: Humana Press Inc, 3). Upon ligand binding to the receptor, a conformational change occurs within the LBD bringing the AF-2 domain in closer proximity and allowing for the recruitment of co-activators. Co-activators create a physical interaction between the nuclear hormone receptor and components of the transcriptional machinery, establishing transcriptional modulation of target genes.

Two estrogen receptor subtypes have been identified: ER alpha (ERα, NR3A1) (Green, 1986, Nature 320:134; Greene, 1986, Science 231:1150) and ER beta (ERβ, NR3A2) (Kuiper, 1996, PNAS 93:5925). Both receptors bind to the endogenous natural ligand 17β estradiol with comparable high affinity and modulate the transcriptional activity of target genes through classical estrogen response elements (reviewed in Nilsson, 2005, Bas Clin Pharm Tox, 96:15). More recently, it has been demonstrated that estrogen receptors can mediate non classical actions (reviewed in Osborne, 2005, J Clin Oncol 8:1616): (1) non classical transcriptional regulation in which ERs function as co-activators on alternate regulatory DNA sequences, (2) non genomic or membrane-initiated steroid signaling in which ERs evoke rapid cytoplasmic signaling, and (3) crosstalk with Receptor Tyrosine Kinases (RTKs). Interestingly enough, their ligand binding domains (LBD) only share 56% amino acid identity which suggest that they might accommodate different ligands and thus mediate different or even opposite effects (Kuiper, 1997, FEBS Lett, 410:87). Moreover, the distribution pattern of the two receptors is quite different (reviewed in Mathews, 2003, Mol Intery 3:281). Both ERs are widely distributed both peripherally and in the brain, displaying distinct and sometimes overlapping patterns in a variety of tissues. ERα is expressed primarily in the uterus, liver, kidney and heart. On the other hand ERβ is present mainly in the ovary, prostate, lung, gastrointestinal tract, bladder, hematopoietic and central nervous system (CNS). ERβ specific localization in the CNS includes the hippocampus and thalamus (Osterlund, 2001, Prog Neurobiol 64:251; Ostlund, 2003, Ann NY acad Sci 1007:54). ERα and ERβ are co-expressed in the mammary gland, epididymis, thyroid, adrenal, bone and the dorsal root ganglia of the spinal cord and the cerebral cortex of the brain.

The characterization of mice lacking ERα or ERβ has provided insight into the physiology of estrogen receptors (reviewed in Hewitt, 2000, Breast Cancer Res 2:345; Couse, 1999, Endoc Rev 20:358). Both ERα male and female null mice are infertile because of dysfunction in spermatogenesis and ovulation, respectively. In addition, null females display a lack of sexual behavior, increased aggression and infanticide. Null male exhibit normal mounting behavior but a complete lack of intromission and ejaculation. They also show reduced aggression. In contrast, ERβ null female mice are subfertile with reduced littermates. Male counterparts show no apparent defects in their reproductive tract. The neuroendocrine system is significantly altered in ERα null mice in contrast to ERβ null mice which do not show any impairment. Moreover, the knock-out of ERα in mice leads to absence of breast tissue development, lower bone density and impaired glucose tolerance. Knock out studies of ERβ led to controversial results with some studies being unable to see an effect on bone density (Lindberg, 2002, J Bone Min Res 17:555), whereas other reports suggested an increase in trabecular bone volume in females only due to decreased bone resorption (reviewed in Windahl, 2002, Trends Endoc Metab, 13:195). Interestingly enough, morphological alterations in the brains of mice lacking ERβ are evident (Wang, 2001, PNAS 98:2792) associated with impaired neuronal survival (Wang, 2003, PNAS 100:703), and lead to speculate that ERβ could have an important role in protecting from neurodegenerative disorders such as Alzheimer and Parkinson diseases, and potentially from those resulting of trauma and cardiovascular insults. This is further supported by experimental studies indicating a neurotrophic and neuroprotective role for estrogens (reviewed in Wise, 2002, Trends Endocrinol Metab 13:229; Behl, 2003, J Steroid Biochem Mol Biol 83:195).

More recently, the use of a relatively selective ERβ agonist has unraveled a prominent role in inflammation for this subtype (Harris, 2003, Endoc 144:4241). Beneficial effects were seen in animal models of inflammatory bowel disease and adjuvant-induced arthritis. Indeed, ERβ is expressed both in the intestine and in immune cells. Moreover, ERβ null studies have suggested a role in thymus function (Erlandsson, 2001, Immunol 103:17) as well as in pulmonary inflammation (Patrone, 2003, Mol Cell Biol 25:8542). Interestingly though, no effects associated with classical estrogen function was evident through the use of this ERβ agonist (Harris, 2003, Endoc 144:4241). In particular, that ligand was inactive in mammotrophy, bone density and ovulation in vivo assays. This data is to a certain extent in contrast to a variety of studies including human polymorphisms, knock-out animals, tissue distribution, that argue for a role of ERβ in bone and ovulation homeostasis. Other therapeutic roles for selective ERβ agonists have also been proposed including prostate and breast cancer, autoimmune diseases, colon cancer, malignancies of the immune system, neurodegeneration, cardiovascular function, bone function (reviewed in Koehler, 2005, Endocr Reviews, DOI 10.1210).

SUMMARY OF THE DISCLOSURE

One embodiment disclosed herein is a compound of formula (I):

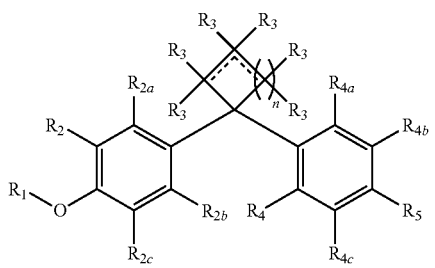

or a pharmaceutically acceptable salt or prodrug thereof, wherein:

n is an integer selected from the group consisting of 3, 4, 5 and 6;

$R_1$ is selected from the group consisting of hydrogen, $C_1$-$C_8$ straight chained or branched alkyl, $C_1$-$C_8$ straight chained or branched alkenyl, cycloalkyl, cycloalkenyl, substituted or unsubstituted heteroaryl, substituted or unsubstituted aryl, substituted or unsubstituted heteroalicyclyl, sulphonyl, $C_1$-$C_8$ straight chained or branched perhaloalkyl, —C(=Z)$R_6$, —C(=Z)O$R_6$, —C(=Z)N($R_6$)$_2$, —S(=O)$_2$N$R_{5a}R_{5b}$, —P(=O)(O$R_6$)$_2$, and —CH$_2$C(=O)$R_5$;

$R_2$, $R_{2a}$, $R_{2b}$, $R_{2c}$ are separately selected from the group consisting of hydrogen, alkyl, alkenyl, cycloalkyl, cycloalkenyl, substituted or unsubstituted aryl, substituted or unsubstituted heteroaryl, substituted or unsubstituted heteroalicyclyl, hydroxy, halogen, sulfonyl, perhaloalkyl, —CN, —O$R_6$, —N$R_6R_{6a}$, —N$R_6$N$R_{6a}R_{6b}$, —N$R_6$N=C$R_{6a}R_{6b}$, —N($R_6$)C($R_{6a}$)=N$R_{6b}$, —C(=Z)$R_6$, —C(=Z)O$R_6$, —C(=Z)N$R_6R_{6a}$, —N($R_6$)—C(=Z)$R_{6a}$, —N($R_6$)—C(=Z)N$R_{6b}R_{6a}$, —OC(=Z)$R_6$, —N($R_6$)—S(=O)$_2$$R_{6a}$, and —S$R_6$;

each $R_3$ is separately selected from the group consisting of hydrogen, alkyl, alkenyl, cycloalkyl, cycloalkenyl, substituted or unsubstituted aryl, substituted or unsubstituted heteroaryl, substituted or unsubstituted heteroalicyclyl, hydroxy, halogen, sulfonyl, perhaloalkyl, —CN, =O, and —O$R_6$, or are separately absent to accommodate a double bond;

two $R_3$ groups are optionally bound together to form a substituted or unsubstituted $C_3$-$C_9$ cycloalkyl or $C_3$-$C_9$ heteroalicyclyl;

$R_{2a}$ is optionally bound to one $R_3$ group to form a substituted or unsubstituted $C_4$-$C_9$ heteroalicyclic, $C_4$-$C_9$ cycloalkyl, or $C_4$-$C_9$ cycloalkenyl;

$R_{4a}$ is optionally bound to one $R_3$ group to form a substituted or unsubstituted $C_4$-$C_9$ heteroalicyclic, $C_4$-$C_9$ cycloalkyl, or $C_4$-$C_9$ cycloalkenyl;

any bond represented by a dashed and solid line represents a bond selected from the group consisting of a single bond and a double bond;

$R_4$, $R_{4a}$, $R_{4b}$, $R_{4c}$ are separately selected from the group consisting of hydrogen, alkyl, alkenyl, cycloalkyl, cycloalkenyl, substituted or unsubstituted aryl, substituted or unsubstituted heteroaryl, substituted or unsubstituted heteroalicyclyl, hydroxy, nitro, halogen, sulfonyl, perhaloalkyl, —O$R_6$, —N$R_6R_{6a}$, —N$R_6$N$R_{6a}R_{6b}$, —N$R_6$N=C$R_{6a}R_{6b}$, —N($R_6$)C($R_{6a}$)=N$R_{6b}$, —CN, —C(=Z)$R_6$, —C(=Z)O$R_6$, —C(=Z)N$R_6R_{6a}$, —S(=Z)N$R_6R_{6a}$, —N($R_6$)—C(=Z)$R_{6a}$, —N($R_6$)—C(=Z)N$R_{6b}R_{6a}$, —OC(=Z)$R_6$, —N($R_6$)—S(=O)$_2$$R_{6a}$, and —S$R_6$;

$R_{4a}$ and $R_{4b}$ are optionally bound together to form an aryl, heteroaryl, or heteroalicyclyl;

$R_5$ is selected from the group consisting of hydrogen, alkyl, alkenyl, cycloalkyl, cycloalkenyl, halogen, —CN, —S$R_6$, sulfonyl, —C(=O)N$R_6R_{6a}$, —C(=O)$R_6$, —N$R_6R_{6a}$, —COO$R_6$, and perhaloalkyl;

Z is oxygen or sulfur; and $R_6$, $R_{6a}$ and $R_{6b}$ are separately selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, and substituted or unsubstituted heteroalicyclyl;

provided that the compound is not selected from the group consisting of:

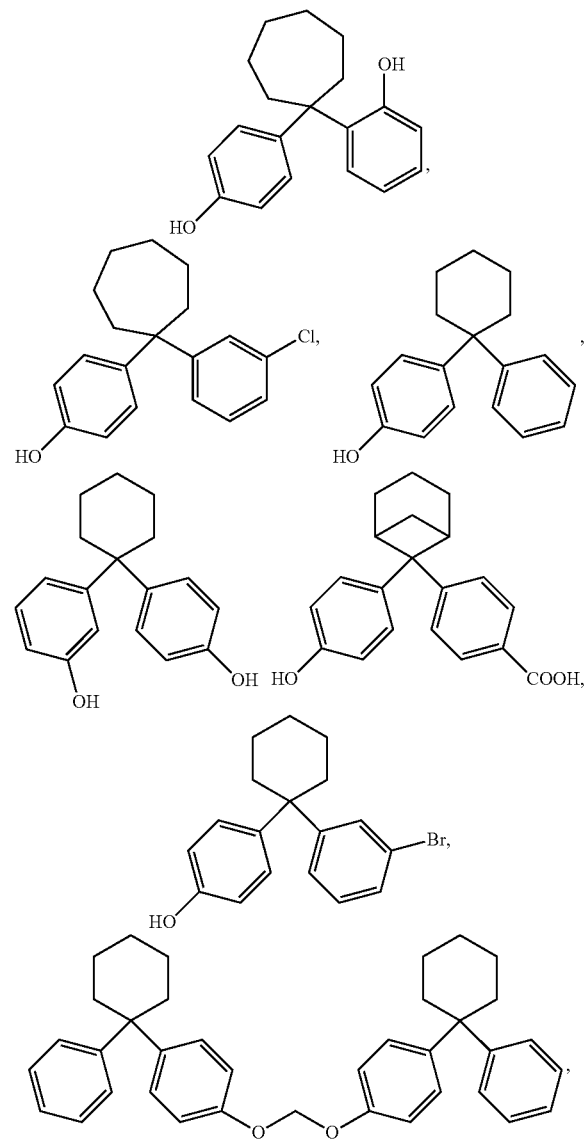

-continued
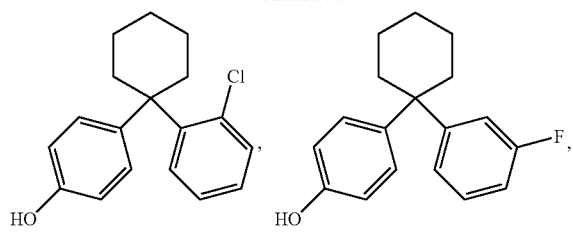
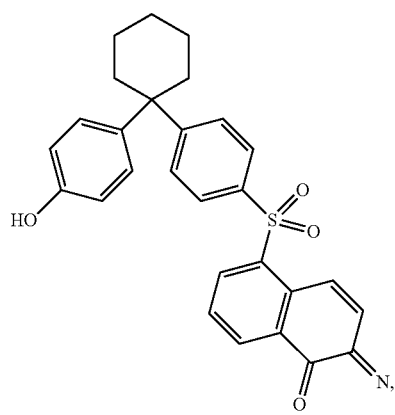
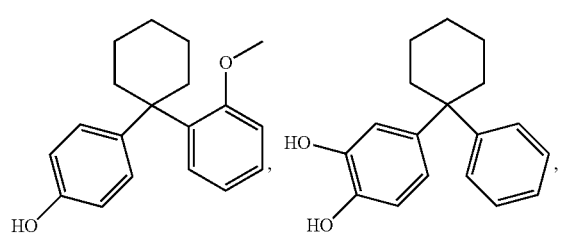
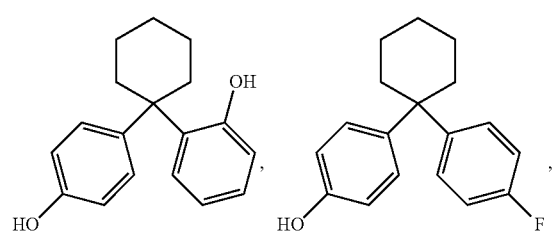
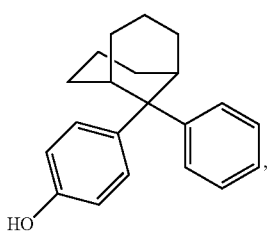
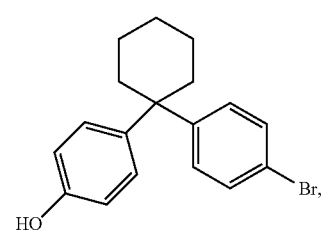
-continued
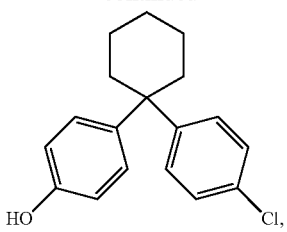
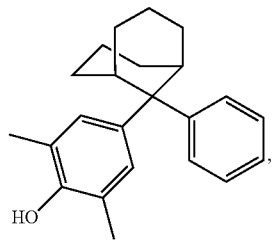
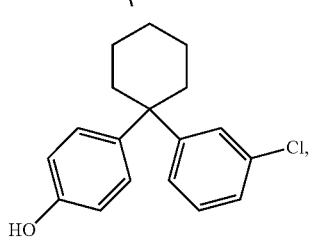
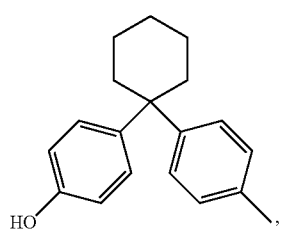
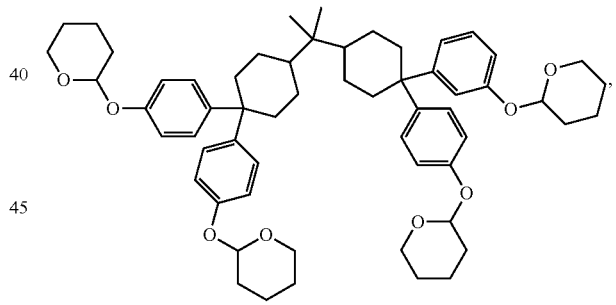
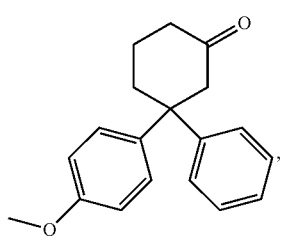
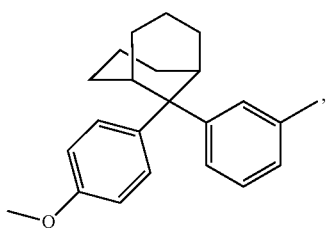

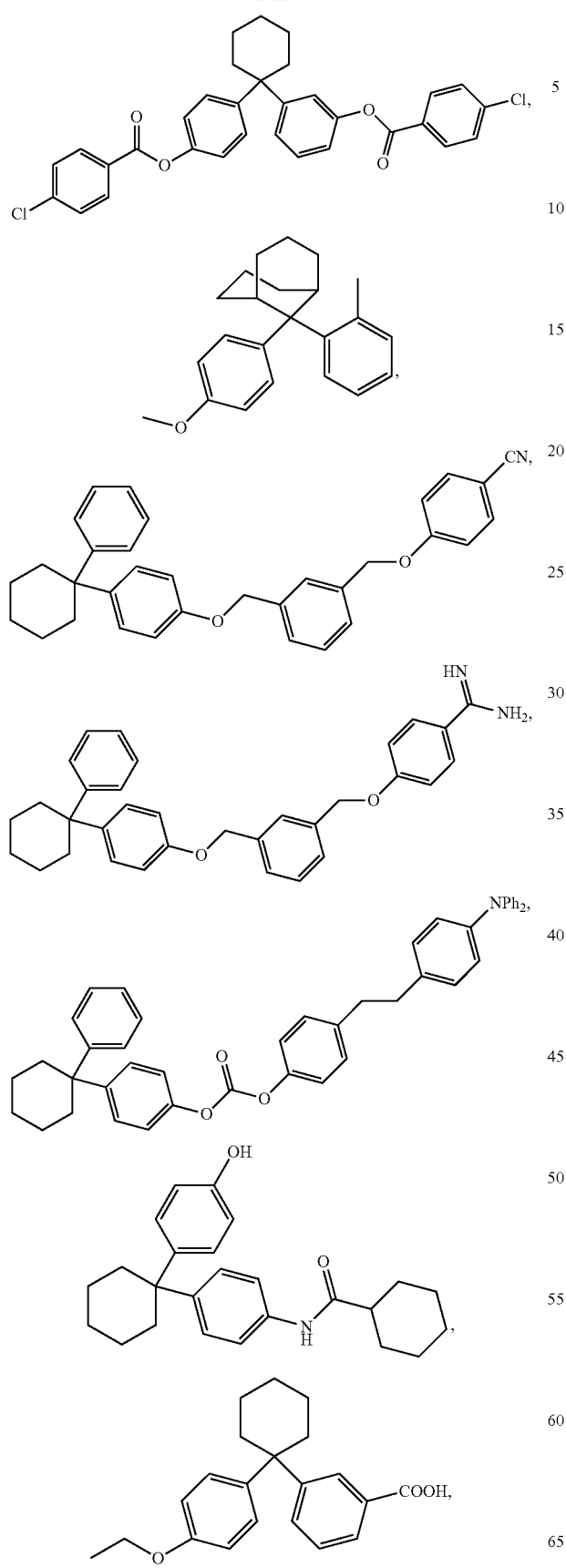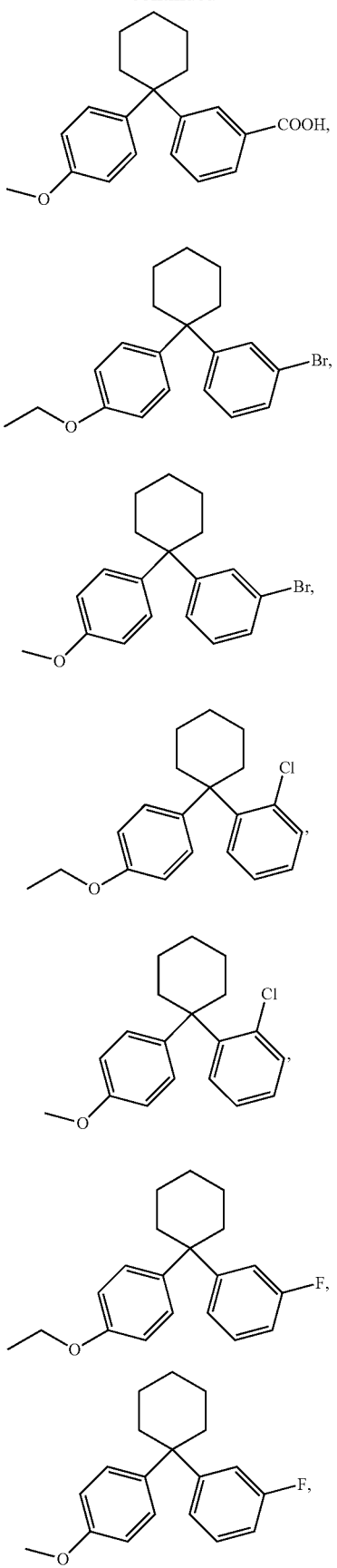

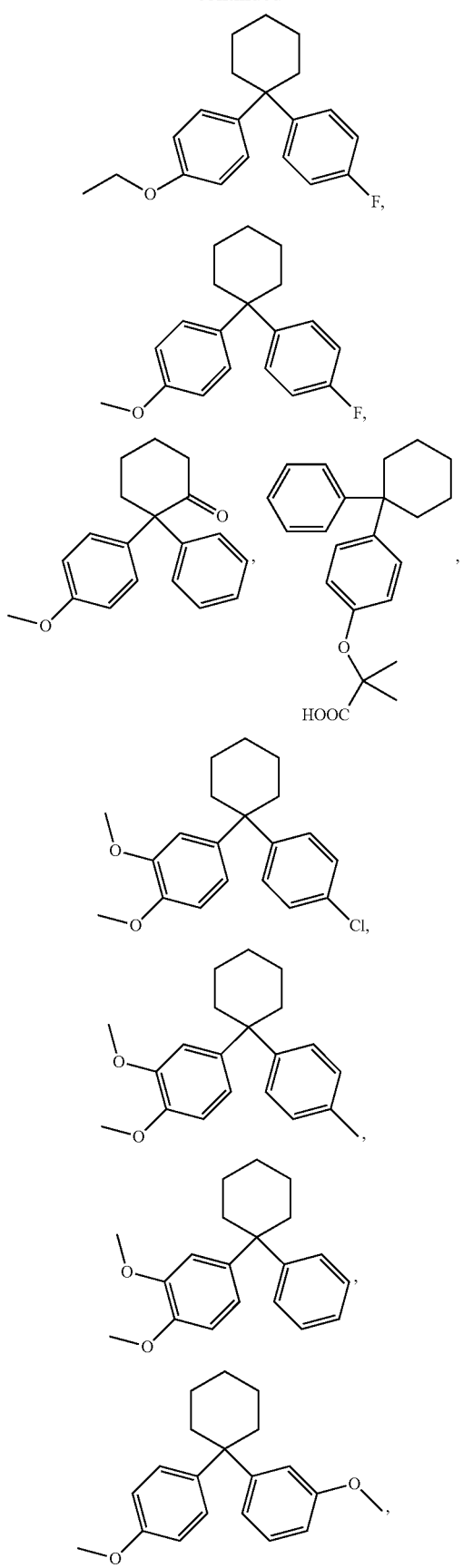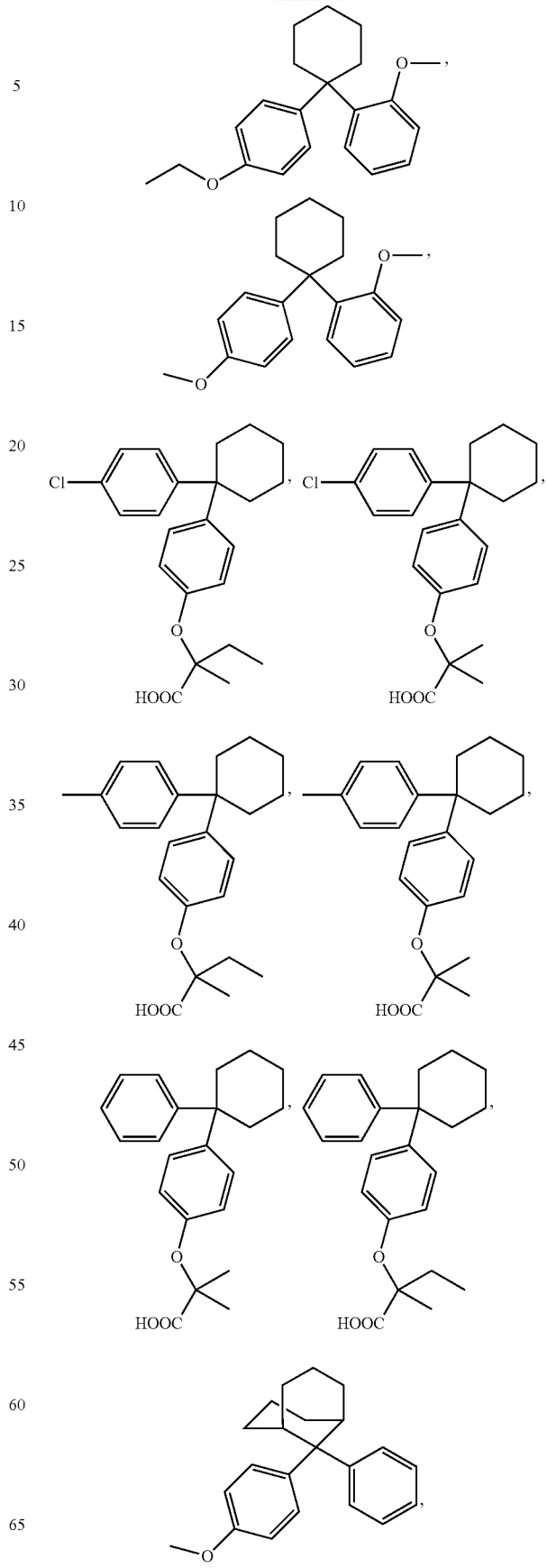

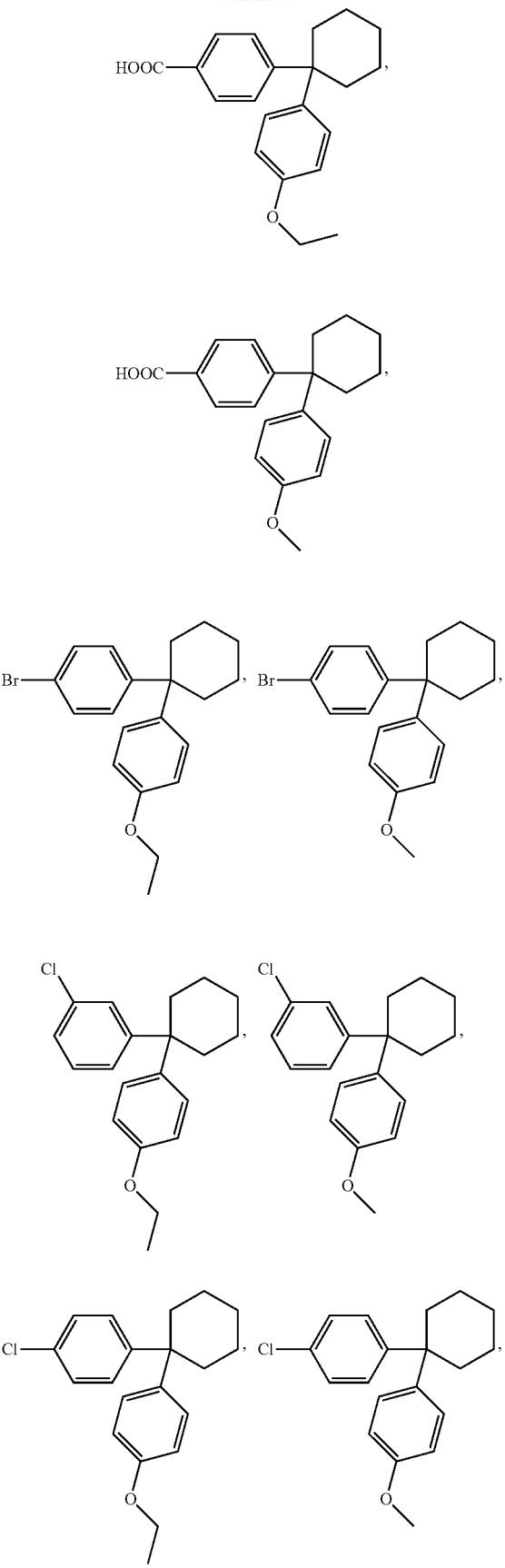
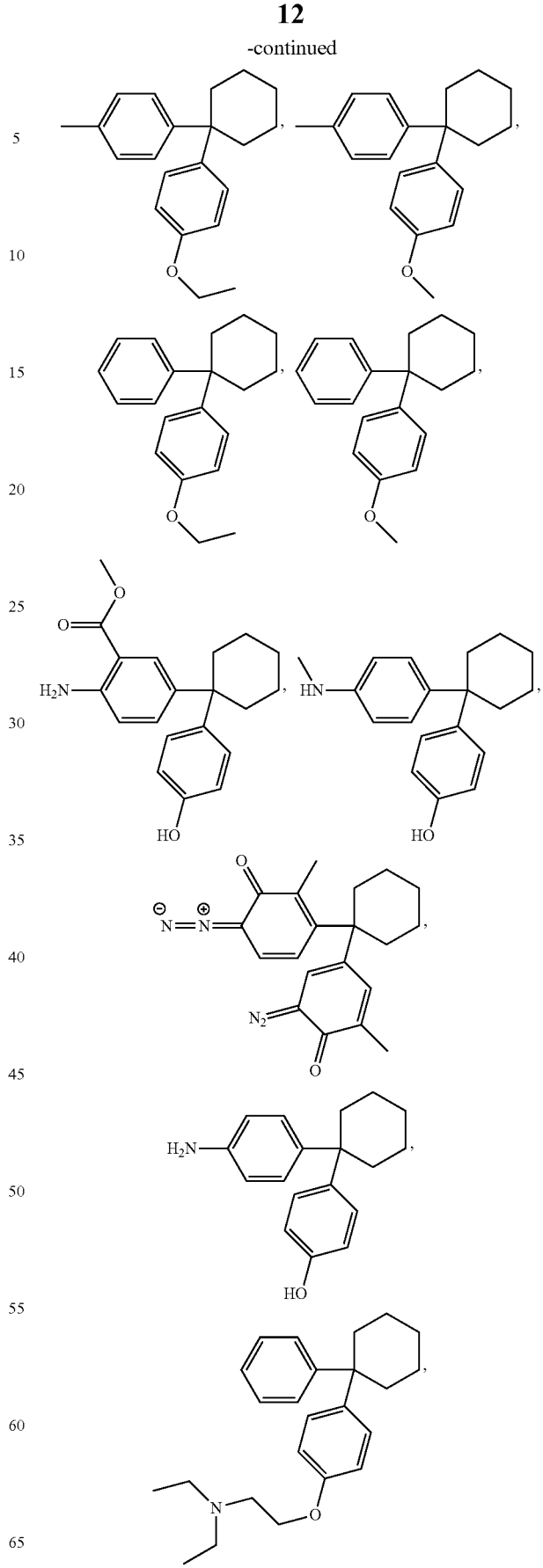

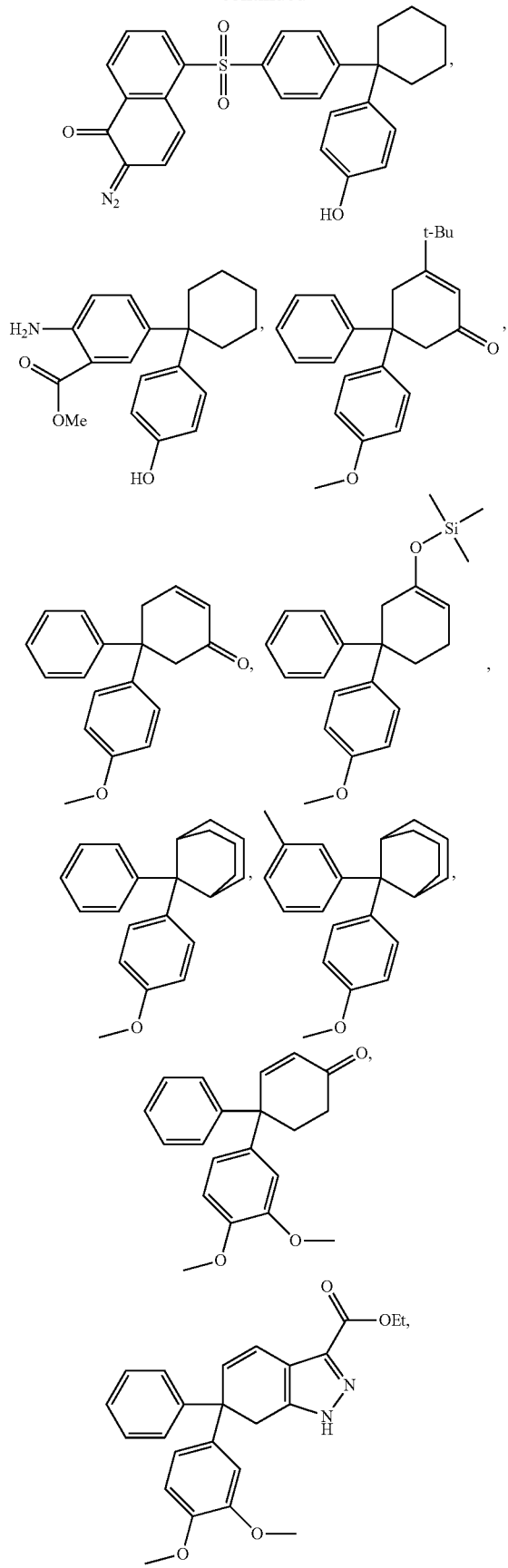

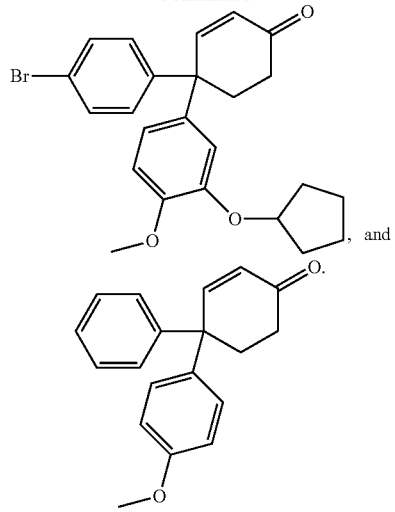

In some embodiments of the compound of formula I, n is an integer selected from the group consisting of 3, 4, and 5; $R_1$ is selected from the group consisting of hydrogen, $C_1$-$C_4$ straight chained or branched alkyl, $C_1$-$C_4$ straight chained or branched alkenyl, $C_1$-$C_4$ straight chained or branched perhaloalkyl, substituted or unsubstituted aryl, —(C=O)$R_6$, —S(=O)$_2$NR$_{5a}$R$_{5b}$, —P(=O)(OR$_6$)$_2$, and —CH$_2$C(=O) $R_5$; $R_2$, $R_{2a}$, $R_{2b}$, $R_{2c}$ are separately selected from the group consisting of hydrogen, $C_1$-$C_5$ straight chained or branched alkyl, $C_1$-$C_5$ alkenyl, hydroxy, halogen, sulfonyl, perhaloalkyl, —CN, —OR$_6$, —C(=O)R$_6$, —C(=O)OR$_6$, —C(=O)NR$_6$R$_{6a}$, —N(R$_6$)—C(=O)R$_{6a}$, —N(R$_6$)—S(=O)$_2$R$_{6a}$, —OC(=O)R$_6$, and —SR$_6$; each $R_3$ is separately selected from the group consisting of hydrogen, $C_1$-$C_5$ straight chained or branched alkyl, $C_1$-$C_5$ alkenyl, cycloalkyl, cycloalkenyl, hydroxy, halogen, sulfonyl, perhaloalkyl, —CN, =O, and —OR$_6$, or each $R_3$ is separately absent to accommodate a double bond; $R_4$, $R_{4a}$, $R_{4b}$, $R_{4c}$ are separately selected from the group consisting hydrogen, $C_1$-$C_5$ straight chained or branched alkyl, $C_1$-$C_5$ alkenyl, hydroxy, halogen, sulfonyl, perhaloalkyl, —OR$_6$, —CN, —C(=O)R$_6$, —C(=O)OR$_6$, —C(=O)NR$_6$R$_{6a}$, —S(=O)$_2$NR$_6$R$_{6a}$, —N(R$_6$)—C(=O)R$_{6a}$, —OC(=Z)R$_6$, —N(R$_6$)—S(=O)$_2$R$_{6a}$, and —SR$_6$; and $R_5$ is selected from the group consisting of hydrogen, $C_1$-$C_5$ straight chained or branched alkyl, halogen, —CN, —SR$_6$, sulfonyl, and perhaloalkyl. In one of these embodiments, $R_1$ is selected from the group consisting of —(C=O)R$_6$, —S(=O)$_2$NR$_{5a}$R$_{5b}$, —P(=O)(OR$_6$)$_2$, and —CH$_2$C(=O)R$_5$ In another embodiment of the compound of formula I, n is 3; $R_1$ is selected from the group consisting of hydrogen, $C_1$-$C_5$ straight chained or branched alkyl, substituted or unsubstituted aryl, —(C=O)R$_6$, —S(=O)$_2$NR$_{5a}$R$_{5b}$, —P(=O)(OR$_6$)$_2$, and —CH$_2$C(=O)R$_5$; $R_2$, $R_{2a}$, $R_{2b}$, $R_{2c}$ are separately selected from the group consisting of hydrogen, $C_1$-$C_5$ straight chained or branched alkyl, F, Cl, Br, perhaloalkyl, —CN, —OR$_6$, and —SR$_6$; each $R_3$ is separately selected from the group consisting of hydrogen, $C_1$-$C_5$ straight chained or branched alkyl, $C_1$-$C_5$ alkenyl, cycloalkyl, halogen, perhaloalkyl, —CN, and —OR$_6$, or each $R_3$ is separately absent to accommodate a double bond; each $R_4$, $R_{4a}$, $R_{4b}$, $R_{4c}$ is separately selected from the group consisting hydrogen, $C_1$-$C_5$ straight chained or branched alkyl, halogen, sulfonyl, perhaloalkyl, —OR$_6$, —CN, —N(R$_6$)—S(=O)$_2$ $R_{6a}$, and —$SR_6$; and $R_5$ is selected from the group consisting of hydrogen, $C_1$-$C_5$ straight chained or branched alkyl, F, Cl, —CN, —$SR_6$, and $CF_3$.

In another embodiment of the compound of formula I, $R_1$ is hydrogen. In still another embodiment of the compound of formula I, $R_5$ is hydrogen or halogen.

In various embodiments, the compound of formula I is selected from the group consisting of:

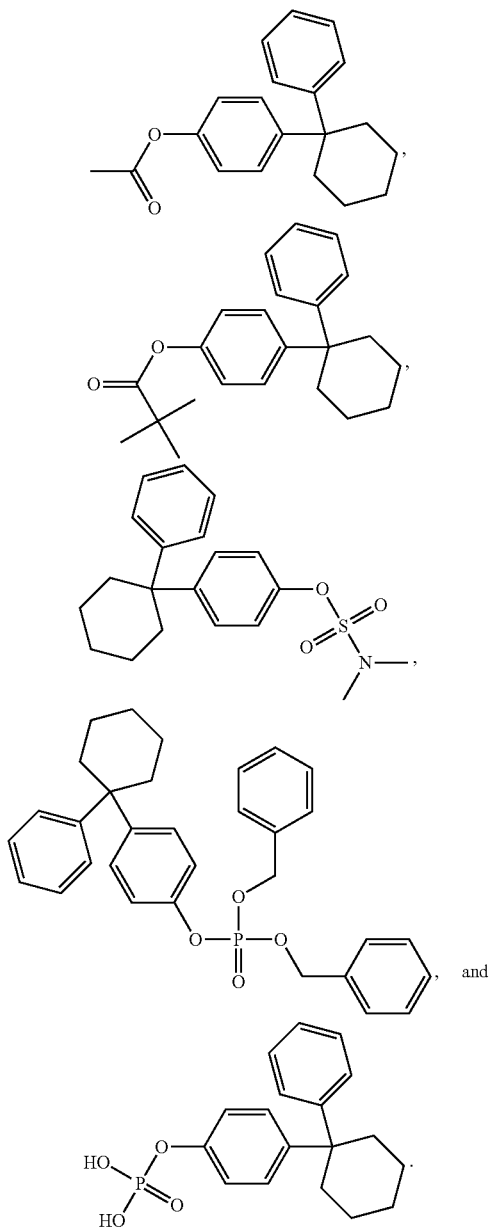

or a pharmaceutically acceptable salt or prodrug thereof.

Another embodiment disclosed herein is a pharmaceutical composition, comprising a pharmaceutically acceptable amount of a compound of formula I.

Another embodiment disclosed herein is a method of treating or preventing disorders selected from the group consisting of inflammatory bowel syndrome; Crohn's disease; ulcerative proctitis or colitis; prostatic hypertrophy; uterine leiomyomas; breast carcinoma; endometrial carcinoma; poly- cystic ovary syndrome; endometrial polyps; benign breast disease; adenomyosis; ovarian carcinoma; melanoma; prostate carcinoma; colon carcinoma; brain tumors including glioblastoma, astrocytoma, glioma, or meningioma; prostatitis; interstitial cystitis; bone density loss including osteoporosis or osteopenia; discholesterolemia; dislipidemia; cardiovascular disease; atherosclerosis; hypertension; peripheral vascular disease; restenosis; vasospasm; neurodegenerative disorders including Alzheimer's disease, Huntington's disease, Parkinson's disease or other dementias; spinal cord injury; cognitive decline; stroke; anxiety; vaginal atrophy; vulvar atrophy; atrophic vaginitis; vaginal dryness; pruritus; dyspareunia; frequent urination; urinary incontinence; urinary tract infections; vasomotor symptoms including flushing or hot flashes; arthritis including rheumatoid arthritis, osteoarthritis, or arthropathiesendometriosis; psoriasis; dermatitis; asthma; pleurisy; multiple sclerosis; systemic lupus erthematosis; uveitis; sepsis; hemmorhagic shock; type II diabetes; acute or chronic inflammation; lung disorders including asthma or chronic obstructive pulmonary disease; ophthalmological disorders including glaucoma, dry eye, or macular degeneration; and free radical induced disease states; including:

identifying a subject in need of the treating or preventing; and administering to the subject a pharmaceutically effective amount of a compound of formula I:

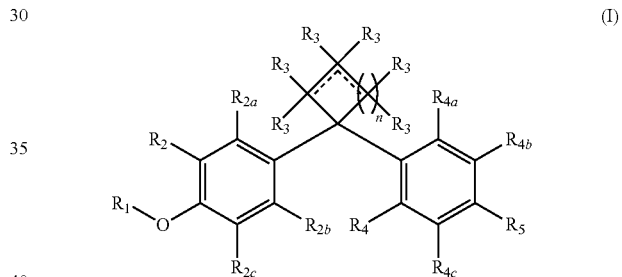

(I)

or a pharmaceutically acceptable salt or prodrug thereof, wherein:

n is an integer selected from the group consisting of 3, 4, 5 and 6;

$R_1$ is selected from the group consisting of hydrogen, $C_1$-$C_8$ straight chained or branched alkyl, $C_1$-$C_8$ straight chained or branched alkenyl, cycloalkyl, cycloalkenyl, substituted or unsubstituted heteroaryl, substituted or unsubstituted aryl, substituted or unsubstituted heteroalicyclyl, sulphonyl, $C_1$-$C_8$ straight chained or branched perhaloalkyl, —C(=Z)$R_6$, —C(=Z)O$R_6$, —C(=Z)N($R_6$)$_2$, —S(=O)$_2$N$R_{5a}R_{5b}$, —P(=O)(O$R_6$)$_2$, and —CH$_2$C(=O)$R_5$;

$R_2$, $R_{2a}$, $R_{2b}$, $R_{2c}$ are separately selected from the group consisting of hydrogen, alkyl, alkenyl, cycloalkyl, cycloalkenyl, substituted or unsubstituted aryl, substituted or unsubstituted heteroaryl, substituted or unsubstituted heteroalicyclyl, hydroxy, halogen, sulfonyl, perhaloalkyl, —CN, —O$R_6$, —N$R_6R_{6a}$, —N$R_6$N$R_{6a}R_{6b}$, —N$R_6$N=C$R_{6a}R_{6b}$, —N($R_6$)C($R_{6a}$)=N$R_{6b}$, —C(=Z)$R_6$, —C(=Z)O$R_6$, —C(=Z)N$R_6R_{6a}$, —N($R_6$)—C(=Z)$R_{6a}$, —N($R_6$)—C(=Z)N$R_{6b}R_{6a}$, —OC(=Z)$R_6$, —N($R_6$)—S(=O)$_2R_{6a}$, and —$SR_6$;

each $R_3$ is separately selected from the group consisting of hydrogen, alkyl, alkenyl, cycloalkyl, cycloalkenyl, substituted or unsubstituted aryl, substituted or unsubstituted heteroaryl, substituted or unsubstituted heteroalicyclyl, hydroxy, halogen, sulfonyl, perhaloalkyl, —CN, =O, and —OR$_6$, or are separately absent to accommodate a double bond;
two R$_3$ groups are optionally bound together to form a substituted or unsubstituted C$_3$-C$_9$ cycloalkyl or C$_3$-C$_9$ heteroalicyclyl;
R$_{2a}$ is optionally bound to one R$_3$ group to form a substituted or unsubstituted C$_4$-C$_9$ heteroalicyclic, C$_4$-C$_9$ cycloalkyl, or C$_4$-C$_9$ cycloalkenyl;
any bond represented by a dashed and solid line represents a bond selected from the group consisting of a single bond and a double bond;
R$_4$, R$_{4a}$, R$_{4b}$, R$_{4c}$ are separately selected from the group consisting of hydrogen, alkyl, alkenyl, cycloalkyl, cycloalkenyl, substituted or unsubstituted aryl, substituted or unsubstituted heteroaryl, substituted or unsubstituted heteroalicyclyl, hydroxy, nitro, halogen, sulfonyl, perhaloalkyl, —OR$_6$, —NR$_6$R$_{6a}$, —NR$_6$NR$_{6a}$R$_{6b}$, —NR$_6$N=CR$_{6a}$R$_{6b}$, —N(R$_6$)C(R$_{6a}$)=NR$_{6b}$, —CN, —C(=Z)R$_6$, —C(=Z)OR$_6$, —C(=Z)NR$_6$R$_{6a}$, —S(=Z)NR$_6$R$_{6a}$, —N(R$_6$)—C(=Z)R$_{6a}$, —N(R$_6$)—C(=Z)NR$_{6b}$R$_{6a}$, —OC(=Z)R$_6$, —N(R$_6$)—S(=O)$_2$R$_{6a}$, and —SR$_6$;
R$_{4a}$ and R$_{4b}$ are optionally bound together to form an aryl, heteroaryl, or heteroalicyclyl;
R$_5$ is selected from the group consisting of hydrogen, alkyl, alkenyl, cycloalkyl, cycloalkenyl, halogen, —CN, —SR$_6$, sulfonyl, —C(=O)NR$_6$R$_{6a}$, —C(=O)R$_6$, —NR$_6$R$_{6a}$, —COOR$_6$, and perhaloalkyl;
Z is oxygen or sulfur; and
R$_6$, R$_{6a}$ and R$_{6b}$ are separately selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, and substituted or unsubstituted heteroalicyclyl.

In some embodiments, the disorder is selected from the group consisting of inflammatory bowel syndrome, Crohn's disease, and ulcerative proctitis or colitis.

In some embodiments, the disorder is selected from the group consisting of prostatic hypertrophy, uterine leiomyomas, breast carcinoma, endometrial carcinoma, polycystic ovary syndrome, endometrial polyps, benign breast disease, adenomyosis, ovarian carcinoma, melanoma, prostate carcinoma, colon carcinoma, and brain tumors including glioblastoma, astrocytoma, glioma, or meningioma.

In some embodiments, the disorder is selected from the group consisting of prostatitis and interstitial cystitis.

In some embodiments, the disorder is bone density loss including osteoporosis and osteopenia.

In some embodiments, the disorder is selected from the group consisting of discholesterolemia and dislipidemia.

In some embodiments, the disorder is selected from the group consisting of cardiovascular disease, atherosclerosis, hypertension, peripheral vascular disease, restenosis and vasospasm.

In some embodiments, the disorder is a neurodegenerative disorder including Alzheimer's disease, Huntington's disease, Parkinson's disease or other dementia.

In some embodiments, the disorder is a spinal cord injury.

In some embodiments, the disorder is selected from the group consisting of cognitive decline, stroke, and anxiety.

In some embodiments, the disorder is selected from the group consisting of vaginal atrophy, vulvar atrophy, atrophic vaginitis, vaginal dryness, pruritus, dyspareunia, frequent urination, urinary incontinence, and urinary tract infections.

In some embodiments, the disorder is one or more vasomotor symptoms including flushing or hot flashes.

In some embodiments, the disorder is endometriosis.

In some embodiments, the disorder is arthritis including rheumatoid arthritis, osteoarthritis, or arthropathies.

In some embodiments, the disorder is selected from the group consisting of psoriasis and dermatitis.

In some embodiments, the disorder is selected from the group consisting of asthma and pleurisy.

In some embodiments, the disorder is selected from the group consisting of multiple sclerosis, systemic lupus erthematosis, uveitis, sepsis, and hemmorhagic shock.

In some embodiments, the disorder is type II diabetes.

In some embodiments, the disorder is selected from the group consisting of acute and chronic inflammation.

In some embodiments, the disorder is a lung disorders including asthma or chronic obstructive pulmonary disease.

In some embodiments, the disorder is an ophthalmologic disorders including glaucoma, dry eye, or macular degeneration.

In some embodiments, the disorder is a free radical induced disease state.

In some embodiments, the disorder is acute or chronic pain. In one embodiment, the pain is neuropathic pain.

Another embodiment disclosed herein is a method of hormonal replacement therapy, comprising:
identifying a subject in need of hormonal replacement; and
administering to the subject a pharmaceutically effective amount of a compound of formula I:

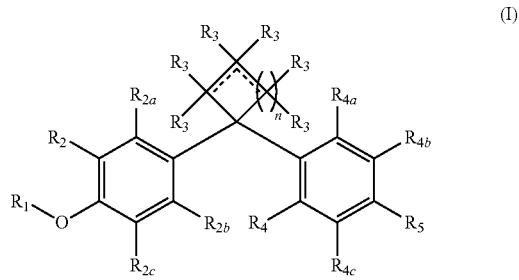

or a pharmaceutically acceptable salt or prodrug thereof, wherein:
n is an integer selected from the group consisting of 3, 4, 5 and 6;
R$_1$ is selected from the group consisting of hydrogen, C$_1$-C$_8$ straight chained or branched alkyl, C$_1$-C$_8$ straight chained or branched alkenyl, cycloalkyl, cycloalkenyl, substituted or unsubstituted heteroaryl, substituted or unsubstituted aryl, substituted or unsubstituted heteroalicyclyl, sulphonyl, C$_1$-C$_8$ straight chained or branched perhaloalkyl, —C(=Z)R$_6$, —C(=Z)OR$_6$, —C(=Z)N(R$_6$)$_2$, —S(=O)$_2$NR$_{5a}$R$_{5b}$, —P(=O)(OR$_6$)$_2$, and —CH$_2$OC(=O)R$_5$;
R$_2$, R$_{2a}$, R$_{2b}$, R$_{2c}$ are separately selected from the group consisting of hydrogen, alkyl, alkenyl, cycloalkyl, cycloalkenyl, substituted or unsubstituted aryl, substituted or unsubstituted heteroaryl, substituted or unsubstituted heteroalicyclyl, hydroxy, halogen, sulfonyl, perhaloalkyl, —CN, —OR$_6$, —NR$_6$R$_{6a}$, —NR$_6$NR$_{6a}$R$_{6b}$, —NR$_6$N=CR$_{6a}$R$_{6b}$, —N(R$_6$)C(R$_{6a}$)=NR$_{6b}$, —C(=Z)R$_6$, —C(=Z)OR$_6$, —C(=Z)NR$_6$R$_{6a}$, —N(R$_6$)—C(=Z)R$_{6a}$, —N(R$_6$)—C(=Z)NR$_{6b}$R$_{6a}$, —OC(=Z)R$_6$, —N(R$_6$)—S(=O)$_2$R$_{6a}$, and —SR$_6$;

each R$_3$ is separately selected from the group consisting of hydrogen, alkyl, alkenyl, cycloalkyl, cycloalkenyl, substituted or unsubstituted aryl, substituted or unsubstituted heteroaryl, substituted or unsubstituted heteroalicyclyl, hydroxy, halogen, sulfonyl, perhaloalkyl, —CN, =O, and —OR$_6$, or are separately absent to accommodate a double bond;

two R$_3$ groups are optionally bound together to form a substituted or unsubstituted C$_3$-C$_9$ cycloalkyl or C$_3$-C$_9$ heteroalicyclyl;

R$_{2a}$ is optionally bound to one R$_3$ group to form a substituted or unsubstituted C$_4$-C$_9$ heteroalicyclic, C$_4$-C$_9$ cycloalkyl, or C$_4$-C$_9$ cycloalkenyl;

R$_{4a}$ is optionally bound to one R$_3$ group to form a substituted or unsubstituted C$_4$-C$_9$ heteroalicyclic, C$_4$-C$_9$ cycloalkyl, or C$_4$-C$_9$ cycloalkenyl;

any bond represented by a dashed and solid line represents a bond selected from the group consisting of a single bond and a double bond;

R$_4$, R$_{4a}$, R$_{4b}$, R$_{4c}$ are separately selected from the group consisting of hydrogen, alkyl, alkenyl, cycloalkyl, cycloalkenyl, substituted or unsubstituted aryl, substituted or unsubstituted heteroaryl, substituted or unsubstituted heteroalicyclyl, hydroxy, nitro, halogen, sulfonyl, perhaloalkyl, —OR$_6$, —NR$_6$R$_{6a}$, —NR$_6$NR$_{6a}$R$_{6b}$, —NR$_6$N=CR$_{6a}$R$_{6b}$, —N(R$_6$)C(R$_{6a}$)=NR$_{6b}$, —CN, —C(=Z)R$_6$, —C(=Z)OR$_6$, —C(=Z)NR$_6$R$_{6a}$, —S(=Z)NR$_6$R$_{6a}$, —N(R$_6$)—C(=Z)R$_{6a}$, —N(R$_6$)—C(=Z)NR$_{6b}$R$_{6a}$, —OC(=Z)R$_6$, —N(R$_6$)—S(=O)$_2$R$_{6a}$, and —SR$_6$;

R$_{4a}$ and R$_{4b}$ are optionally bound together to form an aryl, heteroaryl, or heteroalicyclyl;

R$_5$ is selected from the group consisting of hydrogen, alkyl, alkenyl, cycloalkyl, cycloalkenyl, halogen, —CN, —SR$_6$, sulfonyl, —C(=O)NR$_6$R$_{6a}$, —C(=O)R$_6$, —NR$_6$R$_{6a}$, —COOR$_6$, and perhaloalkyl;

Z is oxygen or sulfur; and

R$_6$, R$_{6a}$ and R$_{6b}$ are separately selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, and substituted or unsubstituted heteroalicyclyl.

Another embodiment disclosed herein is a method of lowering cholesterol, triglycerides, or LDL levels, comprising: identifying a subject in need of the lowering; and administering to the subject a pharmaceutically effective amount of a compound of formula I:

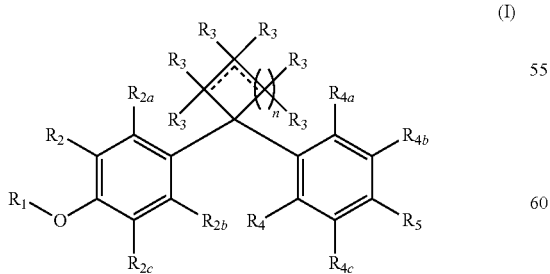

(I)

or a pharmaceutically acceptable salt or prodrug thereof, wherein:

n is an integer selected from the group consisting of 3, 4, 5 and 6;

R$_1$ is selected from the group consisting of hydrogen, C$_1$-C$_8$ straight chained or branched alkyl, C$_1$-C$_8$ straight chained or branched alkenyl, cycloalkyl, cycloalkenyl, substituted or unsubstituted heteroaryl, substituted or unsubstituted aryl, substituted or unsubstituted heteroalicyclyl, sulphonyl, C$_1$-C$_8$ straight chained or branched perhaloalkyl, —C(=Z)R$_6$, —C(=Z)OR$_6$, —C(=Z)N(R$_6$)$_2$, —S(=O)$_2$NR$_{5a}$R$_{5b}$, —P(=O)(OR$_6$)$_2$, and —CH$_2$OC(=O)R$_5$;

R$_2$, R$_{2a}$, R$_{2b}$, R$_{2c}$ are separately selected from the group consisting of hydrogen, alkyl, alkenyl, cycloalkyl, cycloalkenyl, substituted or unsubstituted aryl, substituted or unsubstituted heteroaryl, substituted or unsubstituted heteroalicyclyl, hydroxy, halogen, sulfonyl, perhaloalkyl, —CN, —OR$_6$, —NR$_6$R$_{6a}$, —NR$_6$NR$_{6a}$R$_{6b}$, —NR$_6$N=CR$_{6a}$R$_{6b}$, —N(R$_6$)C(R$_{6a}$)=NR$_{6b}$, —C(=Z)R$_6$, —C(=Z)OR$_6$, —C(=Z)NR$_6$R$_{6a}$, —N(R$_6$)—C(=Z)R$_{6a}$, —N(R$_6$)—C(=Z)NR$_{6b}$R$_{6a}$, —OC(=Z)R$_6$, —N(R$_6$)—S(=O)$_2$R$_{6a}$, and —SR$_6$;

each R$_3$ is separately selected from the group consisting of hydrogen, alkyl, alkenyl, cycloalkyl, cycloalkenyl, substituted or unsubstituted aryl, substituted or unsubstituted heteroaryl, substituted or unsubstituted heteroalicyclyl, hydroxy, halogen, sulfonyl, perhaloalkyl, —CN, =O, and —OR$_6$, or are separately absent to accommodate a double bond;

two R$_3$ groups are optionally bound together to form a substituted or unsubstituted C$_3$-C$_9$ cycloalkyl or C$_3$-C$_9$ heteroalicyclyl;

R$_{2a}$ is optionally bound to one R$_3$ group to form a substituted or unsubstituted C$_4$-C$_9$ heteroalicyclic, C$_4$-C$_9$ cycloalkyl, or C$_4$-C$_9$ cycloalkenyl;

R$_{4a}$ is optionally bound to one R$_3$ group to form a substituted or unsubstituted C$_4$-C$_9$ heteroalicyclic, C$_4$-C$_9$ cycloalkyl, or C$_4$-C$_9$ cycloalkenyl;

any bond represented by a dashed and solid line represents a bond selected from the group consisting of a single bond and a double bond;

R$_4$, R$_{4a}$, R$_{4b}$, R$_{4c}$ are separately selected from the group consisting of hydrogen, alkyl, alkenyl, cycloalkyl, cycloalkenyl, substituted or unsubstituted aryl, substituted or unsubstituted heteroaryl, substituted or unsubstituted heteroalicyclyl, hydroxy, nitro, halogen, sulfonyl, perhaloalkyl, —OR$_6$, —NR$_6$R$_{6a}$, —NR$_6$NR$_{6a}$R$_{6b}$, —NR$_6$N=CR$_{6a}$R$_{6b}$, —N(R$_6$)C(R$_{6a}$)=NR$_{6b}$, —CN, —C(=Z)R$_6$, —C(=Z)OR$_6$, —C(=Z)NR$_6$R$_{6a}$, —S(=Z)NR$_6$R$_{6a}$, —N(R$_6$)—C(=Z)R$_{6a}$, —N(R$_6$)—C(=Z)NR$_{6b}$R$_{6a}$, —OC(=Z)R$_6$, —N(R$_6$)—S(=O)$_2$R$_{6a}$, and —SR$_6$;

R$_{4a}$ and R$_{4b}$ are optionally bound together to form an aryl, heteroaryl, or heteroalicyclyl;

R$_5$ is selected from the group consisting of hydrogen, alkyl, alkenyl, cycloalkyl, cycloalkenyl, halogen, —CN, —SR$_6$, sulfonyl, —C(=O)NR$_6$R$_{6a}$, —C(=O)R$_6$, —NR$_6$R$_{6a}$, —COOR$_6$, and perhaloalkyl;

Z is oxygen or sulfur; and

R$_6$, R$_{6a}$ and R$_{6b}$ are separately selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, and substituted or unsubstituted heteroalicyclyl.

Another embodiment disclosed herein is a method of treating impaired cognition or providing neuroprotection, comprising:

identifying a subject in need of the treating or neuroprotection; and administering to the subject a pharmaceutically effective amount of a compound of formula I:

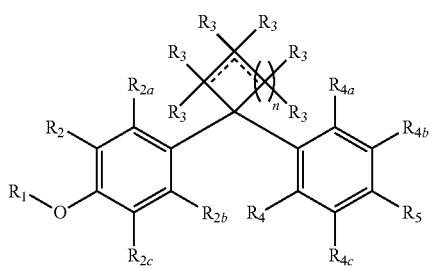

or a pharmaceutically acceptable salt or prodrug thereof, wherein:

n is an integer selected from the group consisting of 3, 4, 5 and 6;

$R_1$ is selected from the group consisting of hydrogen, $C_1$-$C_8$ straight chained or branched alkyl, $C_1$-$C_8$ straight chained or branched alkenyl, cycloalkyl, cycloalkenyl, substituted or unsubstituted heteroaryl, substituted or unsubstituted aryl, substituted or unsubstituted heteroalicyclyl, sulphonyl, $C_1$-$C_8$ straight chained or branched perhaloalkyl, —C(=Z)$R_6$, —C(=Z)O$R_6$, —C(=Z)N($R_6$)$_2$, —S(=O)$_2$N$R_{5a}R_{5b}$, —P(=O)(O$R_6$)$_2$, and —CH$_2$OC(=O)$R_5$;

$R_2$, $R_{2a}$, $R_{2b}$, $R_{2c}$ are separately selected from the group consisting of hydrogen, alkyl, alkenyl, cycloalkyl, cycloalkenyl, substituted or unsubstituted aryl, substituted or unsubstituted heteroaryl, substituted or unsubstituted heteroalicyclyl, hydroxy, halogen, sulfonyl, perhaloalkyl, —CN, —O$R_6$, —N$R_6R_{6a}$, —N$R_6$N$R_{6a}R_{6b}$, —N$R_6$N=C$R_{6a}R_{6b}$, —N($R_6$)C($R_{6a}$)=N$R_{6b}$, —C(=Z)$R_6$, —C(=Z)O$R_6$, —C(=Z)N$R_6R_{6a}$, —N($R_6$)—C(=Z)$R_{6a}$, —N($R_6$)—C(=Z)N$R_{6b}R_{6a}$, —OC(=Z)$R_6$, —N($R_6$)—S(=O)$_2R_{6a}$, and —S$R_6$;

each $R_3$ is separately selected from the group consisting of hydrogen, alkyl, alkenyl, cycloalkyl, cycloalkenyl, substituted or unsubstituted aryl, substituted or unsubstituted heteroaryl, substituted or unsubstituted heteroalicyclyl, hydroxy, halogen, sulfonyl, perhaloalkyl, —CN, =O, and —O$R_6$, or are separately absent to accommodate a double bond;

two $R_3$ groups are optionally bound together to form a substituted or unsubstituted $C_3$-$C_9$ cycloalkyl or $C_3$-$C_9$ heteroalicyclyl;

$R_{2a}$ is optionally bound to one $R_3$ group to form a substituted or unsubstituted $C_4$-$C_9$ heteroalicyclic, $C_4$-$C_9$ cycloalkyl, or $C_4$-$C_9$ cycloalkenyl;

$R_{4a}$ is optionally bound to one $R_3$ group to form a substituted or unsubstituted $C_4$-$C_9$ heteroalicyclic, $C_4$-$C_9$ cycloalkyl, or $C_4$-$C_9$ cycloalkenyl;

any bond represented by a dashed and solid line represents a bond selected from the group consisting of a single bond and a double bond;

$R_4$, $R_{4a}$, $R_{4b}$, $R_{4c}$ are separately selected from the group consisting of hydrogen, alkyl, alkenyl, cycloalkyl, cycloalkenyl, substituted or unsubstituted aryl, substituted or unsubstituted heteroaryl, substituted or unsubstituted heteroalicyclyl, hydroxy, nitro, halogen, sulfonyl, perhaloalkyl, —O$R_6$, —N$R_6R_{6a}$, —N$R_6$N$R_{6a}R_{6b}$, —N$R_6$N=C$R_{6a}R_{6b}$, —N($R_6$)C($R_{6a}$)=N$R_{6b}$, —CN, —C(=Z)$R_6$, —C(=Z)O$R_6$, —C(=Z)N$R_6R_{6a}$, —S(=Z)N$R_6R_{6a}$, —N($R_6$)—C(=Z)$R_{6a}$, —N($R_6$)—C(=Z)N$R_{6b}R_{6a}$, —OC(=Z)$R_6$, —N($R_6$)—S(=O)$_2R_{6a}$, and —S$R_6$;

$R_{4a}$ and $R_{4b}$ are optionally bound together to form an aryl, heteroaryl, or heteroalicyclyl;

$R_5$ is selected from the group consisting of hydrogen, alkyl, alkenyl, cycloalkyl, cycloalkenyl, halogen, —CN, —S$R_6$, sulfonyl, —C(=O)N$R_6R_{6a}$, —C(=O)$R_6$, —N$R_6R_{6a}$, —COO$R_6$, and perhaloalkyl;

Z is oxygen or sulfur; and $R_6$, $R_{6a}$ and $R_{6b}$ are separately selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, and substituted or unsubstituted heteroalicyclyl.

Another embodiment disclosed herein is a method of preventing conception, comprising administering to a subject a pharmaceutically effective amount of a compound of formula I:

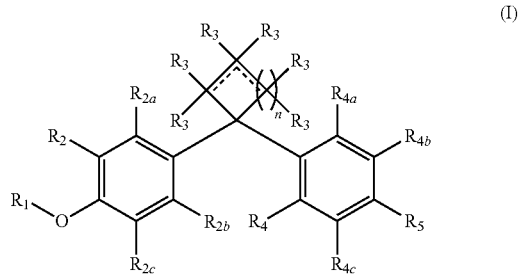

or a pharmaceutically acceptable salt or prodrug thereof, wherein:

n is an integer selected from the group consisting of 3, 4, 5 and 6;

$R_1$ is selected from the group consisting of hydrogen, $C_1$-$C_8$ straight chained or branched alkyl, $C_1$-$C_8$ straight chained or branched alkenyl, cycloalkyl, cycloalkenyl, substituted or unsubstituted heteroaryl, substituted or unsubstituted aryl, substituted or unsubstituted heteroalicyclyl, sulphonyl, $C_1$-$C_8$ straight chained or branched perhaloalkyl, —C(=Z)$R_6$, —C(=Z)O$R_6$, —C(=Z)N($R_6$)$_2$, —S(=O)$_2$N$R_{5a}R_{5b}$, —P(=O)(O$R_6$)$_2$, and —CH$_2$OC(=O)$R_5$;

$R_2$, $R_{2a}$, $R_{2b}$, $R_{2c}$ are separately selected from the group consisting of hydrogen, alkyl, alkenyl, cycloalkyl, cycloalkenyl, substituted or unsubstituted aryl, substituted or unsubstituted heteroaryl, substituted or unsubstituted heteroalicyclyl, hydroxy, halogen, sulfonyl, perhaloalkyl, —CN, —O$R_6$, —N$R_6R_{6a}$, —N$R_6$N$R_{6a}R_{6b}$, —N$R_6$N=C$R_{6a}R_{6b}$, —N($R_6$)C($R_{6a}$)=N$R_{6b}$, —C(=Z)$R_6$, —C(=Z)O$R_6$, —C(=Z)N$R_6R_{6a}$, —N($R_6$)—C(=Z)$R_{6a}$, —N($R_6$)—C(=Z)N$R_{6b}R_{6a}$, —OC(=Z)$R_6$, —N($R_6$)—S(=O)$_2R_{6a}$, and —S$R_6$;

each $R_3$ is separately selected from the group consisting of hydrogen, alkyl, alkenyl, cycloalkyl, cycloalkenyl, substituted or unsubstituted aryl, substituted or unsubstituted heteroaryl, substituted or unsubstituted heteroalicyclyl, hydroxy, halogen, sulfonyl, perhaloalkyl, —CN, =O, and —O$R_6$, or are separately absent to accommodate a double bond;

two $R_3$ groups are optionally bound together to form a substituted or unsubstituted $C_3$-$C_9$ cycloalkyl or $C_3$-$C_9$ heteroalicyclyl;

$R_{2a}$ is optionally bound to one $R_3$ group to form a substituted or unsubstituted $C_4$-$C_9$ heteroalicyclic, $C_4$-$C_9$ cycloalkyl, or $C_4$-$C_9$ cycloalkenyl;

$R_{4a}$ is optionally bound to one $R_3$ group to form a substituted or unsubstituted $C_4$-$C_9$ heteroalicyclic, $C_4$-$C_9$ cycloalkyl, or $C_4$-$C_9$ cycloalkenyl;

any bond represented by a dashed and solid line represents a bond selected from the group consisting of a single bond and a double bond;

$R_4$, $R_{4a}$, $R_{4b}$, $R_{4c}$ are separately selected from the group consisting of hydrogen, alkyl, alkenyl, cycloalkyl, cycloalkenyl, substituted or unsubstituted aryl, substituted or unsubstituted heteroaryl, substituted or unsubstituted heteroalicyclyl, hydroxy, nitro, halogen, sulfonyl, perhaloalkyl, —$OR_6$, —$NR_6R_{6a}$, —$NR_6NR_{6a}R_{6b}$, —$NR_6N$=$CR_{6a}R_{6b}$, —$N(R_6)C(R_{6a})$=$NR_{6b}$, —CN, —C(=Z)$R_6$, —C(=Z)$OR_6$, —C(=Z)$NR_6R_{6a}$, —S(=Z)$NR_6R_{6a}$, —$N(R_6)$—C(=Z)$R_{6a}$, —$N(R_6)$—C(=Z)$NR_{6b}R_{6a}$, —OC(=Z)$R_6$, —$N(R_6)$—S(=O)$_2R_{6a}$, and —$SR_6$;

$R_{4a}$ and $R_{4b}$ are optionally bound together to form an aryl, heteroaryl, or heteroalicyclyl;

$R_5$ is selected from the group consisting of hydrogen, alkyl, alkenyl, cycloalkyl, cycloalkenyl, halogen, —CN, —$SR_6$, sulfonyl, —C(=O)$NR_6R_{6a}$, —C(=O)$R_6$, —$NR_6R_{6a}$, —$COOR_6$, and perhaloalkyl;

Z is oxygen or sulfur; and $R_6$, $R_{6a}$ and $R_{6b}$ are separately selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, and substituted or unsubstituted heteroalicyclyl.

Another embodiment disclosed herein is a method of modulating or specifically agonizing one or more Estrogen receptors, comprising:

identifying a subject in need of the modulating or agonizing; and administering to the subject an effective amount of a compound of formula I:

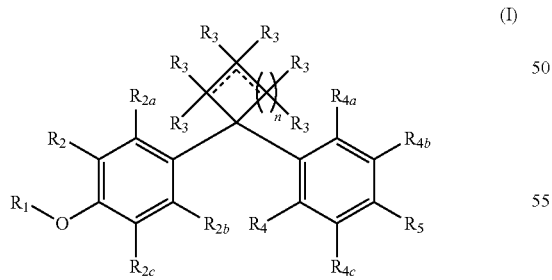

(I)

or a pharmaceutically acceptable salt or prodrug thereof, wherein:

n is an integer selected from the group consisting of 3, 4, 5 and 6;

$R_1$ is selected from the group consisting of hydrogen, $C_1$-$C_8$ straight chained or branched alkyl, $C_1$-$C_8$ straight chained or branched alkenyl, cycloalkyl, cycloalkenyl, substituted or unsubstituted heteroaryl, substituted or unsubstituted aryl, substituted or unsubstituted heteroalicyclyl, sulphonyl, $C_1$-$C_8$ straight chained or branched perhaloalkyl, —C(=Z)$R_6$, —C(=Z)$OR_6$, —C(=Z)$N(R_6)_2$, —S(=O)$_2NR_{5a}R_{5b}$, —P(=O)(OR$_6$)$_2$, and —CH$_2$OC(=O)$R_5$;

$R_2$, $R_{2a}$, $R_{2b}$, $R_{2c}$ are separately selected from the group consisting of hydrogen, alkyl, alkenyl, cycloalkyl, cycloalkenyl, substituted or unsubstituted aryl, substituted or unsubstituted heteroaryl, substituted or unsubstituted heteroalicyclyl, hydroxy, halogen, sulfonyl, perhaloalkyl, —CN, —$OR_6$, —$NR_6R_{6a}$, —$NR_6NR_{6a}R_{6b}$, —$NR_6N$=$CR_{6a}R_{6b}$, —$N(R_6)C(R_{6a})$=$NR_{6b}$, —C(=Z)$R_6$, —C(=Z)$OR_6$, —C(=Z)$NR_6R_{6a}$, —$N(R_6)$—C(=Z)$R_{6a}$, —$N(R_6)$—C(=Z)$NR_{6b}R_{6a}$, —OC(=Z)$R_6$, —$N(R_6)$—S(=O)$_2R_{6a}$, and —$SR_6$;

each $R_3$ is separately selected from the group consisting of hydrogen, alkyl, alkenyl, cycloalkyl, cycloalkenyl, substituted or unsubstituted aryl, substituted or unsubstituted heteroaryl, substituted or unsubstituted heteroalicyclyl, hydroxy, halogen, sulfonyl, perhaloalkyl, —CN, =O, and —$OR_6$, or are separately absent to accommodate a double bond;

two $R_3$ groups are optionally bound together to form a substituted or unsubstituted $C_3$-$C_9$ cycloalkyl or $C_3$-$C_9$ heteroalicyclyl;

$R_{2a}$ is optionally bound to one $R_3$ group to form a substituted or unsubstituted $C_4$-$C_9$ heteroalicyclic, $C_4$-$C_9$ cycloalkyl, or $C_4$-$C_9$ cycloalkenyl;

$R_{4a}$ is optionally bound to one $R_3$ group to form a substituted or unsubstituted $C_4$-$C_9$ heteroalicyclic, $C_4$-$C_9$ cycloalkyl, or $C_4$-$C_9$ cycloalkenyl;

any bond represented by a dashed and solid line represents a bond selected from the group consisting of a single bond and a double bond;

$R_4$, $R_{4a}$, $R_{4b}$, $R_{4c}$ are separately selected from the group consisting of hydrogen, alkyl, alkenyl, cycloalkyl, cycloalkenyl, substituted or unsubstituted aryl, substituted or unsubstituted heteroaryl, substituted or unsubstituted heteroalicyclyl, hydroxy, nitro, halogen, sulfonyl, perhaloalkyl, —$OR_6$, —$NR_6R_{6a}$, —$NR_6NR_{6a}R_{6b}$, —$NR_6N$=$CR_{6a}R_{6b}$, —$N(R_6)C(R_{6a})$=$NR_{6b}$, —CN, —C(=Z)$R_6$, —C(=Z)$OR_6$, —C(=Z)$NR_6R_{6a}$, —S(=Z)$NR_6R_{6a}$, —$N(R_6)$—C(=Z)$R_{6a}$, —$N(R_6)$—C(=Z)$NR_{6b}R_{6a}$, —OC(=Z)$R_6$, —$N(R_6)$—S(=O)$_2R_{6a}$, and —$SR_6$;

$R_{4a}$ and $R_{4b}$ are optionally bound together to form an aryl, heteroaryl, or heteroalicyclyl;

$R_5$ is selected from the group consisting of hydrogen, alkyl, alkenyl, cycloalkyl, cycloalkenyl, halogen, —CN, —$SR_6$, sulfonyl, —C(=O)$NR_6R_{6a}$, —C(=O)$R_6$, —$NR_6R_{6a}$, —$COOR_6$, and perhaloalkyl;

Z is oxygen or sulfur; and $R_6$, $R_{6a}$ and $R_{6b}$ are separately selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, and substituted or unsubstituted heteroalicyclyl.

In various embodiments of the methods described above, the compound is selected from the group consisting of:
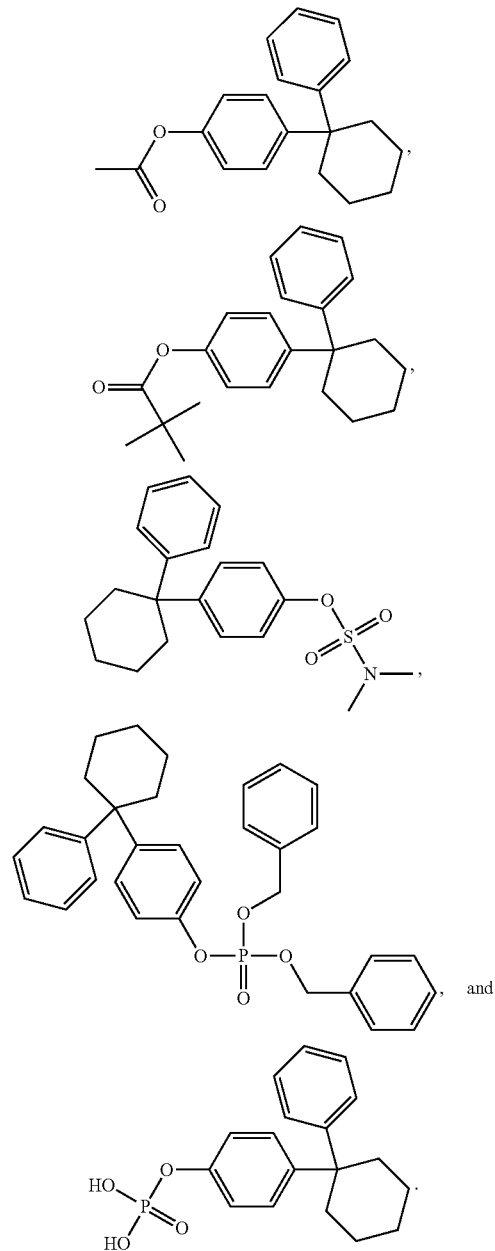
and
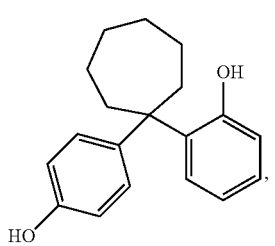
In other embodiments of the methods described above, the compound is not selected from the group consisting of:
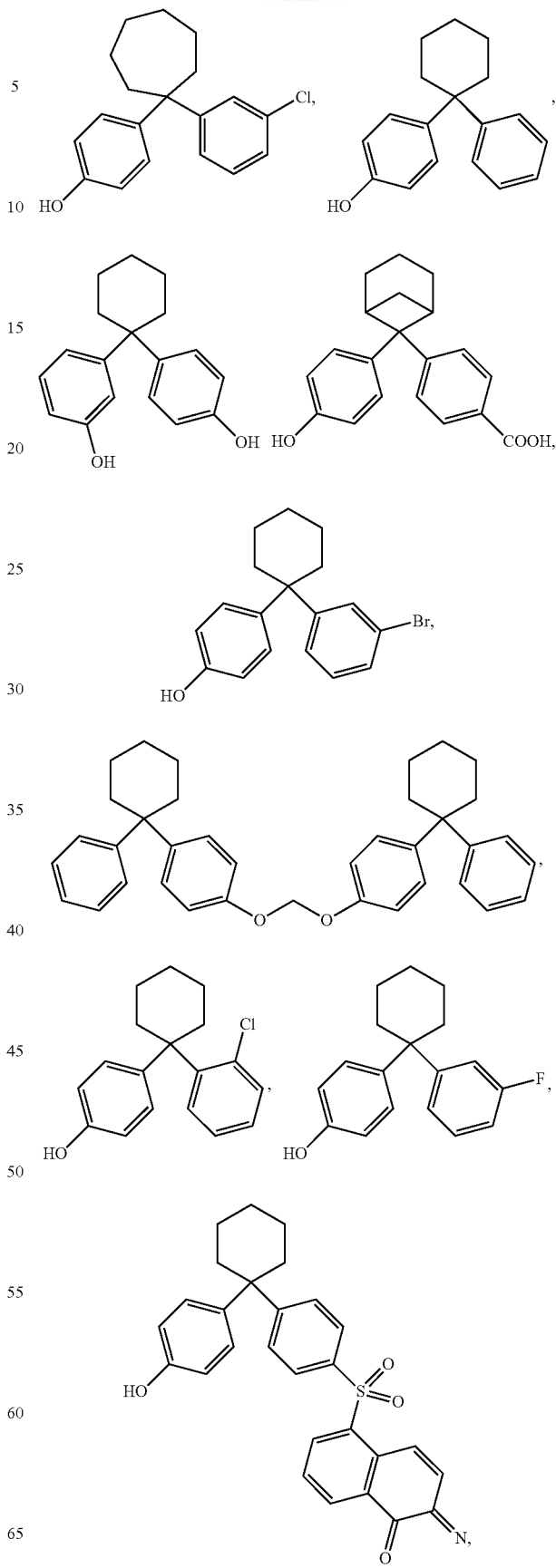

-continued
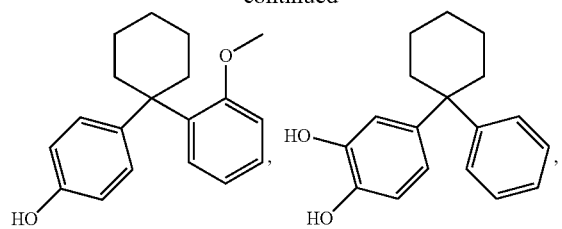
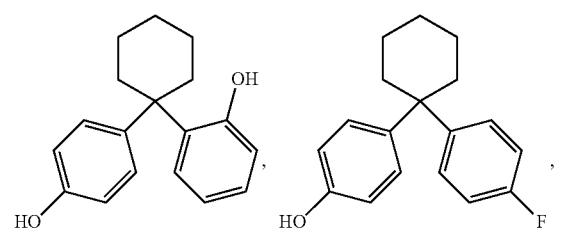
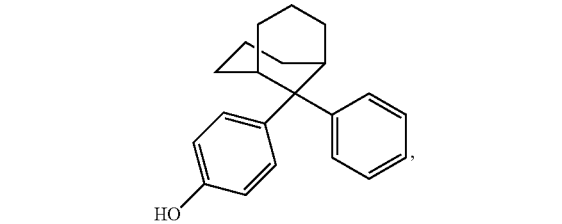
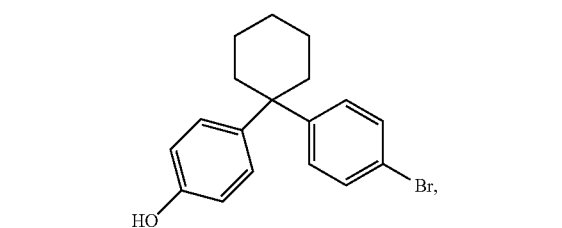
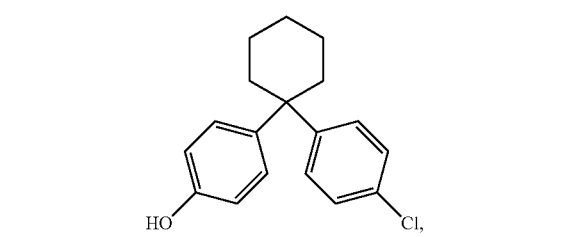
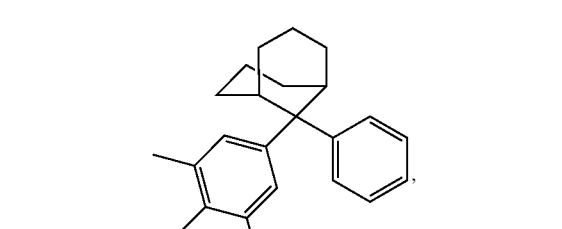
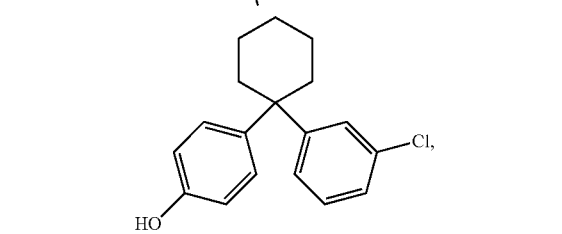
-continued
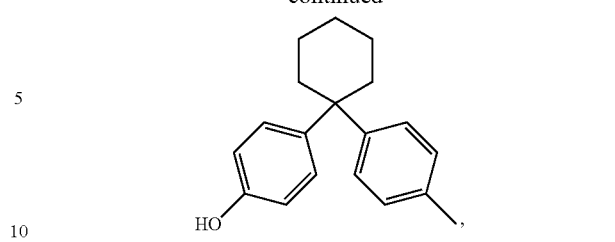
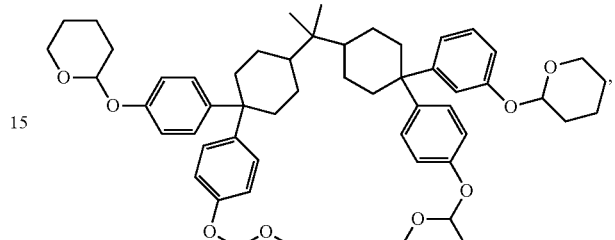
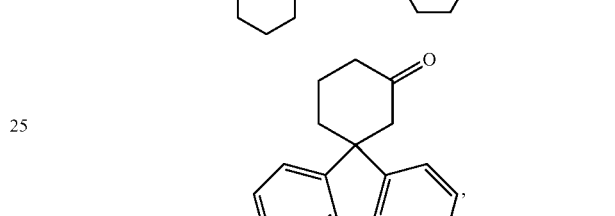
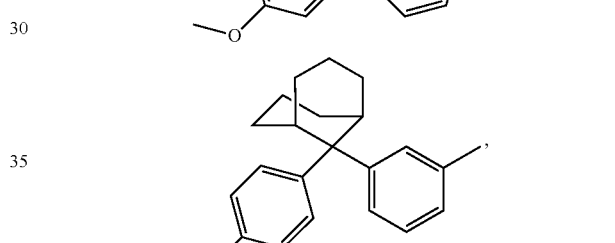
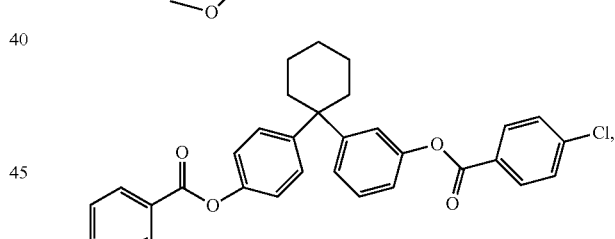
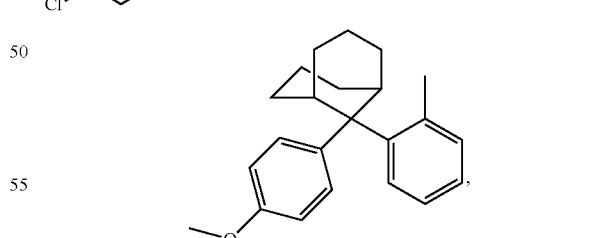
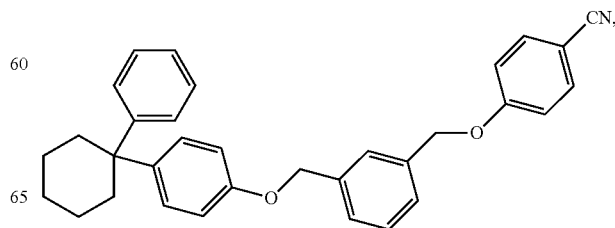

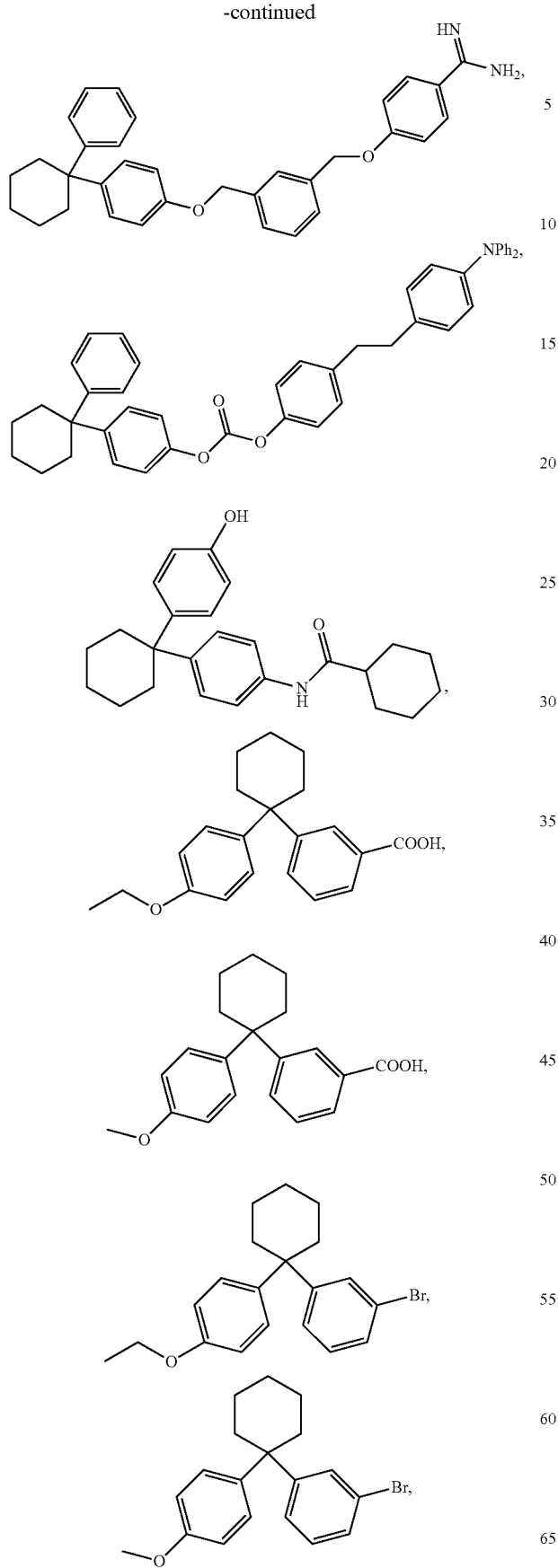
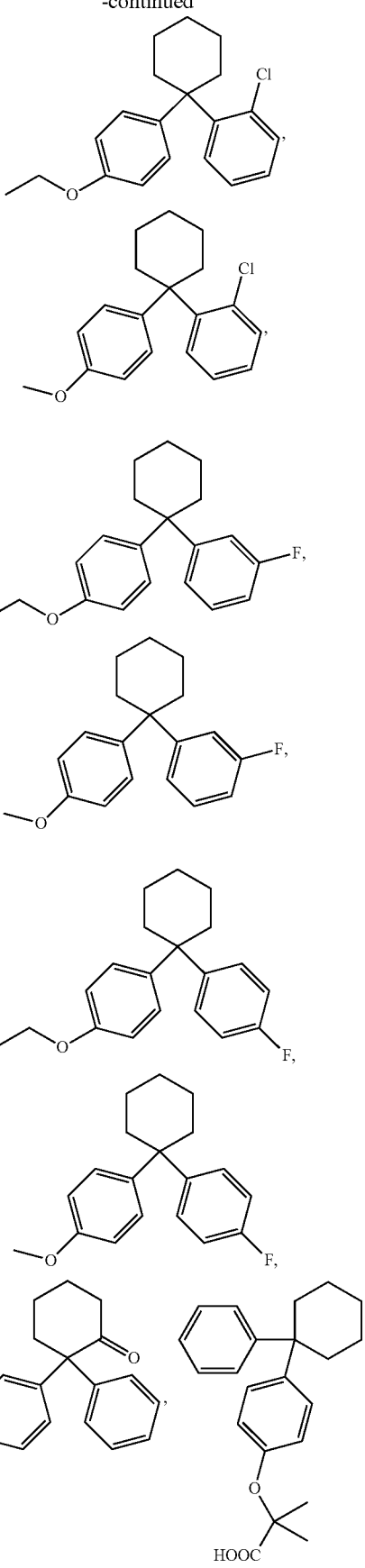

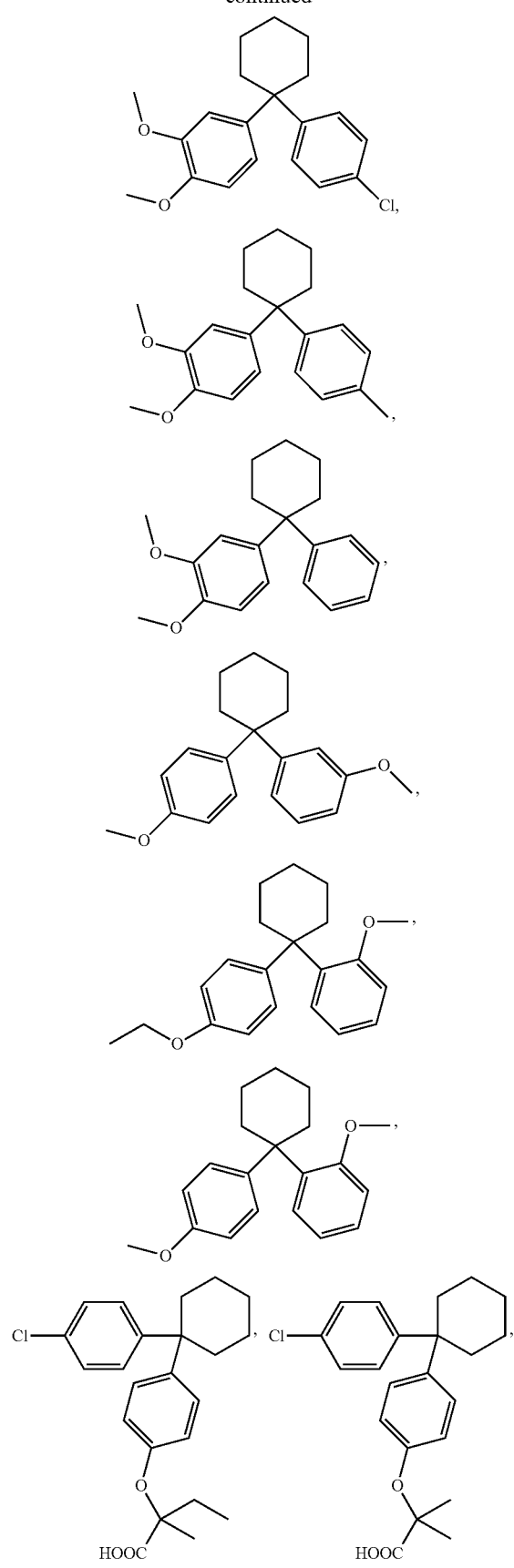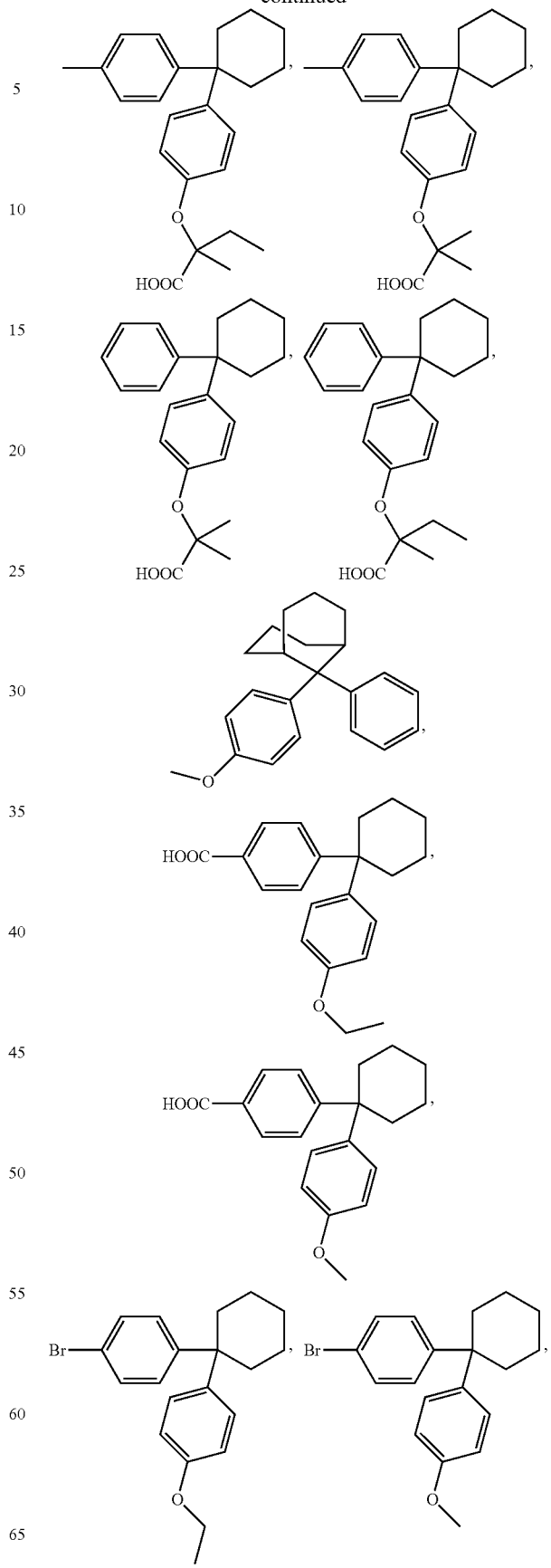

US 8,822,548 B2
33
-continued
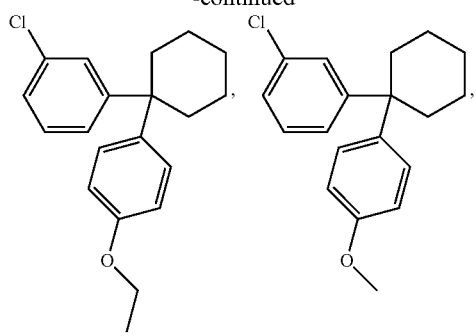
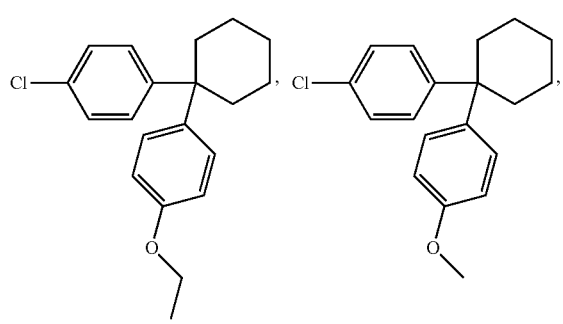
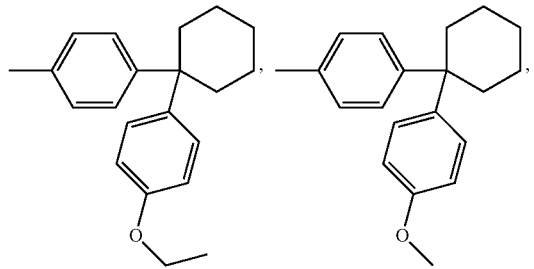
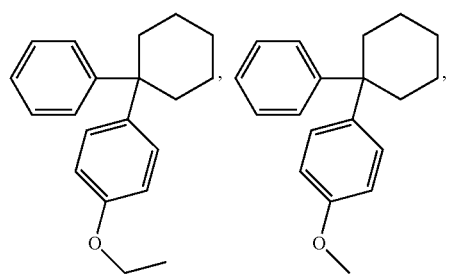
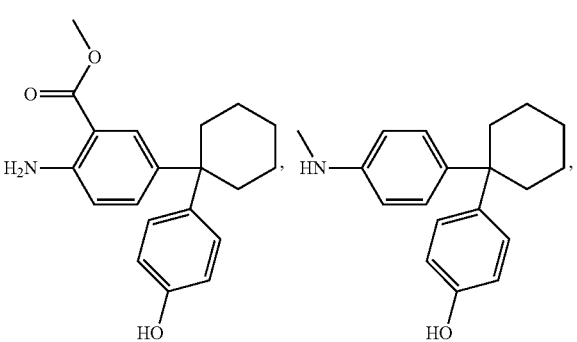
34
-continued
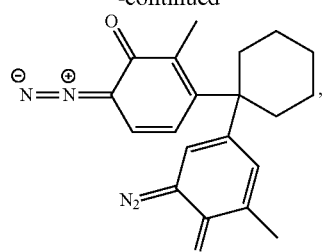
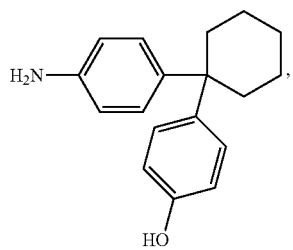
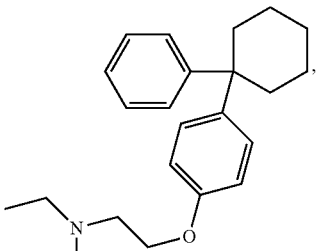
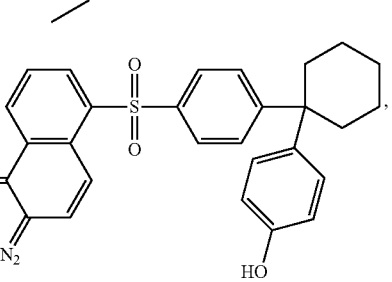
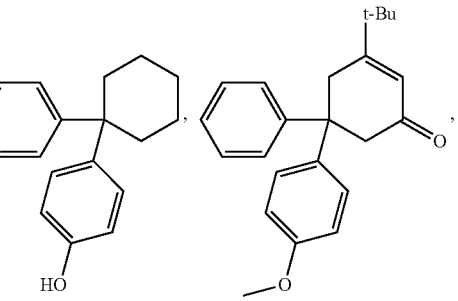
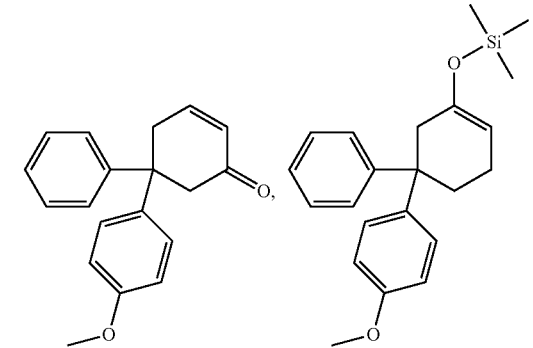

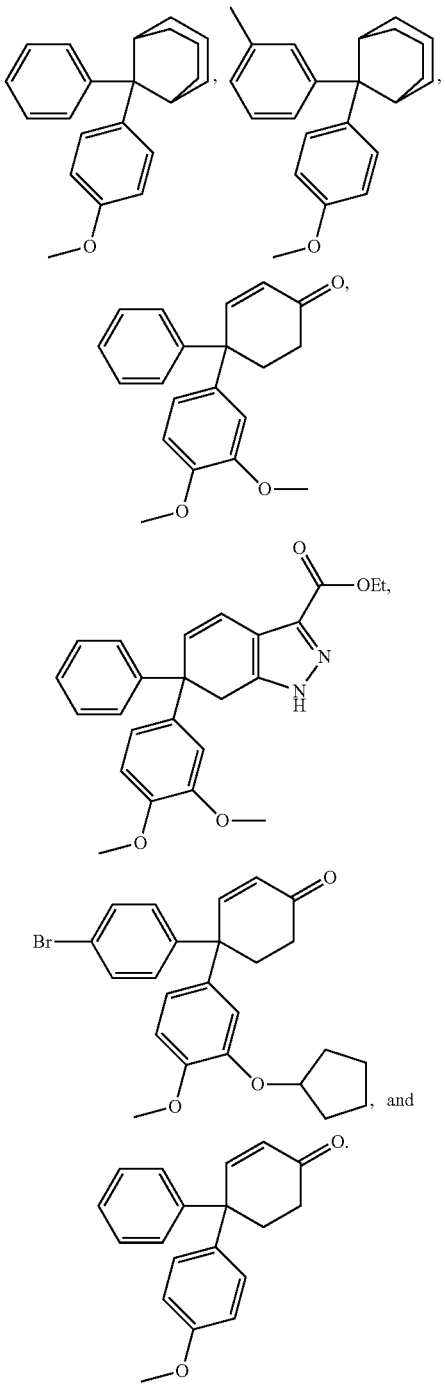

Another embodiment disclosed herein includes a compound of formula II:

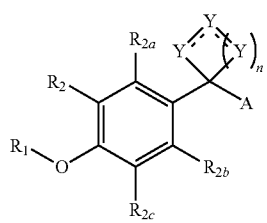

(II)

or a pharmaceutically acceptable salt or prodrug thereof, wherein:

n is an integer selected from the group consisting of 1, 2, 3, 4, 5 and 6;

$R_1$ is selected from the group consisting of hydrogen, $C_1$-$C_8$ straight chained or branched alkyl, $C_1$-$C_8$ straight chained or branched alkenyl, cycloalkyl, cycloalkenyl, substituted or unsubstituted heteroaryl, substituted or unsubstituted aryl, substituted or unsubstituted heteroalicyclyl, sulphonyl, $C_1$-$C_8$ straight chained or branched perhaloalkyl, —C(=Z)R_5, —C(=Z)OR_5, —C(=Z)N(R_5)_2, —S(=O)_2NR_{5a}R_{5b}, —P(=O)(OR_5)_2, and —CH_2C(=O)R_5;

$R_2$, $R_{2a}$, $R_{2b}$, $R_{2c}$, and each $R_6$ are separately selected from the group consisting of hydrogen, alkyl, alkenyl, cycloalkyl, cycloalkenyl, substituted or unsubstituted aryl, substituted or unsubstituted heteroaryl, substituted or unsubstituted heteroalicyclyl, hydroxy, halogen, sulfonyl, perhaloalkyl, —CN, —OR_5, —NR_5R_{5a}, —NR_5NR_{5a}R_{5b}, —NR_5N=CR_{5a}R_{5b}, —N(R_5)C(R_{5a})=NR_{5b}, —C(=Z)R_5, —C(=Z)OR_5, —C(=Z)NR_5R_{5a}, —N(R_5)—C(=Z)R_{5a}, —N(R_5)—C(=Z)NR_{5b}R_{5a}, —OC(=Z)R_5, —N(R_5)—S(=O)_2R_{5a}, and —SR_5;

each Y is separately selected from the group consisting of methylene, methylene substituted with one or two $R_6$ groups, sulphur, oxygen, unsubstituted nitrogen, nitrogen substituted with $R_5$, and C=O;

two Y groups are optionally bound together to form a single bond or a substituted or unsubstituted $C_1$-$C_9$ cycloalkyl or $C_1$-$C_9$ heteroalicyclyl;

$R_{2a}$ is optionally bound to one Y group to form a substituted or unsubstituted $C_4$-$C_9$ heteroalicyclic, $C_4$-$C_9$ cycloalkyl, or $C_4$-$C_9$ cycloalkenyl;

any bond represented by a dashed and solid line represents a bond selected from the group consisting of a single bond and a double bond;

A is selected from the group consisting of substituted heteroaryl, unsubstituted heteroaryl, substituted heteroalicyclyl, unsubstituted heteroalicyclyl, unsubstituted aryl, and substituted aryl;

A is optionally bound to one Y group to form a substituted or unsubstituted $C_4$-$C_9$ heteroalicyclic, $C_4$-$C_9$ cycloalkyl, or $C_4$-$C_9$ cycloalkenyl;

Z is oxygen or sulfur; and each $R_5$, $R_{5a}$ and $R_{5b}$ are separately selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, and substituted or unsubstituted heteroalicyclyl;

provided that when every Y is a substituted or unsubstituted methylene, then A is not a substituted or unsubstituted aryl.

In some embodiments, when A is a substituted aryl, it is not substituted at the para position.

In some embodiments of the compound of formula II, n is an integer selected from the group consisting of 3, 4, and 5; $R_1$ is selected from the group consisting of hydrogen, $C_1$-$C_4$ straight chained or branched alkyl, $C_1$-$C_4$ straight chained or branched alkenyl, $C_1$-$C_4$ straight chained or branched perhaloalkyl, and substituted or unsubstituted aryl; $R_2$, $R_{2a}$, $R_{2b}$, $R_{2c}$ are separately selected from the group consisting of hydrogen, $C_1$-$C_5$ straight chained or branched alkyl, $C_1$-$C_5$ alkenyl, hydroxy, halogen, sulfonyl, perhaloalkyl, —CN, —OR$_5$, —C(=O)R$_5$, —C(=O)OR$_5$, —C(=O)NR$_5$R$_{5a}$, —N(R$_5$)—C(=O)R$_{5a}$, —N(R$_5$)—S(=O)$_2$R$_{5a}$, —OC(=O) R$_5$, and —SR$_5$; each Y is separately selected from the group consisting of substituted or unsubstituted methylene, sulphur, oxygen, substituted or unsubstituted nitrogen or C=O; and A is selected from the group consisting of substituted heteroaryl, unsubstituted heteroaryl, unsubstituted aryl, and substituted aryl that is unsubstituted at the para position.

In some embodiments of the compound of formula II, n is 3; R$_1$ is selected from the group consisting of hydrogen, C$_1$-C$_5$ straight chained or branched alkyl, substituted or unsubstituted aryl; R$_2$, R$_{2a}$, R$_{2b}$, R$_{2c}$ are separately selected from the group consisting of hydrogen, C$_1$-C$_5$ straight chained or branched alkyl, F, Cl, Br, perhaloalkyl, —CN, —OR$_5$, —C(=O), and —SR$_5$; each Y is separately selected from the group consisting of substituted or unsubstituted methylene, oxygen, substituted or unsubstituted nitrogen, or C=O; and A is selected from the group consisting of substituted heteroaryl, unsubstituted heteroaryl, unsubstituted aryl, and substituted aryl that is unsubstituted at the para position.

In some embodiments, the compound of formula II is selected from the group consisting of:

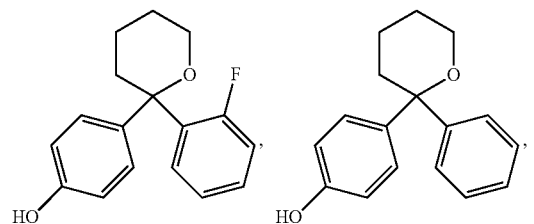

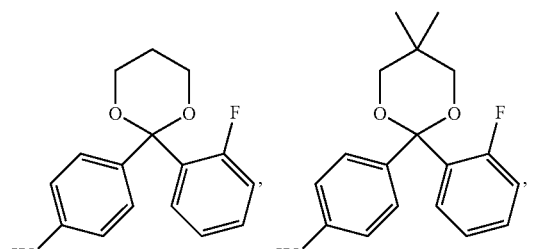

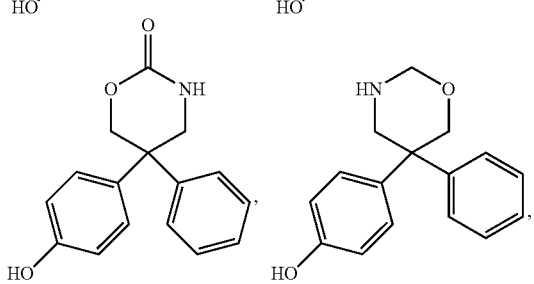

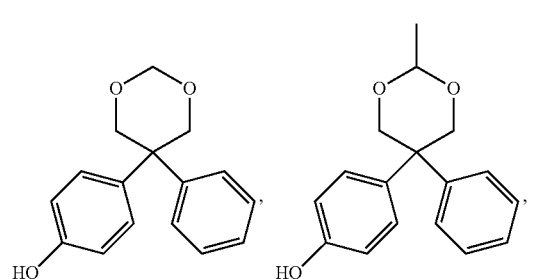

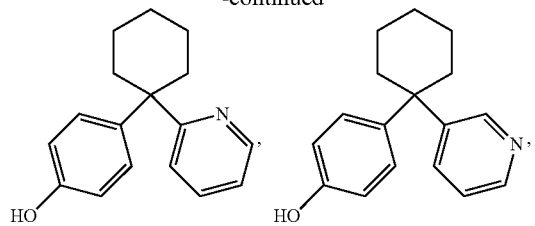

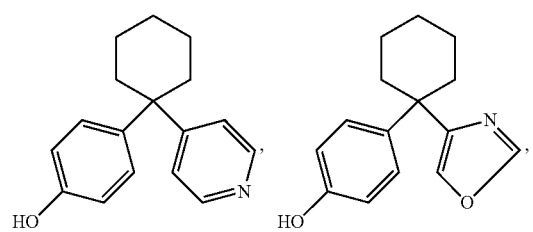

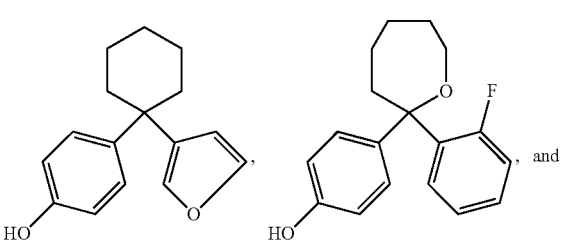

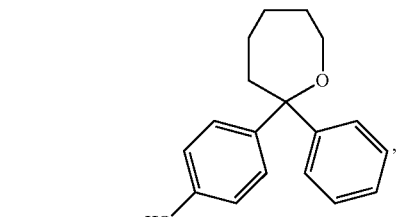

or a pharmaceutically acceptable salt or prodrug thereof.

Another embodiment disclosed herein includes a method of treating or preventing disorders selected from the group consisting of inflammatory bowel syndrome; Crohn's disease; ulcerative proctitis or colitis; prostatic hypertrophy; uterine leiomyomas; breast carcinoma; endometrial carcinoma; polycystic ovary syndrome; endometrial polyps; benign breast disease; adenomyosis; ovarian carcinoma; melanoma; prostate carcinoma; colon carcinoma; brain tumors including glioblastoma, astrocytoma, glioma, or meningioma; prostatitis; interstitial cystitis; bone density loss including osteoporosis or osteopenia; discholesterolemia; dislipidemia; cardiovascular disease; atherosclerosis; hypertension; peripheral vascular disease; restenosis; vasospasm; neurodegenerative disorders including Alzheimer's disease, Huntington's disease, Parkinson's disease or other dementias; spinal cord injuries; cognitive decline; stroke; anxiety; vaginal atrophy; vulvar atrophy; atrophic vaginitis; vaginal dryness; pruritus; dyspareunia; frequent urination; urinary incontinence; urinary tract infections; vasomotor symptoms including flushing or hot flashes; arthritis including rheumatoid arthritis, osteoarthritis, or arthropathiesendometriosis; psoriasis; dermatitis; asthma; pleurisy; multiple sclerosis; systemic lupus erthematosis; uveitis; sepsis; hemmorhagic shock; type II diabetes; acute or chronic inflammation; acute or chronic pain; lung disorders including asthma or chronic obstructive pulmonary disease; ophthalmologic disorders including glaucoma, dry eye, or macular degeneration; and free radical induced disease states; comprising:
    identifying a subject in need of the treating or preventing; and
    administering to the subject a pharmaceutically effective amount of a compound of formula II, or a pharmaceutically acceptable salt or prodrug thereof.

In some embodiments, the disorder is selected from the group consisting of inflammatory bowel syndrome, Crohn's disease, and ulcerative proctitis or colitis.

In some embodiments, the disorder is selected from the group consisting of prostatic hypertrophy, uterine leiomyomas, breast carcinoma, endometrial carcinoma, polycystic ovary syndrome, endometrial polyps, benign breast disease, adenomyosis, ovarian carcinoma, melanoma, prostate carcinoma, colon carcinoma, and brain tumors including glioblastoma, astrocytoma, glioma, or meningioma.

In some embodiments, the disorder is selected from the group consisting of prostatitis and interstitial cystitis.

In some embodiments, the disorder is bone density loss including osteoporosis and osteopenia.

In some embodiments, the disorder is selected from the group consisting of discholesterolemia and dislipidemia.

In some embodiments, the disorder is selected from the group consisting of cardiovascular disease, atherosclerosis, hypertension, peripheral vascular disease, restenosis and vasospasm.

In some embodiments, the disorder is a neurodegenerative disorder including Alzheimer's disease, Huntington's disease, Parkinson's disease or other dementia.

In one embodiment, the disorder is a spinal cord injury.

In some embodiments, the disorder is selected from the group consisting of cognitive decline, stroke, and anxiety.

In some embodiments, the disorder is selected from the group consisting of vaginal atrophy, vulvar atrophy, atrophic vaginitis, vaginal dryness, pruritus, dyspareunia, frequent urination, urinary incontinence, and urinary tract infections.

In some embodiments, the disorder is one or more vasomotor symptoms including flushing or hot flashes.

In some embodiments, the disorder is endometriosis.

In some embodiments, the disorder is arthritis including rheumatoid arthritis, osteoarthritis, or arthropathies.

In some embodiments, the disorder is selected from the group consisting of psoriasis and dermatitis.

In some embodiments, the disorder is selected from the group consisting of asthma and pleurisy.

In some embodiments, the disorder is selected from the group consisting of multiple sclerosis, systemic lupus erthematosis, uveitis, sepsis, and hemmorhagic shock.

In some embodiments, the disorder is type II diabetes.

In some embodiments, the disorder is selected from the group consisting of acute and chronic inflammation.

In some embodiments, the disorder is a lung disorders including asthma or chronic obstructive pulmonary disease.

In some embodiments, the disorder is an ophthalmologic disorders including glaucoma, dry eye, ormacular degeneration.

In some embodiments, the disorder is a free radical induced disease state.

In some embodiments, the disorder is acute or chronic pain. In one embodiment, the pain is neuropathic pain.

Another embodiment disclosed herein includes a method of hormonal replacement therapy, including identifying a subject in need of hormonal replacement and administering to the subject a pharmaceutically effective amount of a compound of formula II, or a pharmaceutically acceptable salt or prodrug thereof.

Another embodiment disclosed herein includes a method of lowering cholesterol, triglycerides, or LDL levels, including identifying a subject in need of the lowering and administering to the subject a pharmaceutically effective amount of a compound of formula II, or a pharmaceutically acceptable salt or prodrug thereof.

Another embodiment disclosed herein includes a method of treating impaired cognition or providing neuroprotection, including identifying a subject in need of the treating or neuroprotection and administering to the subject a pharmaceutically effective amount of a compound of formula II, or a pharmaceutically acceptable salt or prodrug thereof.

Another embodiment disclosed herein includes a method of preventing conception, including administering to a subject a pharmaceutically effective amount of a compound of formula II, or a pharmaceutically acceptable salt or prodrug thereof.

Another embodiment disclosed herein includes a method of modulating or specifically agonizing one or more Estrogen receptors, including identifying a subject in need of the modulating or agonizing and administering to the subject an effective amount of a compound of formula II, or a pharmaceutically acceptable salt or prodrug thereof.

DETAILED DESCRIPTION OF THE PREFERRED EMBODIMENT

Figure 1:
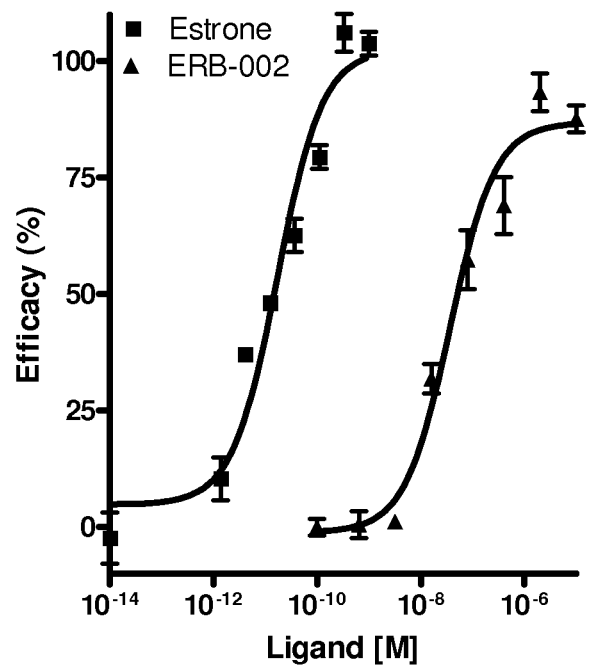
FIG. 1 depicts agonist activity of ERB-002 at the estrogen receptors as evaluated using the Receptor and Selection Amplification (R-SAT) technology.
Figure 1:
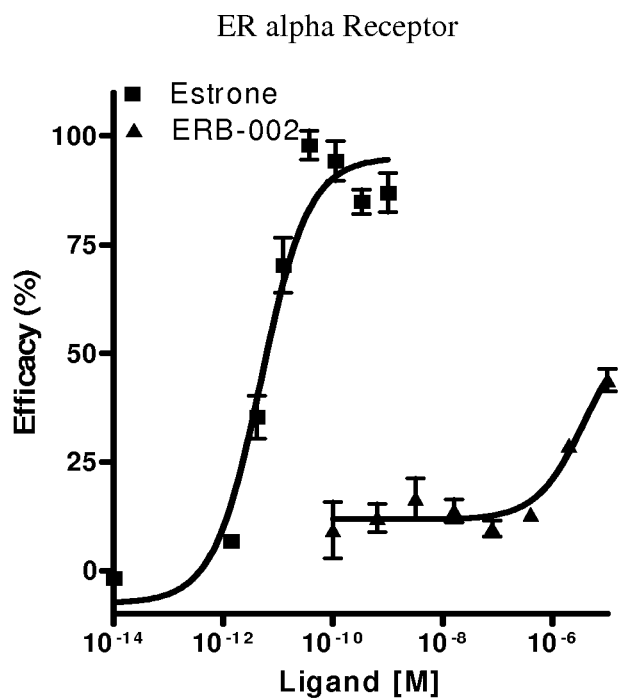

In various embodiments, compounds having the formula (I) and methods for using these compounds for treating disorders related to estrogen receptors are provided:

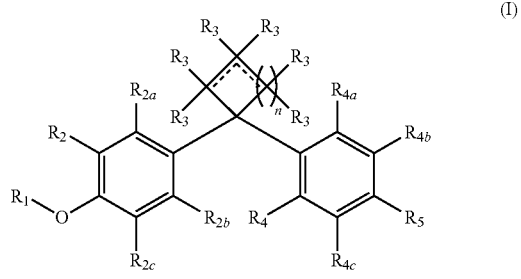

(I)

In some embodiments, pharmaceutically acceptable salt or prodrugs of the compound of formula I are provided. In the compound of formula I:

n is an integer selected from the group consisting of 3, 4, 5 and 6;

$R_1$ is selected from the group consisting of hydrogen, $C_1$-$C_8$ straight chained or branched alkyl, $C_1$-$C_8$ straight chained or branched alkenyl, cycloalkyl, cycloalkenyl, substituted or unsubstituted heteroaryl, substituted or unsubstituted aryl, substituted or unsubstituted heteroalicyclyl, sulphonyl, $C_1$-$C_8$ straight chained or branched perhaloalkyl, —C(=Z)$R_6$, —C(=Z)O$R_6$, —C(=Z)N($R_6$)$_2$, —S(=O)$_2$N$R_{5a}R_{5b}$, —P(=O)(O$R_6$)$_2$, and —CH$_2$C(=O)$R_5$;

$R_2$, $R_{2a}$, $R_{2b}$, $R_{2c}$ are separately selected from the group consisting of hydrogen, alkyl, alkenyl, cycloalkyl, cycloalkenyl, substituted or unsubstituted aryl, substituted or unsubstituted heteroaryl, substituted or unsubstituted heteroalicyclyl, hydroxy, halogen, sulfonyl, perhaloalkyl, —CN, —OR$_6$, —NR$_6$R$_{6a}$, —NR$_6$NR$_{6a}$R$_{6b}$, —NR$_6$N=CR$_{6a}$R$_{6b}$, —N(R$_6$)C(R$_{6a}$)=NR$_{6b}$, —C(=Z)R$_6$, —C(=Z)OR$_6$, —C(=Z)NR$_6$R$_{6a}$, —N(R$_6$)—C(=Z)R$_{6a}$, —N(R$_6$)—C(=Z)NR$_{6b}$R$_{6a}$, —OC(=Z)R$_6$, —N(R$_6$)—S(=O)$_2$R$_{6a}$, and —SR$_6$;

each R$_3$ is separately selected from the group consisting of hydrogen, alkyl, alkenyl, cycloalkyl, cycloalkenyl, substituted or unsubstituted aryl, substituted or unsubstituted heteroaryl, substituted or unsubstituted heteroalicyclyl, hydroxy, halogen, sulfonyl, perhaloalkyl, —CN, =O, and —OR$_6$, or are separately absent to accommodate a double bond;

two R$_3$ groups are optionally bound together to form a substituted or unsubstituted C$_3$-C$_9$ cycloalkyl or C$_3$-C$_9$ heteroalicyclyl;

R$_{2a}$ is optionally bound to one R$_3$ group to form a substituted or unsubstituted C$_4$-C$_9$ heteroalicyclic, C$_4$-C$_9$ cycloalkyl, or C$_4$-C$_9$ cycloalkenyl;

R$_{4a}$ is optionally bound to one R$_3$ group to form a substituted or unsubstituted C$_4$-C$_9$ heteroalicyclic, C$_4$-C$_9$ cycloalkyl, or C$_4$-C$_9$ cycloalkenyl;

any bond represented by a dashed and solid line represents a bond selected from the group consisting of a single bond and a double bond;

R$_4$, R$_{4a}$, R$_{4b}$, R$_{4c}$ are separately selected from the group consisting of hydrogen, alkyl, alkenyl, cycloalkyl, cycloalkenyl, substituted or unsubstituted aryl, substituted or unsubstituted heteroaryl, substituted or unsubstituted heteroalicyclyl, hydroxy, nitro, halogen, sulfonyl, perhaloalkyl, —OR$_6$, —NR$_6$R$_{6a}$, —NR$_6$NR$_{6a}$R$_{6b}$, —NR$_6$N=CR$_{6a}$R$_{6b}$, —N(R$_6$)C(R$_{6a}$)=NR$_{6b}$, —CN, —C(=Z)R$_6$, —C(=Z)OR$_6$, —C(=Z)NR$_6$R$_{6a}$, —S(=Z)NR$_6$R$_{6a}$, —N(R$_6$)—C(=Z)R$_{6a}$, —N(R$_6$)—C(=Z)NR$_{6b}$R$_{6a}$, —OC(=Z)R$_6$, —N(R$_6$)—S(=O)$_2$R$_{6a}$, and —SR$_6$;

R$_{4a}$ and R$_{4b}$ are optionally bound together to form an aryl, heteroaryl, or heteroalicyclyl;

R$_5$ is selected from the group consisting of hydrogen, alkyl, alkenyl, cycloalkyl, cycloalkenyl, halogen, —CN, —SR$_6$, sulfonyl, —C(=O)NR$_6$R$_{6a}$, —C(=O)R$_6$, —NR$_6$R$_{6a}$, —COOR$_6$, and perhaloalkyl;

Z is oxygen or sulfur; and

R$_6$, R$_{6a}$ and R$_{6b}$ are separately selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, and substituted or unsubstituted heteroalicyclyl.

In some embodiments, compounds are provided according to formula I but excluding the compounds selected from the group consisting of:

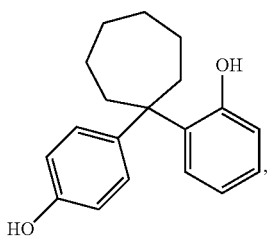

-continued

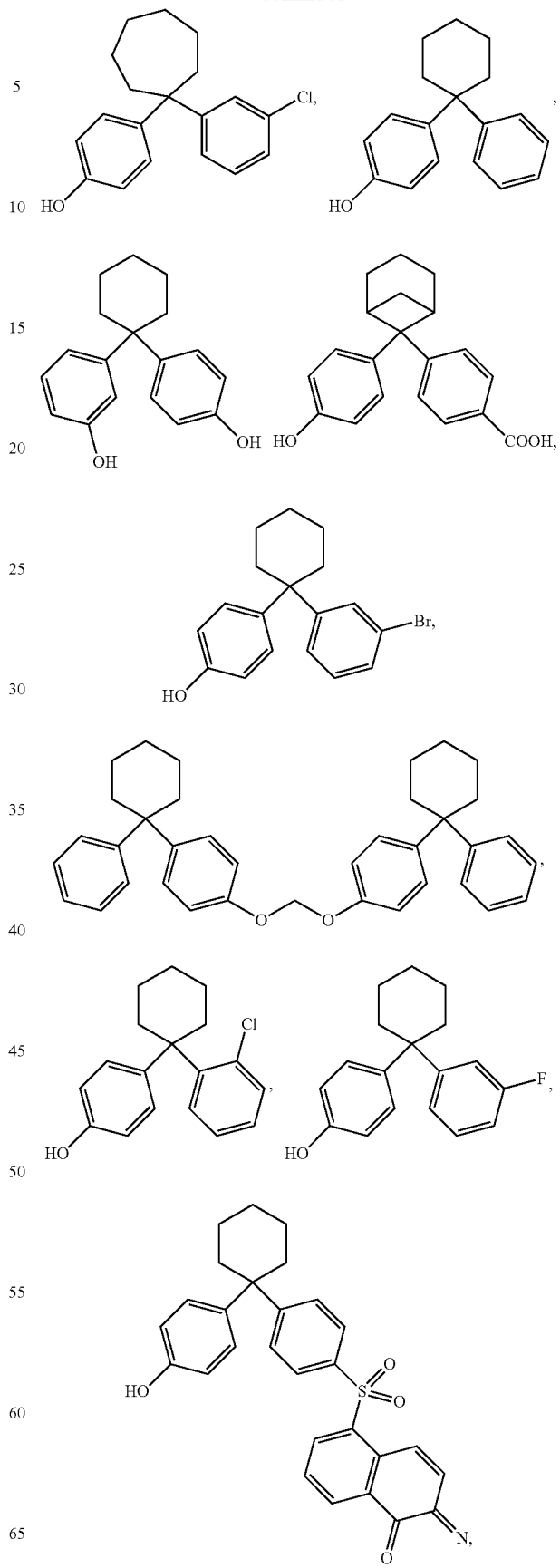

-continued
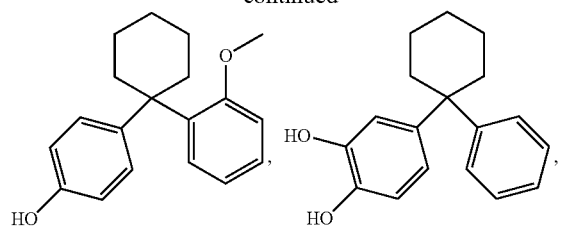
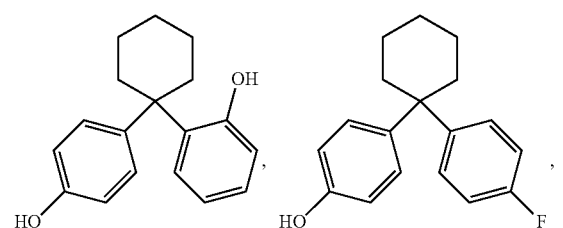
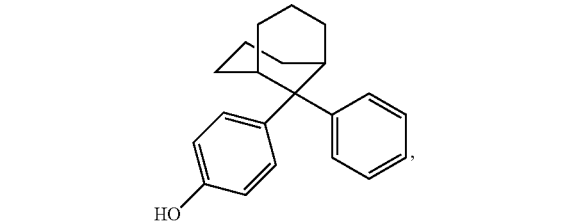
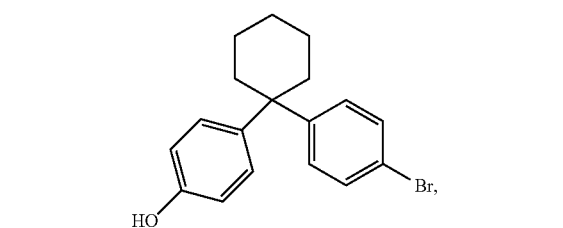
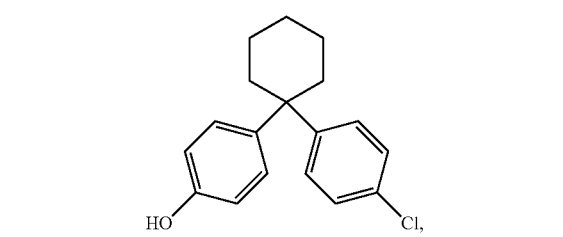
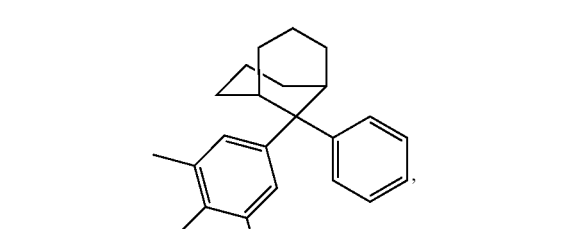
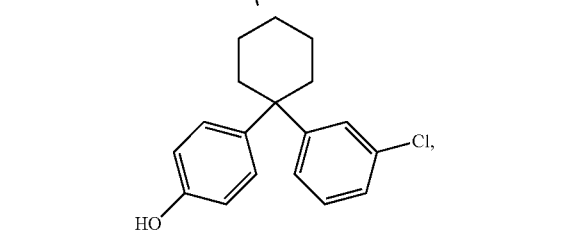
-continued
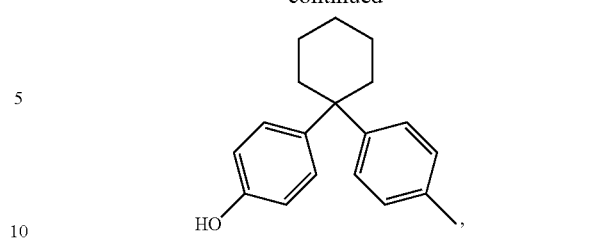
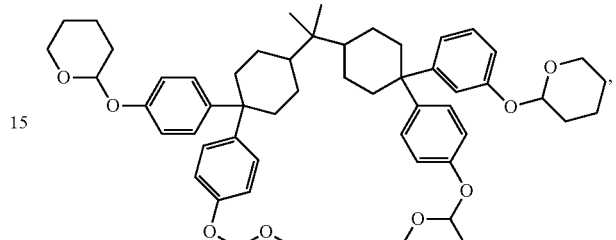
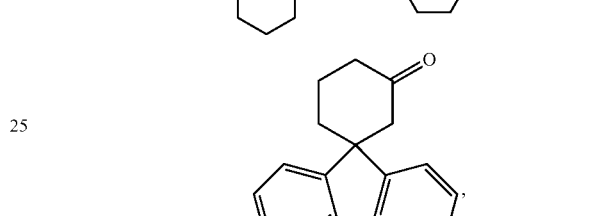
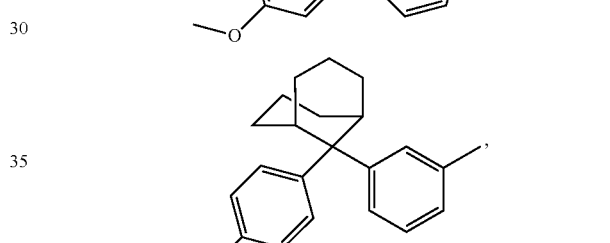
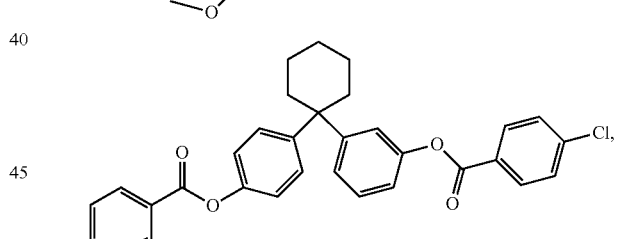
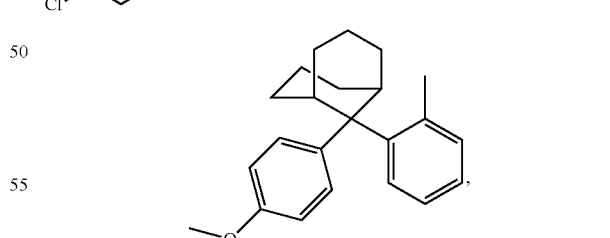
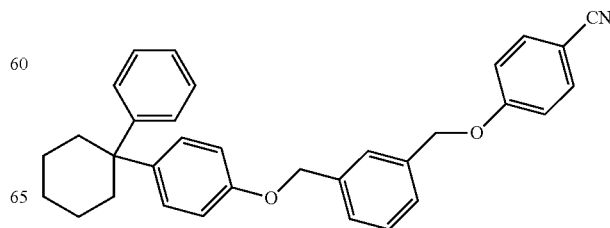

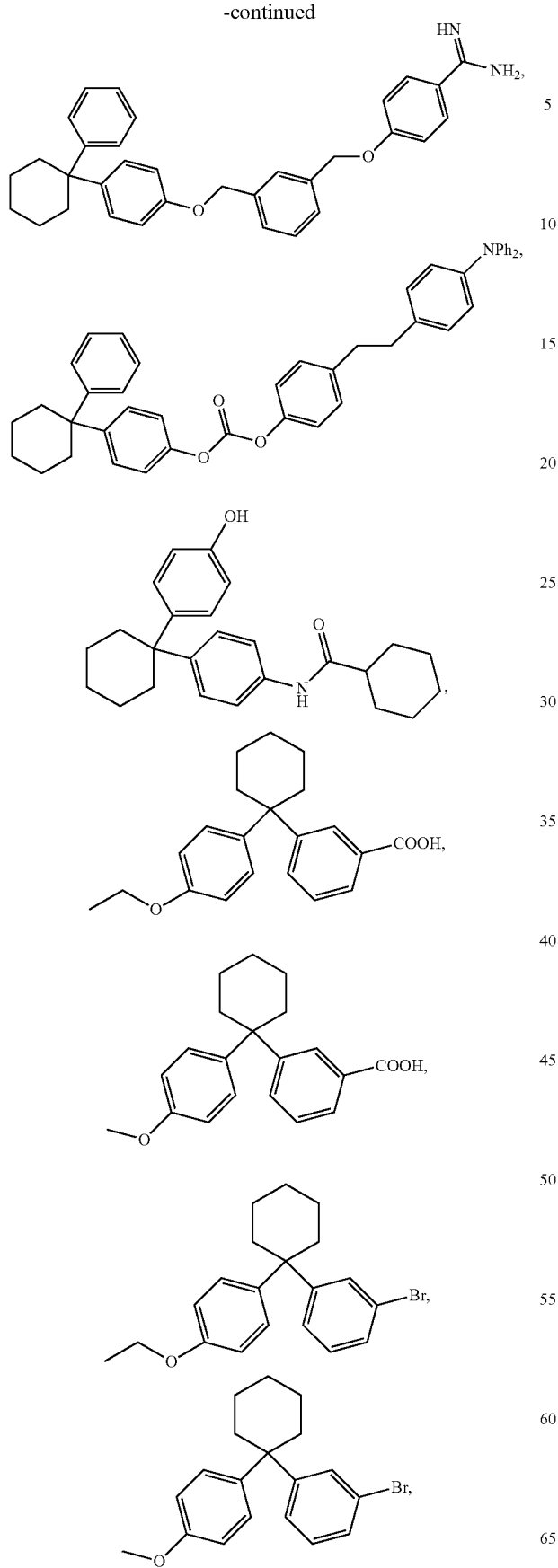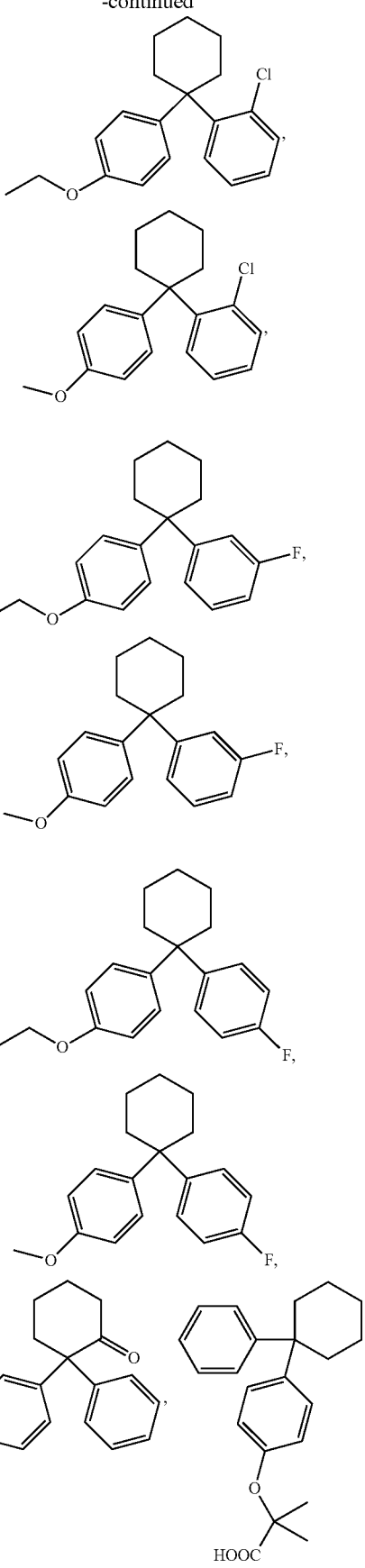

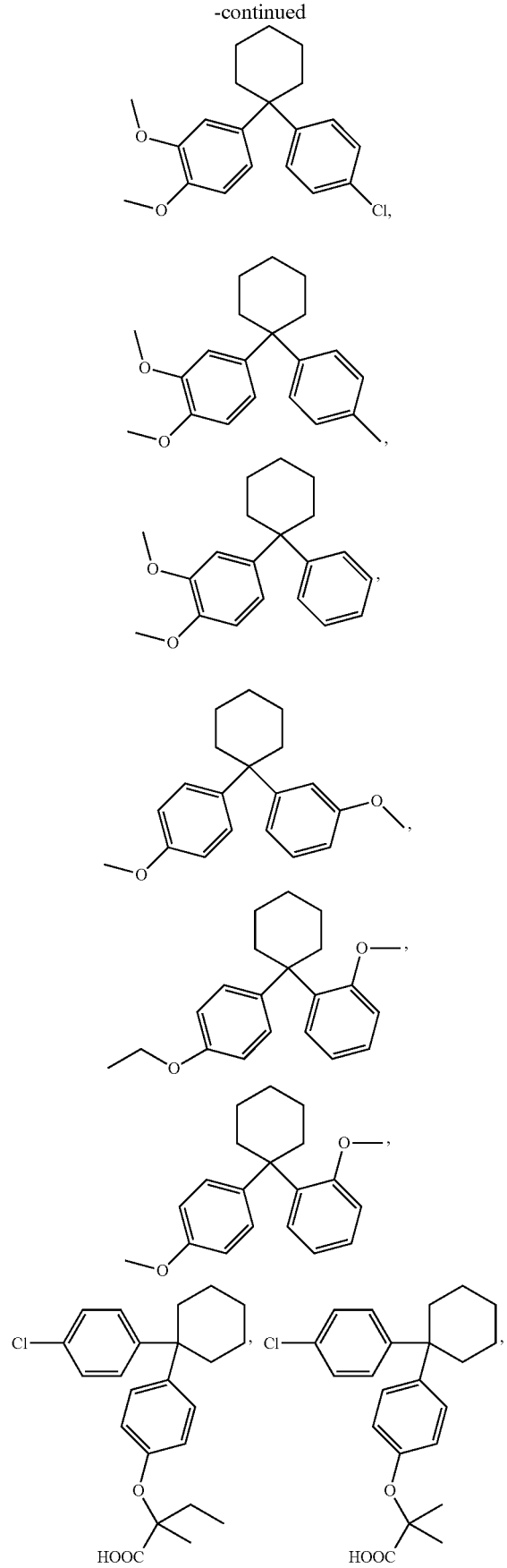
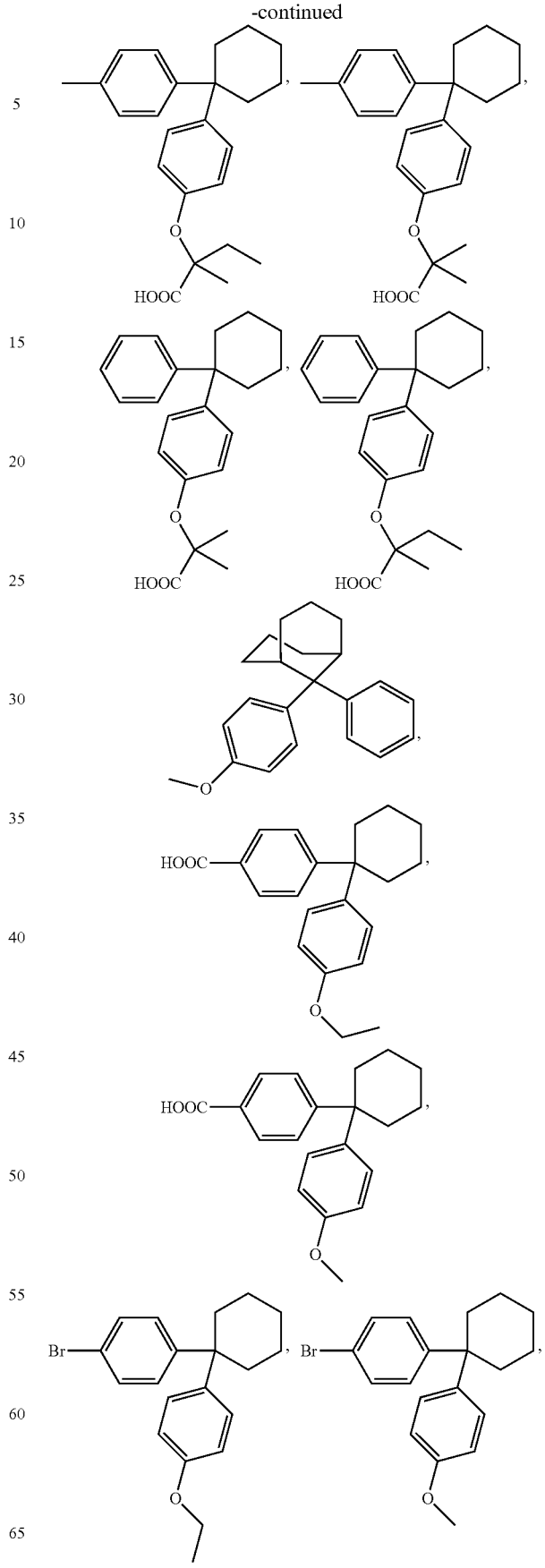

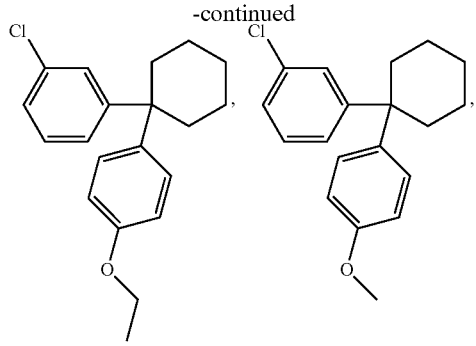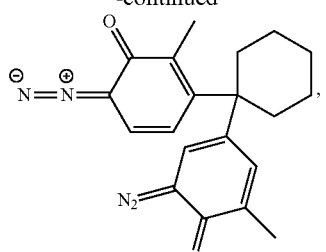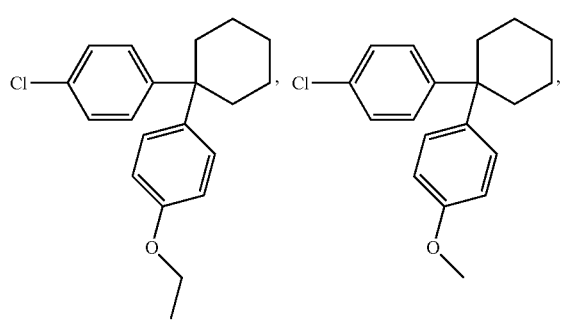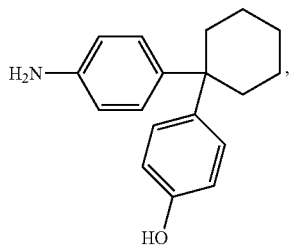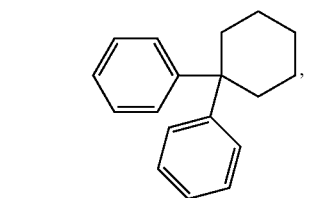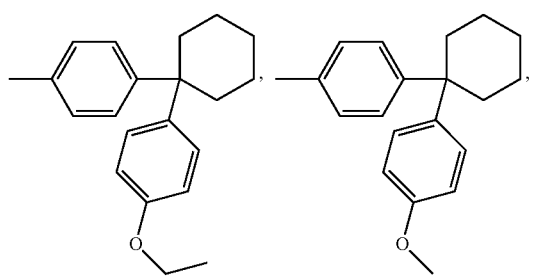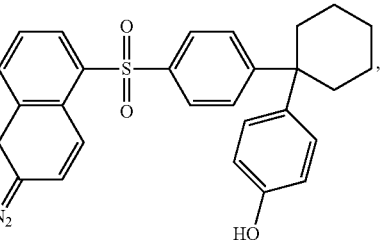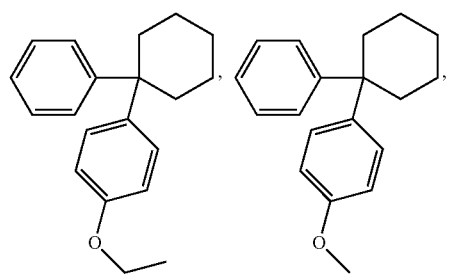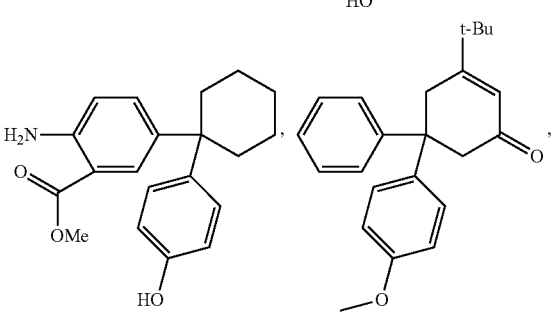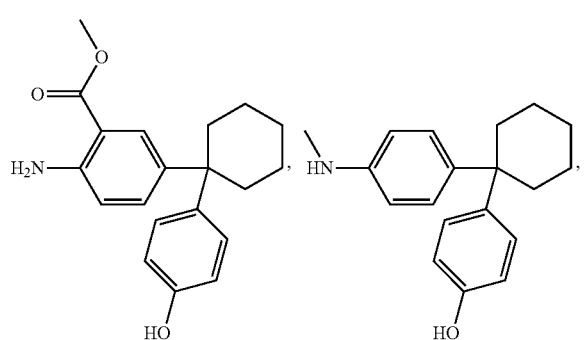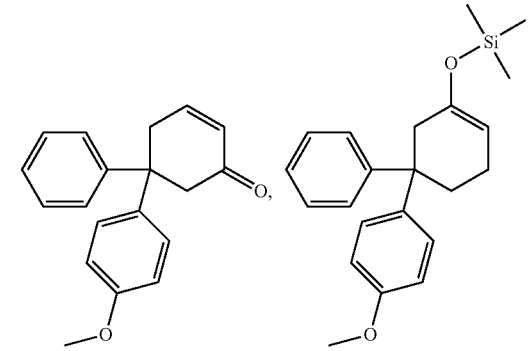

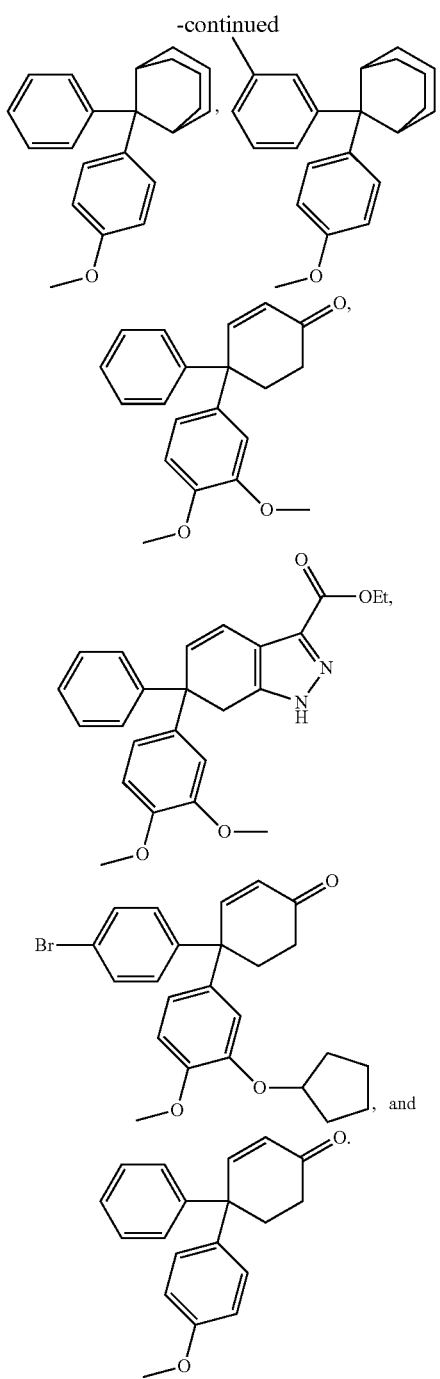

In some embodiments of the compound of formula I:

n is an integer selected from the group consisting of 3, 4, and 5;

$R_1$ is selected from the group consisting of hydrogen, $C_1$-$C_4$ straight chained or branched alkyl, $C_1$-$C_4$ straight chained or branched alkenyl, $C_1$-$C_4$ straight chained or branched perhaloalkyl, and substituted or unsubstituted aryl;

$R_2$, $R_{2a}$, $R_{2b}$, $R_{2c}$ are separately selected from the group consisting of hydrogen, $C_1$-$C_5$ straight chained or branched alkyl, $C_1$-$C_5$ alkenyl, hydroxy, halogen, sulfonyl, perhaloalkyl, —CN, —$OR_6$, —C(=O)$R_6$, —C(=O)$OR_6$, —C(=O)$NR_6R_{6a}$, —N($R_6$)—C(=O)$R_{6a}$, —N($R_6$)—S(=O)$_2R_{6a}$, —OC(=O)$R_6$, and —$SR_6$;

each $R_3$ is separately selected from the group consisting of hydrogen, $C_1$-$C_5$ straight chained or branched alkyl, $C_1$-$C_5$ alkenyl, cycloalkyl, cycloalkenyl, hydroxy, halogen, sulfonyl, perhaloalkyl, —CN, =O, and —$OR_6$, or each $R_3$ is separately absent to accommodate a double bond;

$R_4$, $R_{4a}$, $R_{4b}$, $R_{4c}$ are separately selected from the group consisting hydrogen, $C_1$-$C_5$ straight chained or branched alkyl, $C_1$-$C_5$ alkenyl, hydroxy, halogen, sulfonyl, perhaloalkyl, —$OR_6$, —CN, —C(=O)$R_6$, —C(=O)$OR_6$, —C(=O)$NR_6R_{6a}$, —S(=O)$_2NR_6R_{6a}$, —N($R_6$)—C(=O)$R_{6a}$, —OC(=Z)$R_6$, —N($R_6$)—S(=O)$_2R_{6a}$, and —$SR_6$; and $R_5$ is selected from the group consisting of hydrogen, $C_1$-$C_5$ straight chained or branched alkyl, halogen, —CN, —$SR_6$, sulfonyl, —$OCF_3$, and perhaloalkyl.

In other embodiments of the compound of formula I:

n is 3;

$R_1$ is selected from the group consisting of hydrogen, $C_1$-$C_5$ straight chained or branched alkyl, substituted or unsubstituted aryl;

$R_2$, $R_{2a}$, $R_{2b}$, $R_{2c}$ are separately selected from the group consisting of hydrogen, $C_1$-$C_5$ straight chained or branched alkyl, F, Cl, Br, perhaloalkyl, —CN, —$OR_6$, —C(=O), and —$SR_6$;

each $R_3$ is separately selected from the group consisting of hydrogen, $C_1$-$C_5$ straight chained or branched alkyl, $C_1$-$C_5$ alkenyl, cycloalkyl, halogen, perhaloalkyl, —CN, and —$OR_6$, or each $R_3$ is separately absent to accommodate a double bond;

each $R_4$, $R_{4a}$, $R_{4b}$, $R_{4c}$ is separately selected from the group consisting hydrogen, $C_1$-$C_5$ straight chained or branched alkyl, halogen, sulfonyl, perhaloalkyl, —$OR_6$, —CN, —N($R_6$)—S(=O)$_2R_{6a}$, and —$SR_6$; and $R_5$ is selected from the group consisting of hydrogen, $C_1$-$C_5$ straight chained or branched alkyl, F, Cl, —CN, —$SR_6$, —$OCF_3$, and $CF_3$.

In some embodiments, the compound of formula I is selected from the group consisting of:

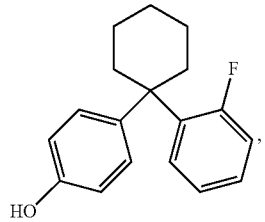

ERB-003

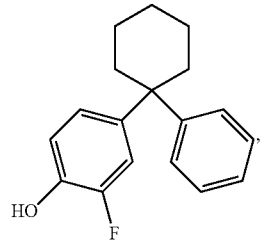

ERB-006

-continued
ERB-007
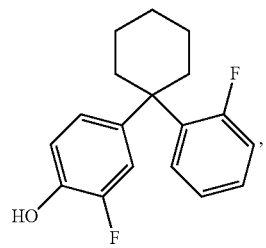
ERB-008
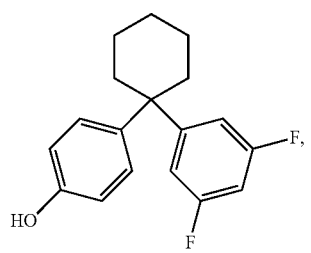
ERB-009
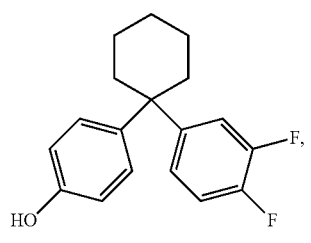
ERB-010
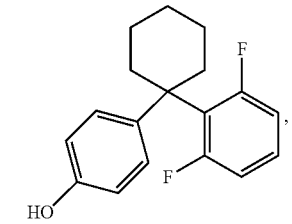
ERB-011
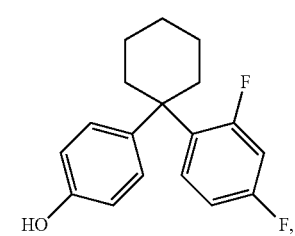
ERB-012
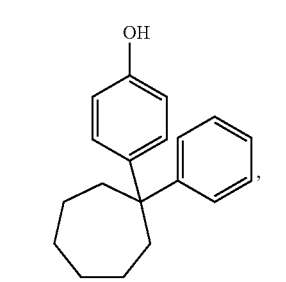
-continued
ERB-013
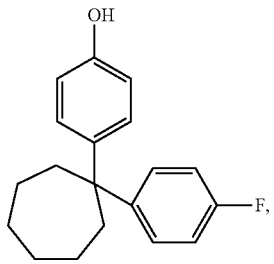
ERB-014
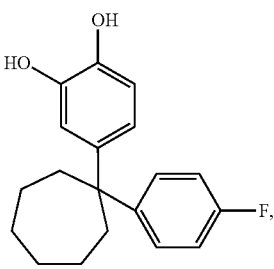
ERB-015
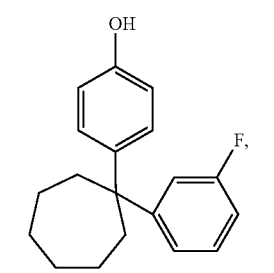
ERB-016
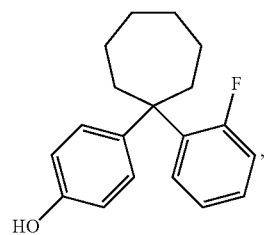
ERB-017
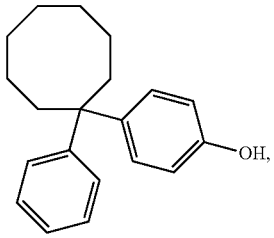
ERB-026
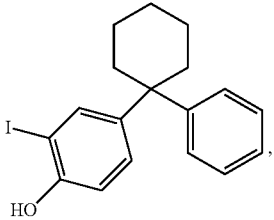

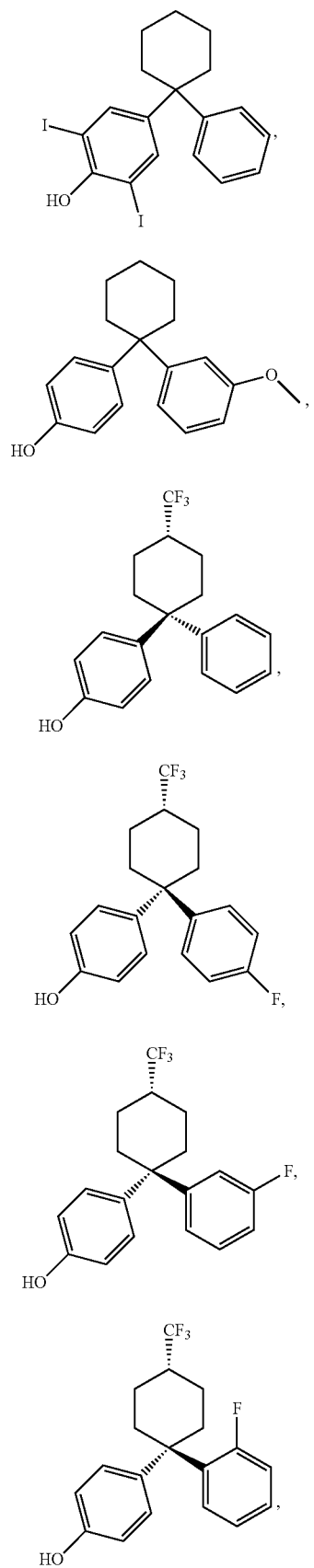
ERB-027
ERB-029
ERB-030
ERB-031
ERB-032
ERB-033
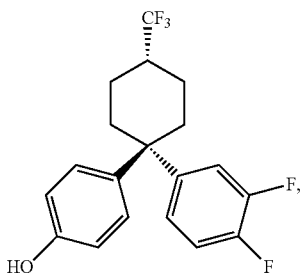
ERB-034
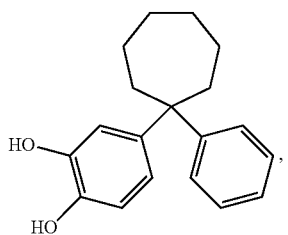
ERB-035
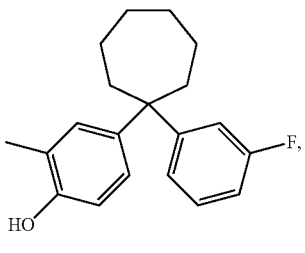
ERB-036
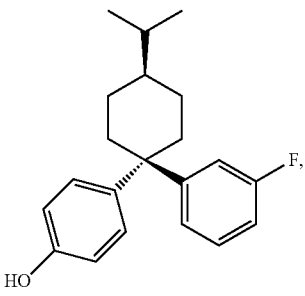
ERB-037
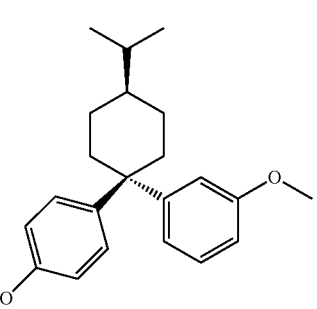
ERB-038
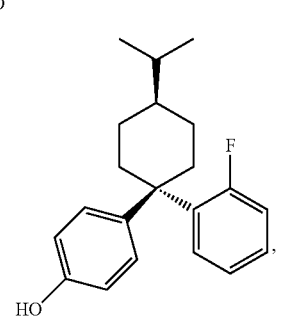
ERB-039

-continued

ERB-040
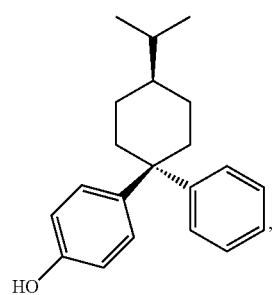

ERB-041
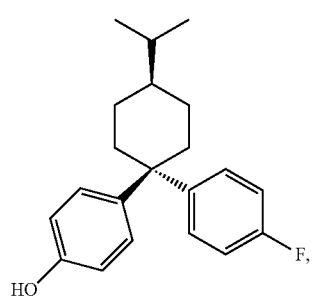

ERB-043
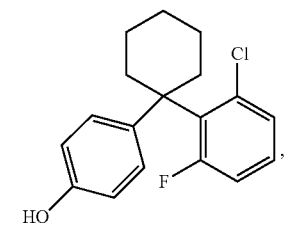

ERB-044
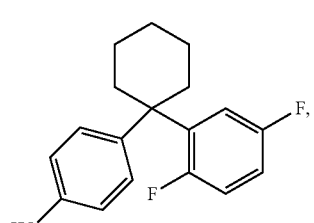

ERB-045
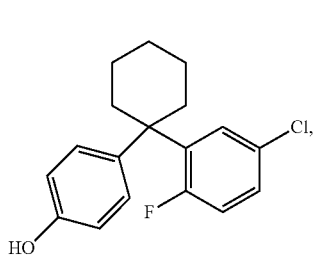

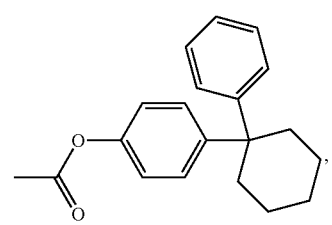

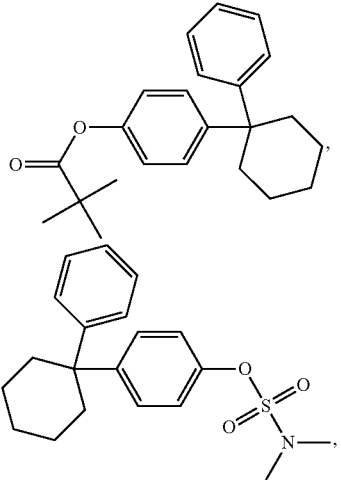

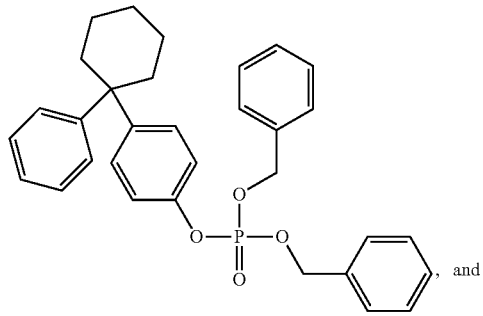

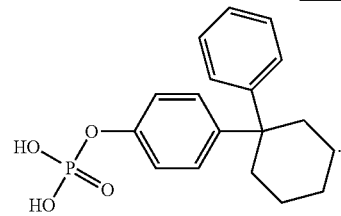

, and

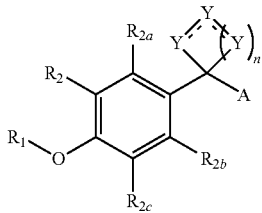

In various other embodiments, compounds having the formula (II) and methods for using these compounds for treating disorders related to estrogen receptors are provided:

(II)

$$\text{structure with } R_1\text{-O-, } R_2, R_{2a}, R_{2b}, R_{2c}, Y, A, n$$

In some embodiments, pharmaceutically acceptable salts or prodrugs of the compound of formula II are provided. In the compound of formula II:

n is an integer selected from the group consisting of 1, 2, 3, 4, 5 and 6;

$R_1$ is selected from the group consisting of hydrogen, $C_1$-$C_8$ straight chained or branched alkyl, $C_1$-$C_8$ straight chained or branched alkenyl, cycloalkyl, cycloalkenyl, substituted or unsubstituted heteroaryl, substituted or unsubstituted aryl, substituted or unsubstituted heteroalicyclyl, sulphonyl, $C_1$-$C_8$ straight chained or branched perhaloalkyl, —C(=Z)R$_5$, —C(=Z)OR$_5$, —C(=Z)N(R$_5$)$_2$, —S(=O)$_2$NR$_{5a}$R$_{5b}$, —P(=O)(OR$_5$)$_2$, and —CH$_2$C(=O)R$_5$;

R$_2$, R$_{2a}$, R$_{2b}$, R$_{2c}$, and each R$_6$ are separately selected from the group consisting of hydrogen, alkyl, alkenyl, cycloalkyl, cycloalkenyl, substituted or unsubstituted aryl, substituted or unsubstituted heteroaryl, substituted or unsubstituted heteroalicyclyl, hydroxy, halogen, sulfonyl, perhaloalkyl, —CN, —OR$_5$, —NR$_5$R$_{5a}$, —NR$_5$NR$_{5a}$R$_{5b}$, —NR$_5$N=CR$_{5a}$R$_{5b}$, —N(R$_5$)C(R$_{5a}$)=NR$_{5b}$, —C(=Z)R$_5$, —C(=Z)OR$_5$, —C(=Z)NR$_5$R$_{5a}$, —N(R$_5$)—C(=Z)R$_{5a}$, —N(R$_5$)—C(=Z)NR$_{5b}$R$_{5a}$, —OC(=Z)R$_5$, —N(R$_5$)—S(=O)$_2$R$_{5a}$, and —SR$_5$;

each Y is separately selected from the group consisting of methylene, methylene substituted with one or two R$_6$ groups, sulphur, oxygen, unsubstituted nitrogen, nitrogen substituted with R$_5$, and C=O;

two Y groups are optionally bound together to form a single bond or a substituted or unsubstituted C$_1$-C$_9$ cycloalkyl or C$_1$-C$_9$ heteroalicyclyl;

R$_{2a}$ is optionally bound to one Y group to form a substituted or unsubstituted C$_4$-C$_9$ heteroalicyclic, C$_4$-C$_9$ cycloalkyl, or C$_4$-C$_9$ cycloalkenyl;

any bond represented by a dashed and solid line represents a bond selected from the group consisting of a single bond and a double bond;

A is selected from the group consisting of substituted heteroaryl, unsubstituted heteroaryl, substituted heteroalicyclyl, unsubstituted heteroalicyclyl, unsubstituted aryl, and substituted aryl;

A is optionally bound to one Y group to form a substituted or unsubstituted C$_4$-C$_9$ heteroalicyclic, C$_4$-C$_9$ cycloalkyl, or C$_4$-C$_9$ cycloalkenyl;

Z is oxygen or sulfur; and each R$_5$, R$_{5a}$ and R$_{5b}$ are separately selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, and substituted or unsubstituted heteroalicyclyl;

provided that when every Y is a substituted or unsubstituted methylene, then A is not a substituted or unsubstituted aryl.

In some embodiments, when A is a substituted aryl, it is not substituted at the para position.

In one embodiment of the compound of formula II, n is an integer selected from the group consisting of 3, 4, and 5; R$_1$ is selected from the group consisting of hydrogen, C$_1$-C$_4$ straight chained or branched alkyl, C$_1$-C$_4$ straight chained or branched alkenyl, C$_1$-C$_4$ straight chained or branched perhaloalkyl, and substituted or unsubstituted aryl; R$_2$, R$_{2a}$, R$_{2b}$, R$_{2c}$ are separately selected from the group consisting of hydrogen, C$_1$-C$_5$ straight chained or branched alkyl, C$_1$-C$_5$ alkenyl, hydroxy, halogen, sulfonyl, perhaloalkyl, —CN, —OR$_5$, —C(=O)R$_5$, —C(=O)OR$_5$, —C(=O)NR$_5$R$_{5a}$, —N(R$_5$)—C(=O)R$_{5a}$, —N(R$_5$)—S(=O)$_2$R$_{5a}$, —OC(=O)R$_5$, and —SR$_5$; each Y is separately selected from the group consisting of substituted or unsubstituted methylene, sulphur, oxygen, substituted or unsubstituted nitrogen or C=O; and A is selected from the group consisting of substituted heteroaryl, unsubstituted heteroaryl, unsubstituted aryl, and substituted aryl that is unsubstituted at the para position.

In another embodiment of the compound of formula II, n is 3; R$_1$ is selected from the group consisting of hydrogen, C$_1$-C$_5$ straight chained or branched alkyl, substituted or unsubstituted aryl; R$_2$, R$_{2a}$, R$_{2b}$, R$_{2c}$ are separately selected from the group consisting of hydrogen, C$_1$-C$_5$ straight chained or branched alkyl, F, Cl, Br, perhaloalkyl, —CN, —OR$_5$, —C(=O), and —SR$_5$; each Y is separately selected from the group consisting of substituted or unsubstituted methylene, oxygen, substituted or unsubstituted nitrogen, or C=O; and A is selected from the group consisting of substituted heteroaryl, unsubstituted heteroaryl, unsubstituted aryl, and substituted aryl that is unsubstituted at the para position.

In various embodiments, the compound of formula II is selected from the group consisting of:

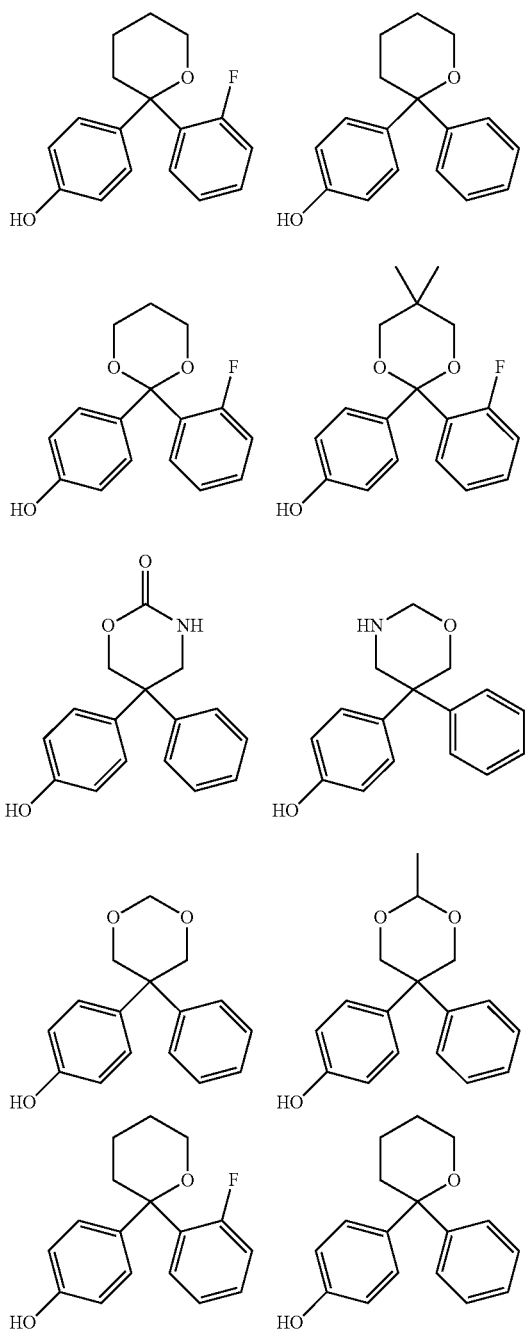

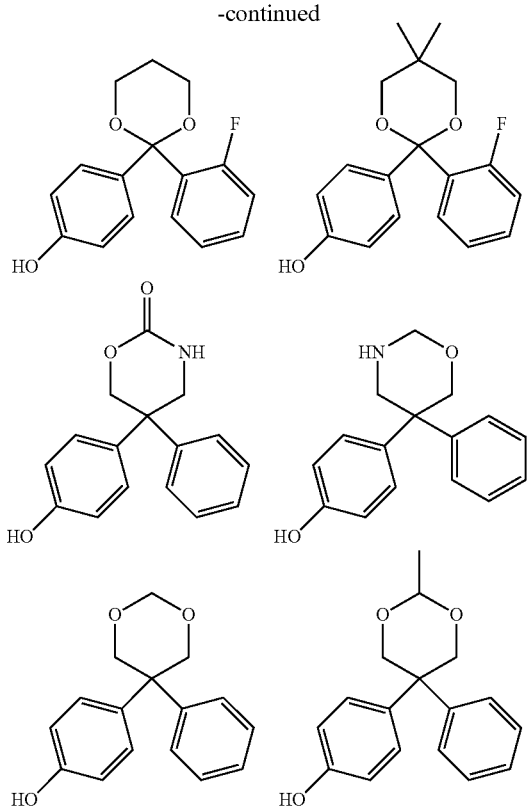

or a pharmaceutically acceptable salt or prodrug thereof.

Definitions

Unless otherwise specified, "R" group(s) such as, without limitation, R, $R^a$ and $R^b$, is(are) independently selected from the group consisting of hydrogen, alkyl, alkenyl, alkynyl, cycloalkyl, aryl, heteroaryl (bonded to the indicated group at a ring carbon atom) and heteroalicyclyl (likewise bonded to the indicated group at a ring carbon atom), as these groups are defined herein. If two "R" groups are covalently bonded to the same atom then they may be bound together so as to form a cycloalkyl or heteroalicyclyl group.

Unless otherwise indicated, when a substituent is deemed to be "optionally substituted," it is meant that the substituent is a group that may be substituted with one or more group(s) individually and independently selected from alkyl, alkenyl, alkynyl, cycloalkyl, aryl, heteroaryl, heteroalicyclic, hydroxyl, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof. The protecting groups that may form the protective derivatives of the above substituents are known to those of skill in the art and may be found in references such as Greene and Wuts, Protective Groups in Organic Synthesis, $3^{rd}$ Ed., John Wiley & Sons, New York, N.Y., 1999, which is incorporated herein in its entirety.

As used herein, "$C_m$ to $C_n$," in which "m" and "n" are integers refers to the number of carbon atoms in an alkyl, alkenyl or alkynyl group or the number of carbon atoms in the ring of a cycloalkyl or cycloalkenyl group. That is, the alkyl, alkenyl, alkynyl, ring of the cycloalkyl or ring of the cycloalkenyl can contain from "m" to "n", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $CH_3CH(CH_3)$—, $CH_3CH_2CH_2CH_2$—, $CH_3CH_2CH(CH_3)$—, and $(CH_3)_3CH$—. If no "m" and "n" are designated with regard to an alkyl, alkenyl, alkynyl, cycloalkyl or cycloalkenyl group, the broadest range described in these definitions is to be assumed.

As used herein, "aryl" refers to a carbocyclic (all carbon) ring or two or more fused rings (rings that share two adjacent carbon atoms) that have a fully delocalized pi-electron system. Examples of aryl groups include, but are not limited to, benzene, naphthalene and azulene.

As used herein, "heteroaryl" refers to a ring or two or more fused rings that contain(s) one or more heteroatoms selected from the group consisting of nitrogen, oxygen and sulfur in the ring and that have a fully delocalized pi-electron system. Examples of heteroaryl rings include, but are not limited to, furan, thiophene, phthalazinone, pyrrole, oxazole, thiazole, imidazole, pyrazole, isoxazole, isothiazole, triazole, thiadiazole, pyran, pyridine, pyridazine, pyrimidine, pyrazine and triazine.

As used herein, "alkyl" refers to a straight or branched chain fully saturated (no double or triple bonds) hydrocarbon group. An alkyl group of this invention may comprise from 1 to 20 carbon atoms, that is, m=1 and n=20. An alkyl group herein may also be of medium size having 1 to 10 carbon atoms. An alkyl group herein may also be a lower alkyl having 1 to 5 carbon atoms. Examples of alkyl groups include, without limitation, methyl, ethyl, n-propyl, isopropyl, n-butyl, iso-butyl, sec-butyl, tert-butyl, amyl, tert-amyl, hexyl, heptyl, octyl, nonyl, decyl, undecyl and dodecyl.

An alkyl group of this invention may be substituted or unsubstituted. When substituted, the substituent group(s) is(are) one or more group(s) independently selected from cycloalkyl, aryl, heteroaryl, heteroalicyclyl, hydroxy, protected hydroxyl, alkoxy, aryloxy, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, trihalomethanesulfonyl, —$NR^aR^b$ and protected amino.

As used herein, "alkenyl" refers to an alkyl group that contains in the straight or branched hydrocarbon chain one or more double bonds. An alkenyl group of this invention may be unsubstituted or substituted. When substituted, the substituent(s) may be selected from the same groups disclosed above with regard to alkyl group substitution.

As used herein, "alkynyl" refers to an alkyl group that contains in the straight or branched hydrocarbon chain one or more triple bonds. An alkynyl group of this invention may be unsubstituted or substituted. When substituted, the substituent(s) may be selected from the same groups disclosed above with regard to alkyl group substitution.

As used herein, "acyl" refers to an "RC(=O)—" group with R as defined above.

As used herein, "cycloalkyl" refers to a completely saturated (no double bonds) hydrocarbon ring. Cycloalkyl groups of this invention may range from $C_3$ to $C_8$. A cycloalkyl group may be unsubstituted or substituted. If substituted, the substituent(s) may be selected from those indicated above with regard to substitution of an alkyl group.

As used herein, "cycloalkenyl" refers to a cycloalkyl group that contains one or more double bonds in the ring although, if there is more than one, they cannot form a fully delocalized pi-electron system in the ring (otherwise the group would be "aryl," as defined herein). A cycloalkenyl group of this invention may unsubstituted or substituted. When substituted, the substituent(s) may be selected from the same groups disclosed above with regard to alkyl group substitution.

The term "alkylene" refers to an alkyl group, as defined here, which is a biradical and is connected to two other moieties. Thus, methylene (—CH$_2$—), ethylene (—CH$_2$CH$_2$—), propylene (—CH$_2$CH$_2$CH$_2$—), isopropylene (—CH$_2$—CH(CH$_3$)—), and isobutylene (—CH$_2$—CH(CH$_3$)—CH$_2$—) are examples, without limitation, of an alkylene group. Similar, the term "cycloalkylene" refers to an cycloalkyl group, as defined here, which binds in an analogues way to two other moieties. If the alkyl and cycloalkyl groups contains unsaturated carbons, the terms "alkenylene" and "cycloalkenylene" are used.

As used herein, "heteroalicyclic" or heteroalicyclyl" refers to a ring or one or more fused rings having in the ring system one or more heteroatoms independently selected from nitrogen, oxygen and sulfur. The rings may also contain one or more double bonds provided that they do not form a fully delocalized pi-electron system in the rings. Heteroalicyclyl groups of this invention may be unsubstituted or substituted. When substituted, the substituent(s) may be one or more groups independently selected from the group consisting of halogen, hydroxy, protected hydroxy, cyano, nitro, alkyl, alkoxy, acyl, acyloxy, carboxy, protected carboxy, amino, protected amino, carboxamide, protected carboxamide, alkylsulfonamido and trifluoromethanesulfonamido.

An "O-carboxy" group refers to a "RC(=O)O—" group with R as defined above.

A "C-carboxy" group refers to a "—C(=O)R" group with R as defined above.

An "acetyl" group refers to a CH$_3$C(=O)— group.

A "trihalomethanesulfonyl" group refers to an "X$_3$CSO$_2$—" group wherein X is a halogen.

A "cyano" group refers to a "—CN" group.

An "isocyanato" group refers to an "—NCO" group.

A "thiocyanato" group refers to a "—CNS" group.

An "isothiocyanato" group refers to an "—NCS" group.

A "sulfinyl" group refers to an "—S(=O)—R" group with R as defined above.

A "sulfonyl" group refers to an "SO$_2$R" group with R as defined above.

An "S-sulfonamido" group refers to a "—SO$_2$NR$^a$R$^b$" group with R$^a$ and R$^b$ as defined above.

An "N-sulfonamido" group refers to a "RSO$_2$N(R$^a$)—" group with R and R$^a$ as defined above.

A "trihalomethanesulfonamido" group refers to an "X$_3$CSO$_2$N(R)—" group with X as halogen and R as defined above.

An "O-carbamyl" group refers to a "—OC(=O)NR$^a$R$^b$" group with R$^a$ and R$^b$ as defined above.

An "N-carbamyl" group refers to an "ROC(=O)NR$^a$—" group with R$^a$ and R as defined above.

An "O-thiocarbamyl" group refers to a "—OC(=S)—NR$^a$R$^b$" group with R$^a$ and R$^b$ as defined above.

An "N-thiocarbamyl" group refers to an "ROC(=S)NR$^a$—" group with R$^a$ and R as defined above.

A "C-amido" group refers to a "—C(=O)NR$^a$R$^b$" group with R$^a$ and R$^b$ as defined above.

An "N-amido" group refers to a "RC(=O)NR$^a$—" group with R and R$^a$ as defined above.

The term "perhaloalkyl" refers to an alkyl group in which all the hydrogen atoms are replaced by halogen atoms.

As used herein, an "ester" refers to a "—C(=O)OR" group with R as defined above.

As used herein, an "amide" refers to a "—C(=O)NR$^a$R$^b$" group with R$^a$ and R$^b$ as defined above.

Any unsubstituted or monosubstituted amine group on a compound herein can be converted to an amide, any hydroxyl group can be converted to an ester and any carboxyl group can be converted to either an amide or ester using techniques well-known to those skilled in the art (see, for example, Greene and Wuts, Protective Groups in Organic Synthesis, 3$^{rd}$ Ed., John Wiley & Sons, New York, N.Y., 1999).

When two substituents are referred to herein as optionally binding together, it is meant that the groups may be joined to form a cycloalkyl, aryl, heteroaryl, or heteroalicyclyl group. For example, without limitation, if R$^a$ and R$^b$ of an NR$^a$R$^b$ group are indicated to be optionally bound together, it is meant that they are covalently bonded to one another at their terminal atoms to form a ring:

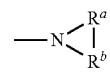

It is understood that, in any compound of this invention having one or more chiral centers, if an absolute stereochemistry is not expressly indicated, then each center may independently be R or S or a mixture thereof. In addition it is understood that, in any compound of this invention having one or more double bond(s) generating geometrical isomers that can be defined as E or Z each double bond may independently be E or Z a mixture thereof.

As used herein, "pharmaceutically acceptable salt" refers to a salt of a compound that does not cause significant irritation to a patient to which it is administered and does not abrogate the biological activity and properties of the compound. Pharmaceutical salts can be obtained by reaction of a compound disclosed herein with an acid or base. Base-formed salts include, without limitation, ammonium salt (NH$_4^+$); alkali metal, such as, without limitation, sodium or potassium, salts; alkaline earth, such as, without limitation, calcium or magnesium, salts; salts of organic bases such as, without limitation, dicyclohexylamine, N-methyl-D-glucamine, tris(hydroxymethyl)methylamine; and salts with the amino group of amino acids such as, without limitation, arginine and lysine. Useful acid-based salts include, without limitation, hydrochlorides, hydrobromides, sulfates, nitrates, phosphates, methanesulfonates, ethanesulfonates, p-toluenesulfonates and salicylates.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may decrease the rate of metabolic degradation for instance by decreasing O-glucuronidation and or O-sulfation. The prodrug may also have improved solubility in pharmaceutical compositions over the parent drug. An example, without limitation, of a prodrug would be a compound disclosed herein, which is administered as an ester (the "prodrug") to facilitate absorption over a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety.

Synthesis

General synthetic routes to the compounds of this invention are shown in Schemes 1-5. The routes shown are illustrative only and are not intended, nor are they to be construed, to limit the scope of this invention in any manner whatsoever. Those skilled in the art will be able to recognize modifications of the disclosed synthesis and to devise alternate routes based on the disclosures herein; all such modifications and alternate routes are within the scope of this invention.

Synthetic rounts for synthesizing the compounds of formula I include the following Schemes 1-6:

SCHEME 1

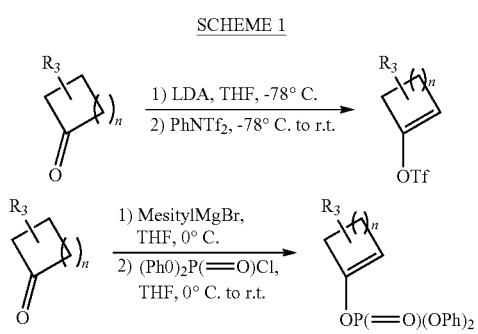

SCHEME 2

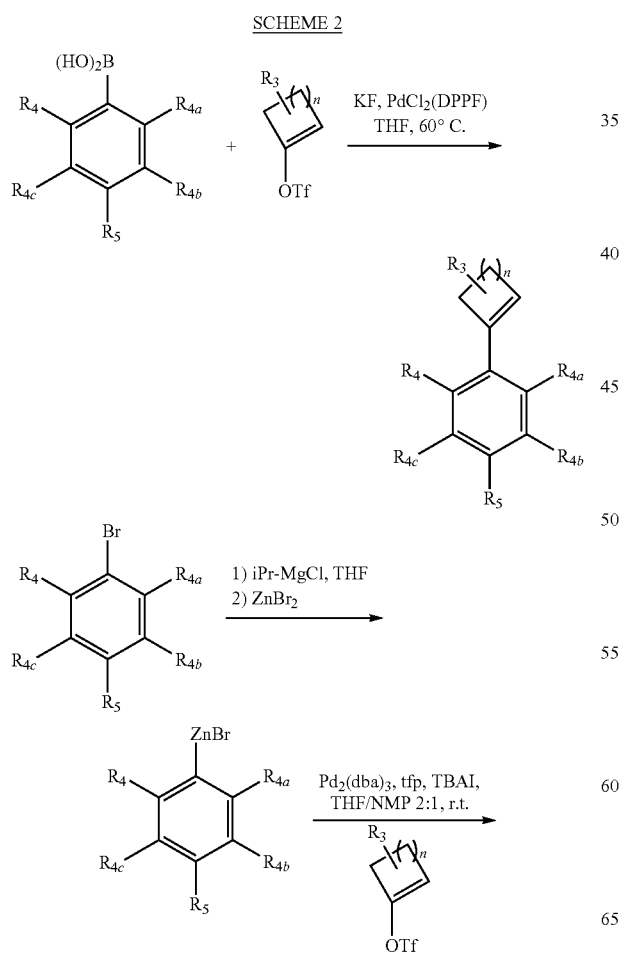

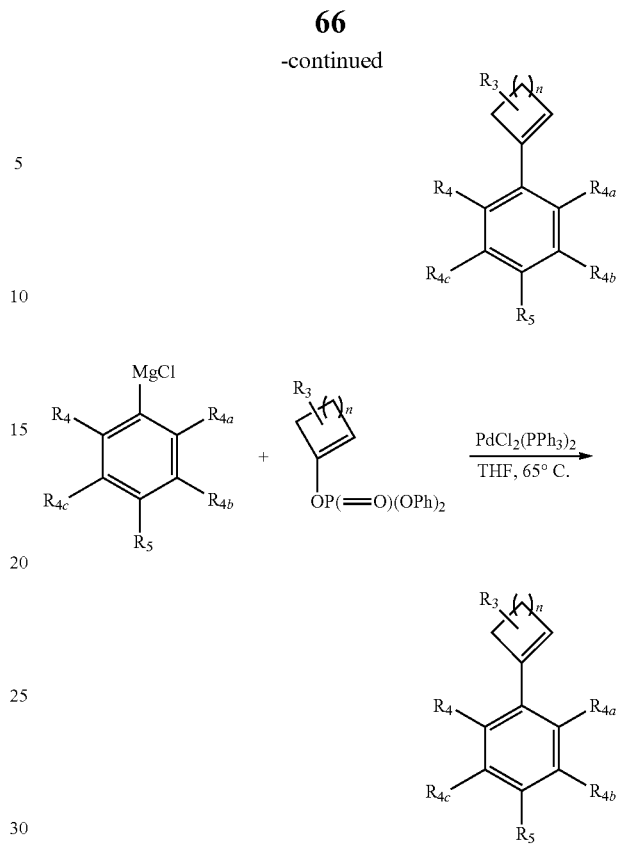

SCHEME 3

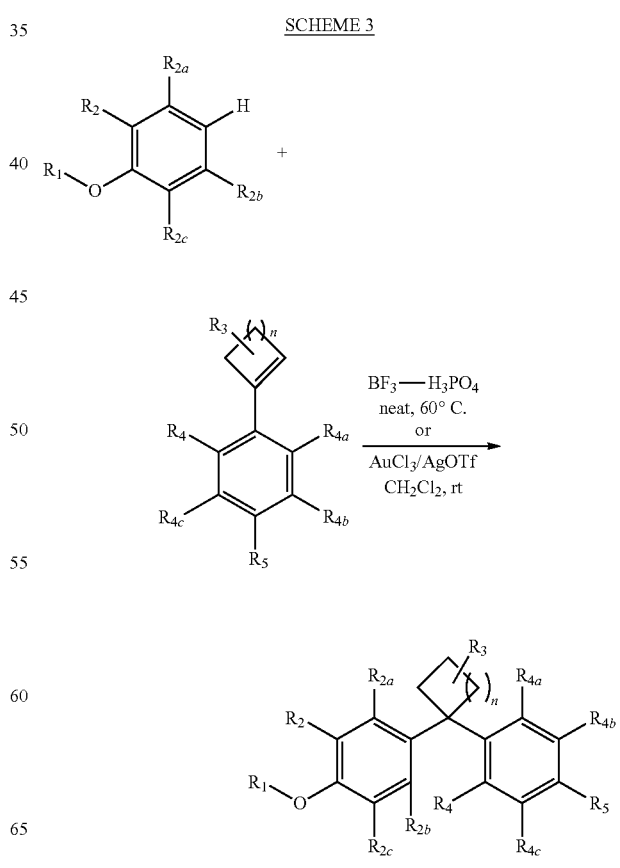

SCHEME 4
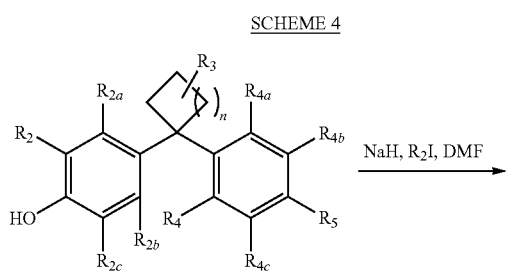
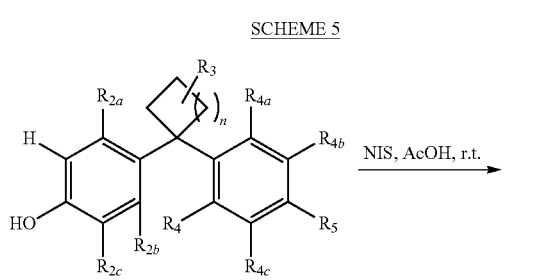
SCHEME 5
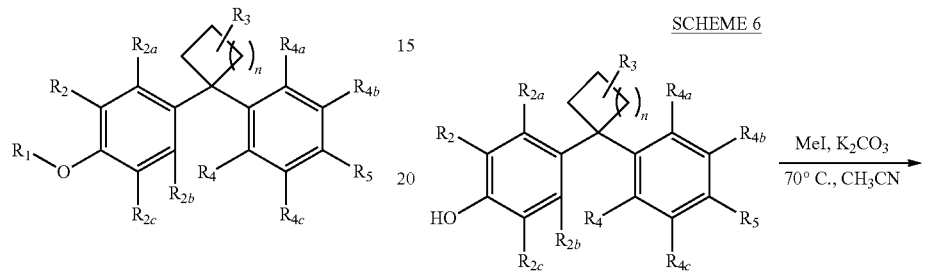
SCHEME 6
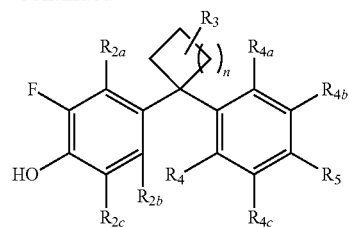
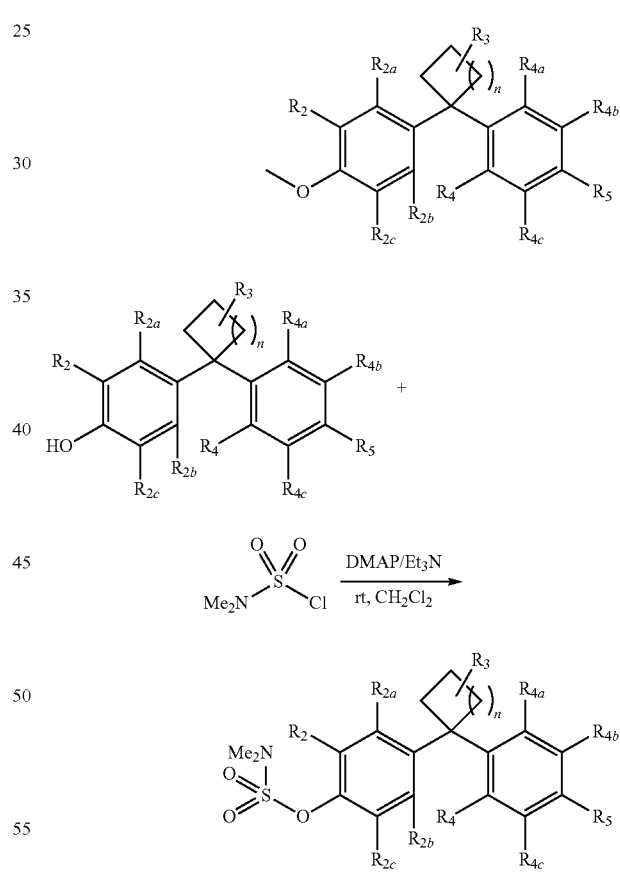
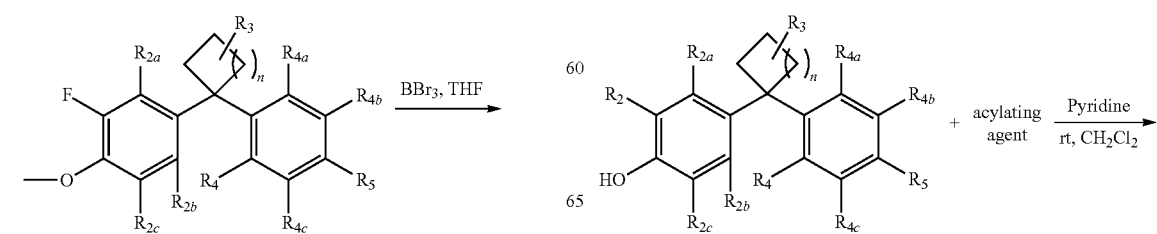

-continued
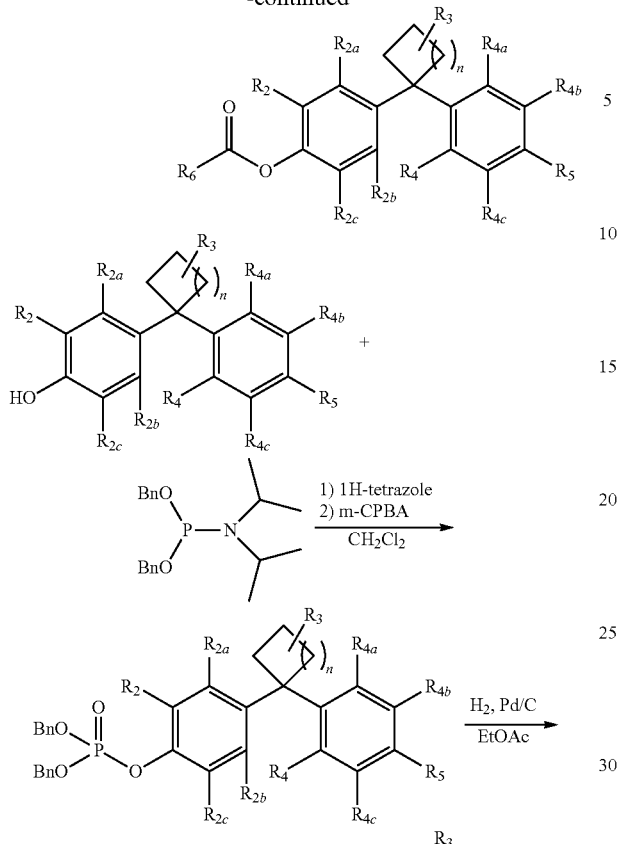
In the above schemes, it is to be understood that the moiety:
is identical to the moiety:
as described above with respect to Formula I.
Synthetic rounts for synthesizing the compounds of formula II include the following Schemes 7-17:
SCHEME 7
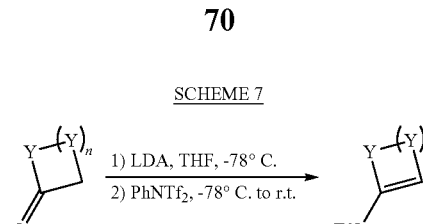
SCHEME 8
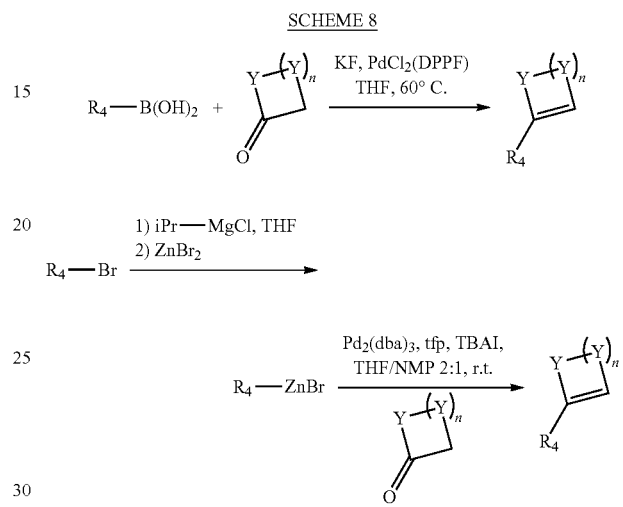
SCHEME 9
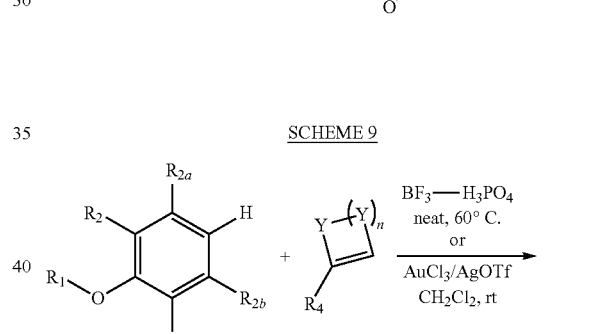
SCHEME 10
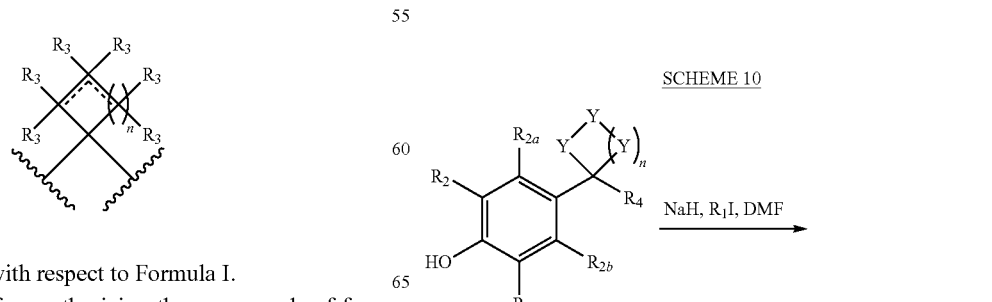

-continued
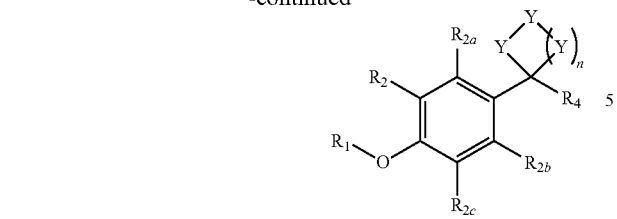
SCHEME 11
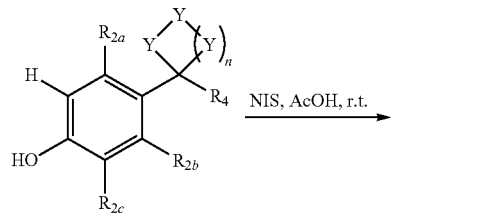
NIS, AcOH, r.t.
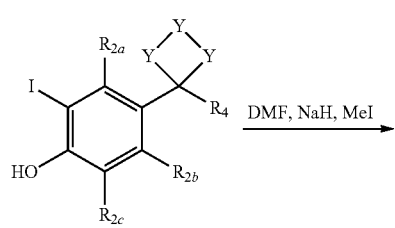
DMF, NaH, MeI
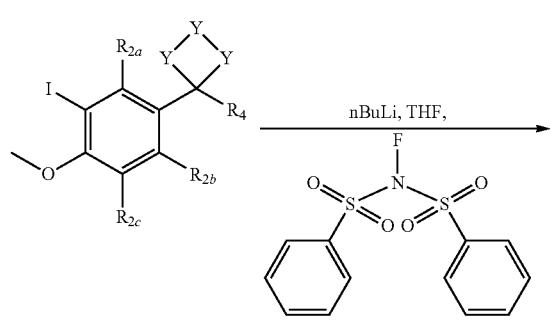
nBuLi, THF,
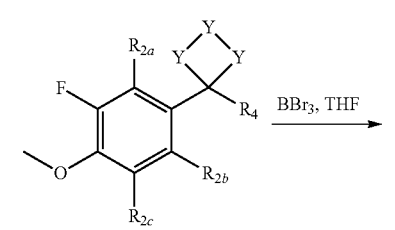
BBr₃, THF
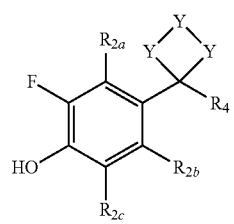
SCHEME 12
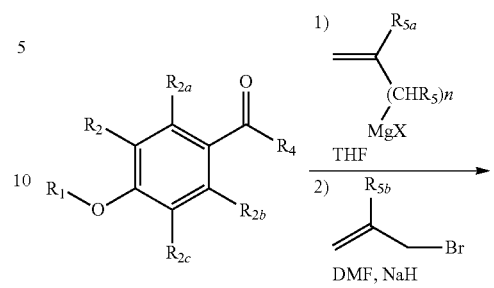
1) [reagent with R₅ₐ, (CHR₅)ₙ, MgX] THF
2) [reagent with R₅ᵦ, Br] DMF, NaH
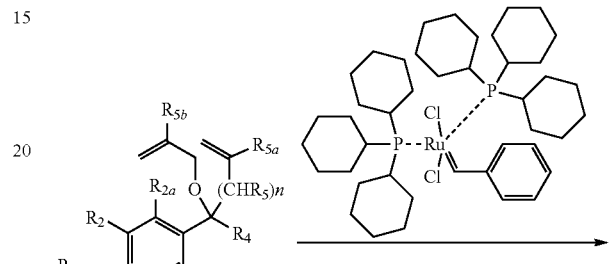
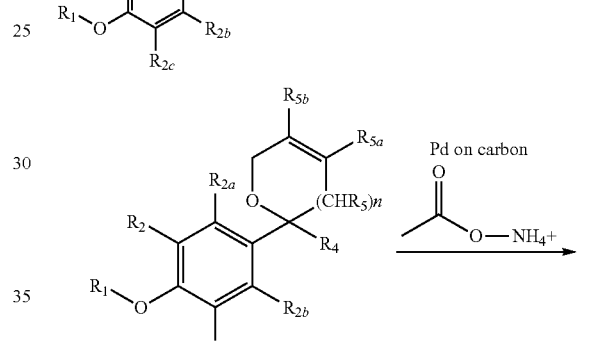
Pd on carbon
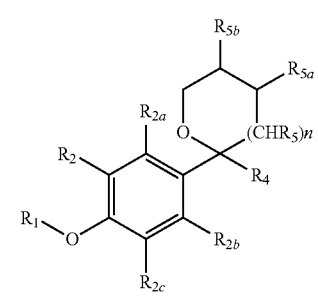
n = 1-4
SCHEME 13
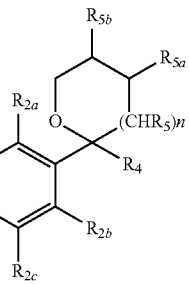
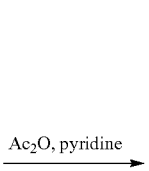
Ac₂O, pyridine

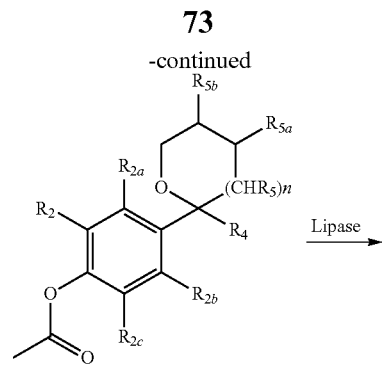
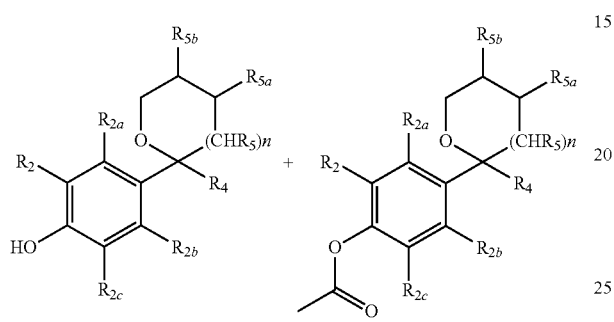
SCHEME 14
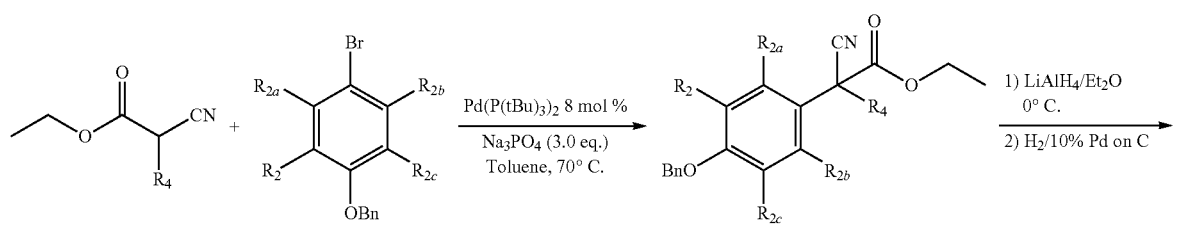
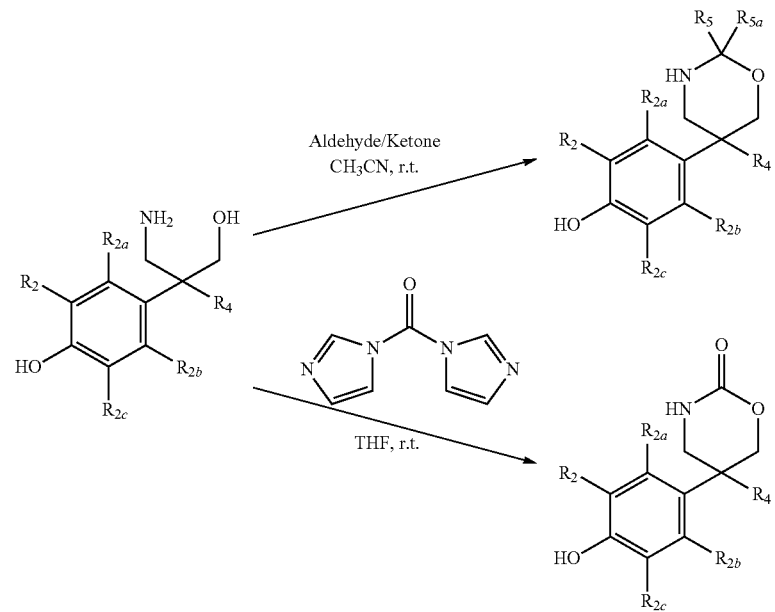

SCHEME 15
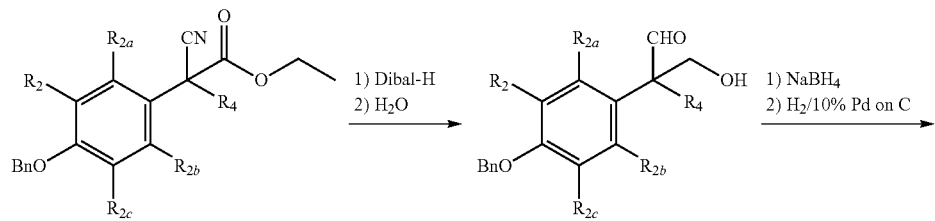
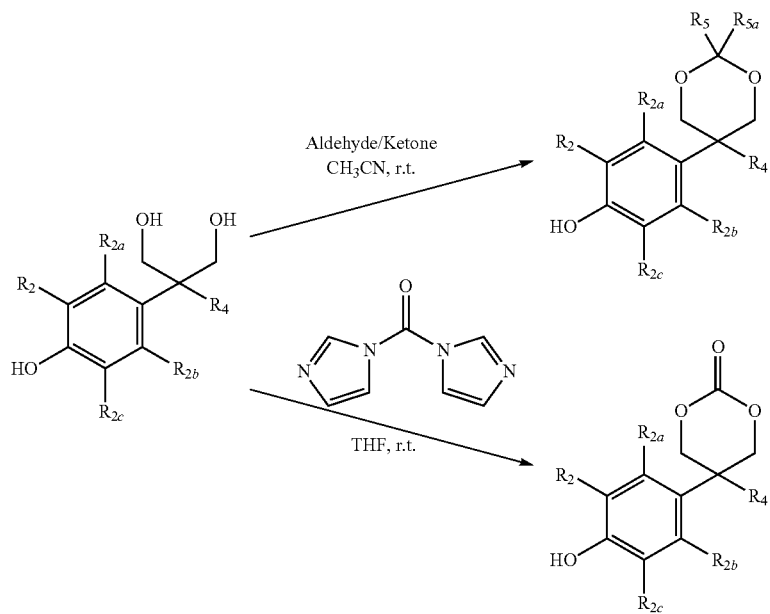
SCHEME 16
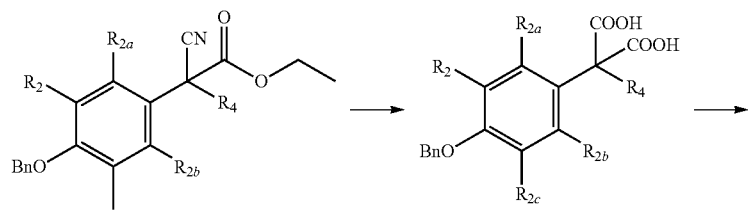
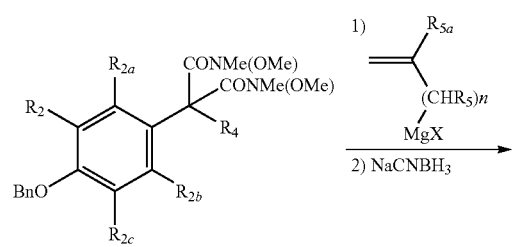

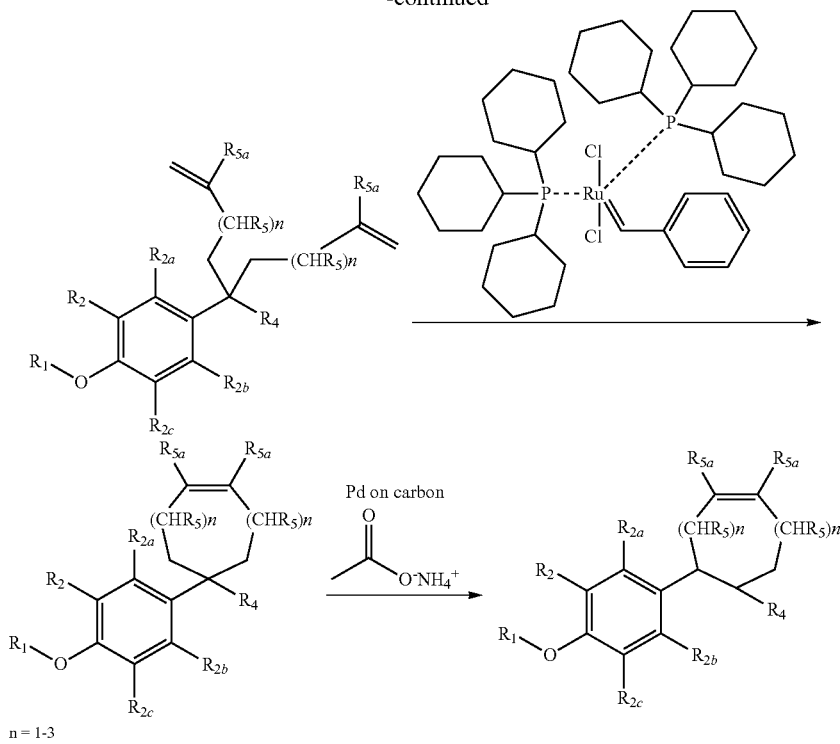
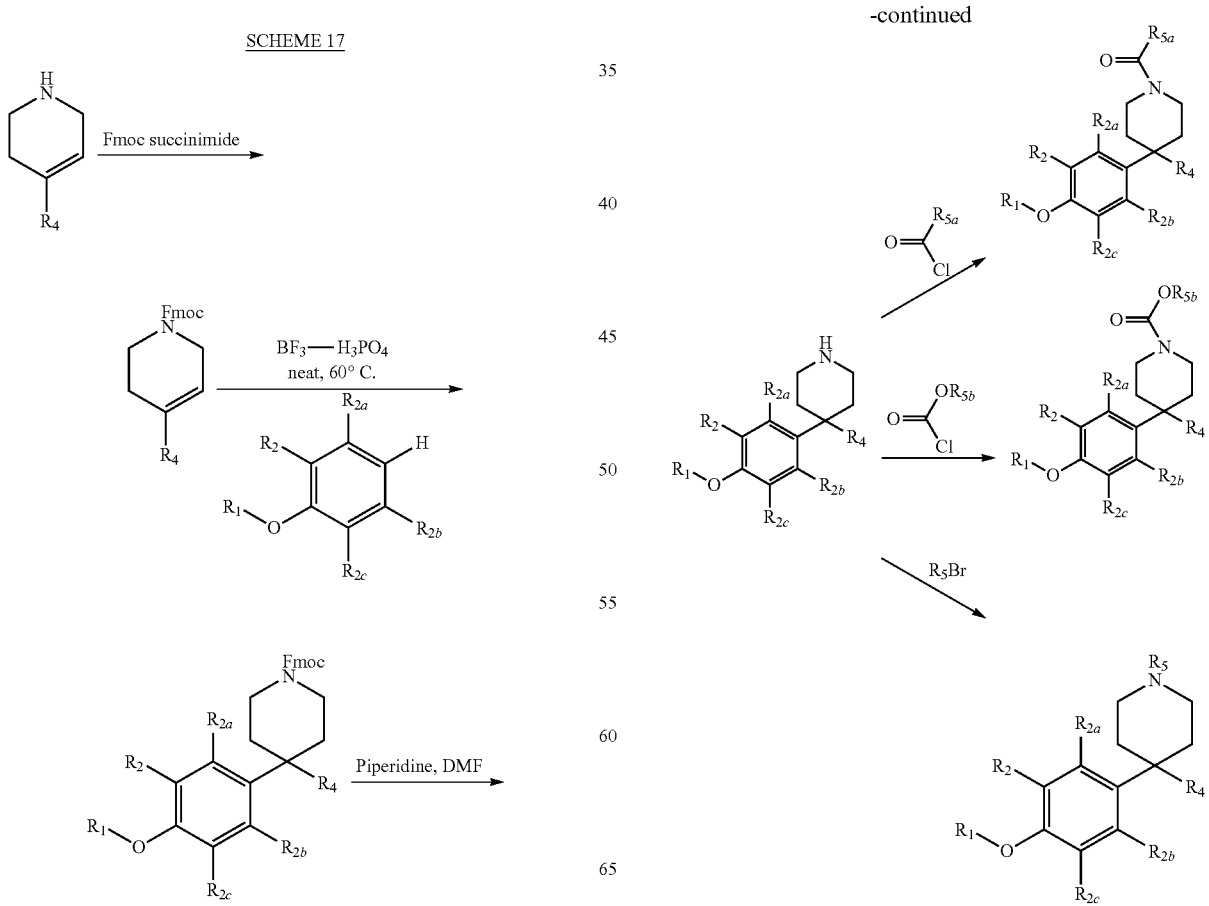
SCHEME 17

Also disclosed herein are methods of treating clinical manifestations in which estrogen receptor function is altered; a method of treating or preventing inflammatory bowel syndrome, Crohn's disease, ulcerative proctitis or colitis; a method of treating or preventing prostatic hypertrophy, uterine leiomyomas, breast carcinoma, endometrial carcinoma, polycystic ovary syndrome, endometrial polyps, benign breast disease, adenomyosis, ovarian carcinoma, melanoma, prostate carcinoma, colon carcinoma, or brain tumors including glioblastoma, astrocytoma, glioma, or meningioma; a method of treating or preventing prostatitis or interstitial cystitis; a method of hormonal replacement therapy; a method of treating or preventing bone density loss including osteoporosis and osteopenia; a method of lowering cholesterol, triglycerides, or LDL levels; a method of treating or preventing discholesterolemia or dislipidemia; a method of treating or preventing cardiovascular disease, atherosclerosis, hypertension, peripheral vascular disease, restenosis or vasospasm; a method of treating impaired cognition or providing neuroprotection; a method of treating or preventing neurodegenerative disorders, including Alzheimer's disease, Huntington's disease, Parkinson's disease or other dementias; a method of treating a spinal cord injury; a method of treating or preventing cognitive decline, stroke, or anxiety; a method of treating or preventing free radical induced disease states; a method of treating or preventing vaginal atrophy, vulvar atrophy, atrophic vaginitis, vaginal dryness, pruritus, dyspareunia, frequent urination, urinary incontinence, or urinary tract infections; a method of treating or preventing vasomotor symptoms including flushing or hot flashes; a method of preventing conception; a method of treating or preventing endometriosis; a method of treating or preventing arthritis, including but not limited to rheumatoid arthritis, osteoarthritis, or arthropathies; a method of treating or preventing psoriasis or dermatitis, a method of treating or preventing asthma or pleurisy; a method of treating or preventing multiple sclerosis, systemic lupus erthematosis, uveitis, sepsis, or hemmorhagic shock; a method of treating or preventing type II diabetes; a method for treating acute and chronic inflammation of any type; a method of treating or preventing lung disorders such as asthma, chronic obstructive pulmonary disease; a method of treating or preventing acute or chronic pain, including neuropathic pain; a method of treating or preventing ophthalmologic disorders including but not limited to glaucoma, dry eye, macular degeneration, and a method of modulating or specifically agonizing one or more Estrogen receptors where the methods comprise identifying a subject in need of treatment or prevention and administering to the subject a pharmaceutically effective amount of a compound of formula I or II.

Another embodiment is a method of identifying a compound that alleviates inflammation in a subject, comprising identifying a subject suffering from inflammation; providing the subject with at least one compound of Formula I or II, as defined herein; and determining if the at least one compound reduces inflammation in the subject.

The term "subject" refers to an animal, preferably a mammal, and most preferably a human, who is the object of treatment, observation or experiment. The mammal may be selected from the group consisting of mice, rats, rabbits, guinea pigs, dogs, cats, sheep, goats, cows, primates, such as monkeys, chimpanzees, and apes, and humans.

The term "therapeutically effective amount" is used to indicate an amount of an active compound, or pharmaceutical agent, that elicits the biological or medicinal response indicated. This response may occur in a tissue, system, animal or human that is being sought by a researcher, veterinarian, medical doctor or other clinician, and includes alleviation of the symptoms of the disease being treated.

Another embodiment is a method of identifying a compound which regulates activity of an Estrogen receptor by culturing cells that express the Estrogen receptors; incubating the cells with at least one compound of Formula I or II as defined herein; and determining any change in activity of the Estrogen receptors so as to identify a compound of Formula I or II which regulates activity of a Estrogen receptors.

In other embodiments, methods are provided for alleviating diseases by administering one or more compounds of Formula I or II. These methods include, but are not limited to methods such as: a method of treating clinical manifestations in which estrogen receptor function is altered; a method of treating or preventing inflammatory bowel syndrome, Crohn's disease, ulcerative proctitis or colitis; a method of treating or preventing prostatic hypertrophy, uterine leiomyomas, breast carcinoma, endometrial carcinoma, polycystic ovary syndrome, endometrial polyps, benign breast disease, adenomyosis, ovarian carcinoma, melanoma, prostate carcinoma, colon carcinoma, brain tumors including but not limited to glioblastoma, astrocytoma, glioma, and meningioma; a method of treating or preventing prostatitis or interstitial cystitis; a method of hormonal replacement therapy; a method of treating or preventing bone density loss including but not limited to osteoporosis or osteopenia; a method of lowering cholesterol, triglycerides, or LDL levels; a method of treating or preventing discholesterolemia, or dislipidemia; a method of treating or preventing cardiovascular disease, atherosclerosis, hypertension, peripheral vascular disease, restenosis or vasospasm; a method of treating impaired cognition or providing neuroprotection; a method of treating neurodegenerative disorders, including but not limited to Alzheimer's disease, Huntington's disease, Parkinson's disease or other dementias; a method of treating a spinal cord injury; a method of treating or preventing cognitive decline, stroke, or anxiety; a method of treating or preventing free radical induced disease states; a method of treating or preventing vaginal atrophy, vulvar atrophy, atrophic vaginitis, vaginal dryness, pruritus, dyspareunia, frequent urination, urinary incontinence, or urinary tract infections; a method of treating or preventing vasomotor symptoms including but not limited to flushing or hot flashes; a method of preventing conception; a method of treating or preventing endometriosis; a method of treating or preventing arthritis, including but not limited to rheumatoid arthritis, osteoarthritis, arthropathies; a method of treating or preventing psoriasis or dermatitis; a method of treating or preventing asthma, or pleurisy; a method of treating or preventing multiple sclerosis, systemic lupus erthematosis, uveitis, sepsis, or hemmorhagic shock; a method of treating or preventing type II diabetes; a method for treating acute and chronic inflammation of any type; a method of treating or preventing lung disorders such as asthma or chronic obstructive pulmonary disease; a method of treating or preventing acute or chronic pain, including neuropathic pain; and a method of treating or preventing ophthalmologic disorders including but not limited to glaucoma, dry eye, macular degeneration. In other embodiments, methods of modulating, or specifically agonizing, the Estrogen receptors by administering an effective amount of a compound of Formula I or II are provided.

Another embodiment is a pharmaceutical composition comprising a compound of Formula I or II as described above, and a physiologically acceptable carrier, diluent, or excipient, or a combination thereof.

The term "pharmaceutical composition" refers to a mixture of a compound disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990, which is hereby incorporated by reference in its entirety.

Suitable routes of administration may, for example, include oral, rectal, transmucosal, or intestinal administration; parenteral delivery, including intramuscular, subcutaneous, intravenous, intramedullary injections, as well as intrathecal, direct intraventricular, intraperitoneal, intranasal, intraocular injections or as an aerosol inhalant.

Alternately, one may administer the compound in a local rather than systemic manner, for example, via injection of the compound directly into the area of pain or inflammation, often in a depot or sustained release formulation. Furthermore, one may administer the drug in a targeted drug delivery system, for example, in a liposome coated with a tissue-specific antibody. The liposomes will be targeted to and taken up selectively by the organ.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes.

Pharmaceutical compositions for use in accordance with the present disclosure thus may be formulated in conventional manner using one or more physiologically acceptable carriers comprising excipients and auxiliaries, which facilitate processing of the active compounds into preparations, which can be used pharmaceutically. Proper formulation is dependent upon the route of administration chosen. Any of the well-known techniques, carriers, and excipients may be used as suitable and as understood in the art; e.g., as disclosed in Remington's Pharmaceutical Sciences, cited above.

For injection, the agents disclosed herein may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds disclosed herein to be formulated as tablets, pills, dragees, capsules, liquids, gels, syrups, slurries, suspensions and the like, for oral ingestion by a patient to be treated. Pharmaceutical preparations for oral use can be obtained by mixing one or more solid excipient with pharmaceutical combination disclosed herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations, which can be used orally, include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present disclosure are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances, which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly, concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds disclosed herein is a co-solvent system comprising benzyl alcohol, a nonpolar surfactant, a water-miscible organic polymer, and an aqueous phase. A common co-solvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of Polysorbate 80™; the fraction size of polyethylene glycol may be varied; and other biocompatible polymers may replace polyethylene glycol, e.g., polyvinyl pyrrolidone. Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Many of the compounds used in the pharmaceutical combinations disclosed herein may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free acids or base forms.

Pharmaceutical compositions suitable for use in the methods disclosed herein include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

The exact formulation, route of administration and dosage for the pharmaceutical compositions disclosed herein can be chosen by the individual physician in view of the patient's condition. (See e.g., Fingl et al. 1975, in "The Pharmacological Basis of Therapeutics", Chapter 1, which is hereby incorporated by reference in its entirety). Typically, the dose range of the composition administered to the patient can be from about 0.5 to 1000 mg/kg of the patient's body weight, or 1 to 500 mg/kg, or 10 to 500 mg/kg, or 50 to 100 mg/kg of the patient's body weight. The dosage may be a single one or a series of two or more given in the course of one or more days, as is needed by the patient. Where no human dosage is established, a suitable human dosage can be inferred from $ED_{50}$ or $ID_{50}$ values, or other appropriate values derived from in vitro or in vivo studies, as qualified by toxicity studies and efficacy studies in animals.

Although the exact dosage will be determined on a drug-by-drug basis, in most cases, some generalizations regarding the dosage can be made. The daily dosage regimen for an adult human patient may be, for example, an oral dose of between 0.1 mg and 500 mg of each ingredient, preferably between 1 mg and 250 mg, e.g. 5 to 200 mg or an intravenous, subcutaneous, or intramuscular dose of each ingredient between 0.01 mg and 100 mg, preferably between 0.1 mg and 60 mg, e.g. 1 to 40 mg of each ingredient of the pharmaceutical compositions disclosed herein or a pharmaceutically acceptable salt thereof calculated as the free base, the composition being administered 1 to 4 times per day. Alternatively the compositions disclosed herein may be administered by continuous intravenous infusion, preferably at a dose of each ingredient up to 400 mg per day. Thus, the total daily dosage by oral administration of each ingredient will typically be in the range 1 to 2000 mg and the total daily dosage by parenteral administration will typically be in the range 0.1 to 400 mg. In some embodiments, the compounds will be administered for a period of continuous therapy, for example for a week or more, or for months or years.

Dosage amount and interval may be adjusted individually to provide plasma levels of the active moiety, which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen, which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device, which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound disclosed herein formulated in a compatible pharmaceutical carrier may also be prepared, placed in an appropriate container, and labeled for treatment of an indicated condition.

It will be understood by those of skill in the art that numerous and various modifications can be made without departing from the spirit of the present disclosure. Therefore, it should be clearly understood that the forms disclosed herein are illustrative only and are not intended to limit the scope of the present disclosure.

EXAMPLES

Embodiments of the present invention are disclosed in further detail in the following examples, which are not in any way intended to limit the scope of the invention.

Example 1

General Analytical LC-MS Procedure

Procedure 1 (AP1): The analysis was performed on a combined prep/analytical Waters/Micromass system consisting of a ZMD single quadropole mass spectrometer equipped with electro-spray ionization interface. The HPLC system consisted of a Waters 600 gradient pump with on-line degassing, a 2700 sample manager and a 996 PDA detector.

Separation was performed on an X-Terra MS C18, 5 µm 4.6×50 mm column. Buffer A: 10 mM ammonium acetate in water, buffer B: 10 mM ammonium acetate in acetonitrile/water 95/5. A gradient was run from 30% B to 100% B in 10 min, dwelling at 100% B for 1 min, and re-equilibrating for 6 min. The system was operated at 1 ml/min.

Procedure 2 (AP2): The analysis was performed on a combined prep/analytical Waters/Micromass system consisting of a ZMD single quadropole mass spectrometer equipped with electro-spray ionization interface. The HPLC system consisted of a Waters 600 gradient pump with on-line degassing, a 2700 sample manager and a 996 PDA detector.

Separation was performed on an X-Terra MS C18, 5 µm 4.6×50 mm column. Buffer A: 10 mM ammonium acetate in water, buffer B: 10 mM ammonium acetate in acetonitrile/water 95/5. A gradient was run from 30% B to 100% B in 7 min, dwelling at 100% B for 1 min, and re-equilibrating for 5.5 min. The system was operated at 1 ml/min.

Example 2

General Gas Chromatography (GC) Procedure

GC method 50 was used. Method 50 starts at 50° C. and has a gradient of 20° C./min until 250° C. then holds the temperature for 5 minutes. The analysis was performed on an Aglient 6850 series GC system with capillary S/SL inlet and FID with EPC installation. The column was a 10 m×0.32 mm×0.25 µm HP5 column.

Example 3

Synthesis of Trifluoromethanesulfonates, General Procedure 1 (GP1)

Trifluoromethanesulfonates were prepared according to literature procedure by McMurry and Scott (McMurry, J. E.; Scott, W. J., *Tetrahedron letters*, 1983, 979-982).

4-isoPropyl-cyclehexenyl-1-trifluoromethanesulfonate

The title compound was prepared according to GP1 from 4-ipropylcyclohexanone (10.0 g, 71 mmol). Crude yield: 14.1 g. $^1$H-NMR (400 MHz, CDCl$_3$) d 5.78-5.69 (m, 1H), 2.42-2.14 (m, 3H), 1.98-1.84 (m, 2H), 1.60-1.2 (m, 4H), 0.94-0.88 (m, 6H).

1-Cyclohexenyl-1-trifluoromethanesulfonate

The title compound was prepared according to GP1 from cyclohexanone (9.8 g, 100 mmol). Crude yield: 14.0 g (83% pure by $^1$H-NMR). $^1$H-NMR (400 MHz, CDCl$_3$) d 5.79-5.73 (m, 1H), 2.36-2.28 (m, 2H), 2.23-2.14 (m, 2H), 1.83-1.75 (m, 2H), 1.66-1.56 (m, 2H).

4-Trifluoromethyl-cyclohexenyl-1-trifluoromethanesulfonate

The title compound was prepared according to GP1 from 4-(trifluoromethyl)cyclohexanone (3.0 g, 18 mmol). Crude yield: 1.9 g. GC-FID R$_t$: 1.16 min (Method 50)

1-Cycloheptenyl-1-trifluoromethanesulfonate

The title compound was prepared according to GP1 from cycloheptanone (2.2 g, 20 mmol). Crude yield: 3.7 g.
$^1$H-NMR (400 MHz, CDCl$_3$) d 5.86-5.74 (m, 1H), 2.51-2.40 (m, 2H), 2.14-2.06 (m, 2H), 1.77-1.49 (m, 6H).

Example 4

Suzuki Coupling, General Procedure 2 (GP2)

The appropriate boronic acid (4.4 mmol) was dissolved in dry THF (20 mL) and cyclohexenyl triflate (4.0 mmol) and KF (13.2 mmol) was added. The solution was degassed and kept under Argon and PdCl$_2$(dppf) (65.3 mg, 0.08 mmol) was added. The reaction was shaken overnight at rt after which time they were filtered through celite, rinsed with EtOAc and subjected to column chromatography (silica, hexane).

2,6-Difluorophenyl cyclohexene

The title compound was prepared according to GP2. Yield: 551 mg (2.84 mmol, 71%). $^1$H-NMR (400 MHz, CDCl$_3$) d 7.17-7.10 (m, 1H), 6.88-6.81 (m, 2H), 5.80 (m, 1H), 2.26-2.19 (m, 4H), 1.78-1.70 (m, 4H). GC Analysis: R$_t$=2.55 min (Method 50), 97%.

2,5-Difluorophenyl cyclohexene

The title compound was prepared according to GP2. Yield: 596 mg (3.07 mmol, 77%). $^1$H-NMR (400 MHz, CDCl$_3$) d 6.88-6.81 (m, 2H), 6.78-6.73 (m, 1H), 5.88 (m, 1H), 2.26-2.23 (m, 2H), 2.13-2.09 (m, 2H), 1.68-1.64 (m, 2H), 1.61-1.57 (m, 2H). GC Analysis (method 50): $R_t$=2.77 min, 91%.

2,4-Difluorophenyl cyclohexene

The title compound was prepared according to GP2. Yield: 290 mg (1.49 mmol, 37%), $^1$H-NMR (400 MHz, CDCl$_3$) d 7.12 (ddd, 1H, J=8.6 Hz, 6.6 Hz, 6.6 Hz), 6.77-6.68 (m, 2H), 5.82 (m, 1H), 2.29-2.25 (m, 2H), 2.16-2.11 (m, 2H), 1.73-1.59 (m, 4H). GC Analysis (method 50): $R_t$=2.62 min, 98%.

5-Chloro-2-fluorophenyl cyclohexene

The title compound was prepared according to GP2. Yield: 701 mg (3.32 mmol, 83%). $^1$H-NMR (400 MHz, CDCl$_3$) d 7.15 (dd, 1H, J=6.65 Hz, 2.74 Hz), 7.06 (m, 1H), 6.88 (dd, 1H, J=10.27 Hz, 8.70 Hz), 5.90 (m, 1H), 2.28-2.26 (m, 2H), 2.17-2.13 (m, 2H), 1.71-1.67 (m, 2H), 1.65-1.60 (m, 2H). GC Analysis: $R_t$=3.88 min, 94%.

Example 5

Negishi Coupling, General Procedure 3 (GP3)

1-(1-Cyclohexen-1-yl)-3-methoxy-benzene

In a dry and argon flushed two neck flask, tris(dibenzylideneacetone) dipalladium (275 mg, 0.3 mmol) and tri-2-furylphosphine (278 mg, 1.2 mmol) was dissolved in N-methylpyrrolidone. Tetrabutyl ammonium iodide (2.21 g, 6.0 mmol) and 1-cyclohexenyl-1-trifluoromethanesulfonate (1.85 g, 6.0 mmol) were added to the reaction mixture followed by phenylzinc bromide (12 mL, 1.0 M, 12 mmol) and the reaction mixture was left stirring at room temperature over night. The reaction was quenched with saturated ammonium chloride solution. The product was filtered through celite, taken up in ethyl acetate and washed with brine, dried over Na$_2$SO$_4$, and concentrated in vacuo. The title compound was obtained and purified by flash chromatography (silica, 0-10% EtOAc in heptane). Yield: 700 mg. $^1$H-NMR (400 MHz, CDCl$_3$) δ: 7.23 (t, J=7.8 Hz, 1H), 7.04 (d, J=7.8 Hz, 1H), 6.98 (s, 1H), 6.81 (d, J=7.8 Hz, 1H), 6.18-6.17 (m, 1H), 3.82 (s, 3H), 2.45-2.42 (m, 2H), 2.24-2.21 (m, 2H), 1.83-1.79 (m, 2H), 1.72-1.68 (m, 2H).

4-(Trifluoromethyl)-1-cyclohexen-1-yl]-benzene

The title compound was prepared according to GP3 from 4-(trifluoromethyl)-1-cyclohexenyl-1-trifluoromethanesulfonate (475 mg, 1.6 mmol) and phenylzinc bromide (3.2 mL, 1.0 M, 3.2 mmol). The product was purified by flash chromatography (silica, heptane). Yield: 284 mg. $^1$H-NMR (400 MHz, CDCl$_3$) δ: 7.32-7.15 (m, 5H), 6.01-5.98 (m, 1H), 2.58-2.07 (m, 6H), 1.71-1.58 (m, 1H).

1-Fluoro-4-[4-(trifluoromethyl)-1-cyclohexen-1-yl]-benzene

The title compound was prepared according to GP3 from 4-(trifluoromethyl)-1-cyclohexenyl-1-trifluoromethanesulfonate (475 mg, 1.6 mmol) and 4-fluorophenylzinc bromide (3.2 mL, 1.0 M, 3.2 mmol). The product was purified by flash chromatography (silica, heptane). Yield: 271 mg. $^1$H-NMR (400 MHz, CDCl$_3$) δ: 7.38-7.32 (m, 2H), 7.07-6.98 (m, 2H), 6.02-5.99 (m, 1H), 2.61-2.17 (m, 6H), 1.76-1.63 (m, 1H).

1-Fluoro-3-[4-(trifluoromethyl)-1-cyclohexen-1-yl]-benzene

The title compound was prepared according to GP3 from 4-(trifluoromethyl)-1-cyclohexenyl-1-trifluoromethanesulfonate (475 mg, 1.6 mmol) and 3-fluorophenylzinc bromide (3.2 mL, 1.0 M, 3.2 mmol). The product was purified by flash chromatography (silica, heptane). Yield: 363 mg. $^1$H-NMR (400 MHz, CDCl$_3$) δ: 7.35-6.92 (m, 4H), 6.15-6.11 (m, 1H), 2.62-2.15 (m, 6H), 1.75-1.64 (m, 1H).

1-(Cyclohexen-1-yl)-2-fluorobenzene

The title compound was prepared according to GP3 from 1-cyclohexenyl-1-trifluoromethanesulfonate (1.84 g, 8.0 mmol) and 2-fluorophenylzinc bromide (16 mL, 1.0 M, 32 mmol). The product was purified by flash chromatography (silica, heptane). Yield: 678 mg. $^1$H-NMR (400 MHz, CDCl$_3$) δ: 7.30-6.97 (m, 4H), 5.96-5.90 (m, 1H), 2.40-2.33 (m, 2H), 2.23-2.18 (m, 2H), 1.79-1.70 (m, 2H), 1.70-1.64 (m, 2H).

4-(1-Cyclohexen-1-yl)-1,2-difluoro-benzene

The title compound was prepared according to GP3 from 1-cyclohexenyl-1-trifluoromethanesulfonate (1.84 g, 8.0 mmol) and 3,4-difluorophenylzinc bromide (32 mL, 0.5 M, 16 mmol). The product was purified by flash chromatography (silica, heptane). Yield: 1.31 g. $^1$H-NMR (400 MHz, CDCl$_3$) δ: 7.20-7.00 (m, 3H), 6.07-6.00 (m, 1H), 2.38-2.30 (m, 2H), 2.24-2.18 (m, 2H), 1.82-1.66 (m, 4H).

1-(1-Cyclohexen-1-yl)-3,5-difluoro-benzene

The title compound was prepared according to GP3 from 1-cyclohexenyl-1-trifluoromethanesulfonate (1.84 g, 8.0 mmol) and 3,5-difluorophenylzinc bromide (32 mL, 0.5 M, 16 mmol). The product was purified by flash chromatography (silica, heptane). Yield: 934 mg. GC-FID $R_t$: 2.96 min (Method 50)

1-Fluoro-2-[4-(1-i-propyl)-1-cyclohexen-1-yl]-benzene

The title compound was prepared according to GP3 from 4-(1-i-propyl)-1-cyclohexenyl-1-trifluoromethanesulfonate (2.18 g, 8.0 mmol) and 2-fluorophenylzinc iodide (32 mL, 0.5 M, 16.0 mmol). The product was purified by flash chromatography (silica, heptane). Yield: 1.15 g. $^1$H-NMR (400 MHz, CDCl$_3$) δ: 7.30-7.01 (m, 4H), 5.97-5.93 (m, 1H), 2.51-1.34 (m, 8H), 0.98-0.88 (m, 6H).

1-Fluoro-3-[4-(1-i-propyl)-1-cyclohexen-1-yl]-benzene

The title compound was prepared according to GP3 from 4-(1-i-propyl)-1-cyclohexenyl-1-trifluoromethanesulfonate (2.18 g, 8.0 mmol) and 3-fluorophenylzinc iodide (32 mL, 0.5 M, 16.0 mmol). The product was purified by flash chromatography (silica, heptane). Yield: 902 mg. $^1$H-NMR (400 MHz, CDCl$_3$) δ: 7.35-7.12 (m, 3H), 6.92-6.87 (m, 1H), 6.18-6.12 (m, 1H), 2.51-1.35 (m, 8H), 0.99-0.95 (m, 6H).

1-Methoxy-3-[4-(1-i-propyl)-1-cyclohexen-1-yl]-benzene

The title compound was prepared according to GP3 from 4-(1-i-propyl)-1-cyclohexenyl-1-trifluoromethanesulfonate (2.18 g, 8.0 mmol) and 2-methoxyphenylzinc bromide (16 mL, 1.0 M, 16.0 mmol). The product was purified by flash chromatography (silica, heptane). Yield: 1.63 g. GC-FID $R_t$: 6.07 min (Method 50)

Example 6

Vinylaromatic Compounds, General Procedure 4 (GP4)

The vinylaromatic compounds were prepared as exemplified below using cycloheptanone and phenylmagnesium chloride.

1-Phenylcycloheptene, General Procedure 4 (GP4)

Mesitylmagnesium bromide (18.0 mL, 18.0 mmol, 1.0 M in THF) was added over 15 minutes to a solution of cycloheptanone (2.0 g, 17.8 mmol) and diphenyl chlorophosphate (1.1 eq.) in THF (5 mL) at 0° C. The solution was stirred at 0° C. for 30 min, whereafter the solution was allowed to reach room temperature. After stirring the solution for 30 min, dichlorobis(triphenylphosphine)palladium (126 mg, 1 mol %) was added and the solution was warmed to 65° C. Phenylmagnesium chloride (10.8 mL, 1.2 equivalents in THF) was added over 10 minutes, resulting in a gentle reflux of the solvent. After stirring at 65° C. for 30 minutes, the mixture was cooled to rt and poured into a mixture of 3 N HCl (30 mL) and pentane (30 mL). The phases were separated, and the aqueous portion was extracted with pentane (30 mL). The combined organic phase was washed sequentially with 3 N HCl (20 mL), 3 M NaOH (2×20 mL), and brine (20 mL), and dried over MgSO4. Evaporation of the solvent followed by distillation using a Kugelrohr apparatus (oven temperature 100-140° C., 0.065 torr) yielded 1-phenylcycloheptene (1.29 g, 43%).

$^1$H-NMR (400 MHz, CDCl$_3$) δ 7.37-7.20 (m, 5H), 6.11 (t, 1H), 2.65 (m, 2H), 2.30 (m, 2H), 1.88 (m, 2H), 1.70 (m, 2H), 1.60 (m, 2H).
$^{13}$C-NMR (100 MHz, CDCl$_3$) δ 145.2, 140.5, 130.5, 128.3 (2C), 126.5, 126.0 (2C), 33.0, 32.9, 29.0, 27.1, and 27.0.

1-Phenylcycloheptene was also synthesized according to GP3

1-(3-Fluorophenyl)-cycloheptene 1-(3-Fluorophenyl)-cycloheptene was prepared according to GP4 and GP3 described above and isolated by column chromatography. $^1$H-NMR (400 MHz, CDCl$_3$) δ 7.27-7.20 (m, 1H), 7.10 (m, 1H), 7.0 (m, 1H), 6.95-6.85 (m, 1H), 6.10 (t, 1H, J=8.0 Hz), 2.6 (m, 2H), 2.33-2.23 (m, 2H), 1.89-1.8 (m, 2H), 1.7-1.5 (m, 4H). $^{13}$C-NMR (100 MHz, CDCl$_3$) δ 163.0 (d, J=242 Hz), 147.7 (d, J=20 Hz), 144.3, 131.7, 129.7 (d, J=20 Hz), 121.5, 113.1 (d, J=22 Hz), 112.7 (d, J=22 Hz), 32.9, 32.8, 29.0, 27.0, 26.9.

1-(2-Fluorophenyl)-cycloheptene 1-(2-Fluorophenyl)-cycloheptene was prepared according to GP3 described above and isolated by column chromatography. $R_f$=0.85 (heptane).

1-(4-Fluorophenyl)-cycloheptene 1-(4-Fluorophenyl)-cycloheptene was prepared according to GP3 and GP4 described above and isolated by column chromatography.

$^1$H-NMR (400 MHz, CDCl$_3$) δ 7.35-7.25 (m, 2H), 7.00-6.90 (m, 2H), 6.05 (t, 1H, J=8.0 Hz), 2.60 (m, 2H), 2.33-2.23 (m, 2H), 1.90-1.80 (m, 2H), 1.70-1.50 (m, 4H).
$^{13}$C-NMR (100 MHz, CDCl$_3$) δ 161.9 (d, J=244 Hz), 144.2, 141.3 (d, J=3 Hz), 130.5, 127.4 (d, 2C, J=8 Hz), 115.0 (d, 2C, J=21 Hz), 33.2, 32.9, 29.0, 27.1, 27.0.

1-Phenylcyclooctene

1-Phenylcyclooctene was prepared according to GP3 and GP4 described above and isolated by Kugelrohr distillation (oven temperature 120-140° C., 0.065 torr). Yield (1.5 g, 60%).

$^1$H-NMR (400 MHz, CDCl$_3$) δ 7.44-7.39 (m, 2H), 7.33-7.18 (m, 3H), 6.01 (t, 1H, J=8.0 Hz), 2.67-2.61 (m, 2H), 2.34-2.26 (m, 2H), 1.70-1.50 (m, 8H). $^{13}$C-NMR (100 MHz, CDCl$_3$) δ 143.4, 140.5, 128.4 (2C), 128.2, 126.6, 126.0 (2C), 30.2, 29.7, 28.7, 27.6, 27.1, 26.4.

1-Methoxy-4-(1-phenyl-cyclohexyl)-benzene, procedure A

A mixture of AuCl$_3$ (7.6 mg, 0.025 mmol) and AgOTf (19.3 mg, 0.075 mmol) was stirred in dichloromethane (2 mL) for 30 min. Anisole (54 mg, 0.5 mmol) and 1-Phenyl-1-cyclohexene (158 mg, 1 mmol) were then added sequentially. The resulting mixture was stirred at room temperature overnight. Evaporation of the solvent under reduced pressure gave 130 mg of crude material. Flash chromatography (heptane:ethyl acetate 95:5) afforded 90 mg of a as a colorless oil. $R_f$=0.33 (heptane:ethyl acetate 95:5). $^1$H-NMR (400 MHz, CDCl$_3$): 7.27-7.25 (m, 4H), 7.19 (d, 2H, J=8.8 Hz), 7.12 (m, 1H), 6.81 (d, 2H, J=8.8 Hz), 3.77 (s, 3H), 2.30-2.20 (m, 4H), 1.62-1.44 (m, 6H).

1-Methoxy-4-(1-phenyl-cyclohexyl)-benzene (B), procedure B 4-(1-phenylcyclohexyl)phenol (20 mg, 0.08 mmol) was dissolved in DMF (2 mL). A suspension of NaH in oil (60%, 5 mg, 0.125 mmol) was added. After stirring for 5 minutes methyl iodide (0.05 mL; 0.8 mmol) was added. The reaction mixture was stirred for 2 h. (tlc indicated full conversion of the starting material) then quenched with water (10 mL). Dichloromethane (10 mL) was added. The mixture was shaken and the organic phase separated off, dried (Na$_2$SO$_4$) and concentrated to syrup. The title product was afforded after work-up by flash-chromatography (eluent dichloromethane). Yield: 20 mg, quantitatively. LC-MS purity (UV/MS): 100/-, $R_t$ 6.48 min. $^1$H NMR data were in accordance with the data written above.

Example 7

General Procedure 5 (GP5)

4-(1-Phenylcyclohexyl)phenol (ERB-002)

1-Phenyl-1-cyclohexene (1 g, 6.3 mmol), phenol (1.5 g, 15.9 mmol) and BF$_3$.H$_3$PO$_4$ (0.05 mL) were mixed and shaken at 80° C. overnight. Dichloromethane (30 mL) was added and the organic phase was washed with saturated NaHCO$_3$ (aq.) (2×10 mL), dried (Na$_2$SO$_4$) and concentrated. The title compound was crystallised from a mixture of methanol and water. Yield: 1040 mg. $^1$H NMR (400 MHz, CDCl$_3$): δ 7.28-7.25 (m, 4H), 7.16-7.10 (m, 3H), 6.75-6.70 (m, 2H), 4.51 (br. s, 1H), 2.28-2.22 (m, 4H), 1.60-1.52 (m, 4H), 1.52-

1.45 (m, 2H). $^{13}$C NMR (100 MHz, CDCl$_3$): δ 153.25, 149.15, 141.22, 128.63, 128.39, 127.29, 125.55, 115.21, 45.89, 37.50, 26.63, 23.14. LC-MS purity (UV/MS): 100/100%, R$_t$ 5.07 min, M−1: 251.62.

4-(1-(2-Fluoro-phenylcyclohexyl)phenol (ERB-003)

The title compound was prepared according to GP5 from 1-(cyclohexen-1-yl)-2-fluorobenzene (400 mg, 1.99 mmol). Yield: 0.488 g white powder. $^1$H NMR (400 MHz, CDCl$_3$): δ 7.40 (ddd, 2.3 Hz, 8.1 Hz, 8.3 Hz, 1H), 7.18-7.06 (m, 3H), 6.88 (ddd, 2.3 Hz, 8.1 Hz, 12.7 Hz, 1H), 6.74-6.69 (m, 2H), 4.51 (br. s, 1H), 2.48-2.36 (m, 2H), 2.22-2.13 (m, 2H), 1.67-1.41 (m, 6H). LC-MS purity (UV/MS): 100/100%, R$_t$ 4.98 min, M−1: 269.16.

4-(1-(3,5-Difluoro-phenylcyclohexyl)phenol (ERB-008)

The title compound was prepared according to GP5 from 1-(cyclohexen-1-yl)-3,5-difluorobenzene (400 mg, 1.99 mmol). Yield: 330 mg white powder. LC-MS purity (UV/MS): 100/100%, R$_t$ 5.08 min, M−1: 287.17.

4-(1-(3,4-Difluoro-phenylcyclohexyl)phenol (ERB-009)

The title compound was prepared according to GP5 from 1-(cyclohexen-1-yl)-3,4-difluorobenzene (400 mg, 1.99 mmol). Yield: 230 mg white powder. $^1$H NMR (400 MHz, CDCl$_3$): δ 7.18-7.12 (m, 2H), 7.12-6.95 (m, 3H), 6.84-6.76 (m, 2H), 5.44 (br. s, 1H), 2.40-2.05 (m, 4H), 1.67-1.30 (m, 6H). LC-MS purity (UV/MS): 100/98%, R$_t$ 5.08 min, M−1: 287.22.

4-[1-(2,6-Difluoro-phenyl)-cyclohexyl]-phenol (ERB-010)

The title compound was prepared according to GP5 from 1-(cyclohexen-1-yl)-2,6-difluorobenzene (200 mg, 1.0 mmol). Yield: 218 mg white powder. $^1$H NMR (400 MHz, CDCl$_3$): δ 7.24-7.18 (m, 2H), 7.18-6.98 (m, 1H), 6.82-6.76 (m, 2H), 6.72-6.68 (m, 2H), 5.48 (br. s, 1H), 2.85-2.76 (m, 2H), 1.95-1.85 (m, 2H), 1.76-1.64 (m, 2H), 1.64-1.34 (m, 4H). LC-MS purity (UV/MS): 100/100%, R$_t$ 5.08 min, M−1: 287.60.

4-(1-Phenyl-[4-(trifluoromethyl)-cyclohexyl])-phenol (ERB-030)

The title compound was prepared according to GP5 from [4-(trifluoromethyl)-1-cyclohexen-1-yl]-benzene (200 mg, 1.0 mmol). Yield: 228 mg.
ERB-030: $^1$H NMR (400 MHz, CDCl$_3$): δ 7.35-7.08 (m, 7H), 6.82-6.77 (m, 2H), 4.80 (br. s, 1H), 2.80-2.75 (m, 2H), 2.23-2.10 (m, 1H), 1.99-1.82 (m, 4H), 1.62-1.55 (m, 2H). LC-MS purity (UV/MS): 100/100 R$_t$ 9.16 min, M−1: 319.19.
Isomer of ERB-030: $^1$H NMR (400 MHz, CDCl$_3$): δ 7.38-7.15 (m, 5H), 7.10-6.98 (m, 2H), 6.72-6.64 (m, 2H), 4.67 (br. s, 1H), 2.82-2.71 (m, 2H), 2.21-2.15 (m, 1H), 2.00-1.82 (m, 4H), 1.62-1.50 (m, 2H). LC-MS purity (UV/MS): 100/100, R$_t$ 9.21 min, M−1: 319.19.

4-(1-(4-Fluorophenyl)-[4-(trifluoromethyl)-cyclohexyl])-phenol (ERB-031)

The title compound was prepared according to GP5 from 4-fluoro-[4-(trifluoromethyl)-1-cyclohexen-1-yl]-benzene (200 mg, 1.0 mmol). Yield: 221 mg.
ERB-031: $^1$H NMR (400 MHz, CDCl$_3$): δ 7.18-7.11 (m, 2H), 7.10-7.07 (m, 2H), 6.92-6.87 (m, 2H), 6.83-6.80 (m, 2H), 4.80 (br. s, 1H), 2.72-2.64 (m, 2H), 2.22-2.08 (m, 1H), 1.95-1.85 (m, 4H), 1.59-1.47 (m, 2H). LC-MS purity (UV/MS): 100/100%, R$_t$ 9.28 min, M−1: 337.17.
Isomer of ERB-031: $^1$H NMR (400 MHz, CDCl$_3$): δ 7.32-7.24 (m, 2H), 7.08-6.96 (m, 2H), 6.72-6.66 (m, 2H), 4.73 (br. s, 1H), 2.74-2.66 (m, 2H), 2.22-2.08 (m, 1H), 1.96-1.86 (m, 4H), 1.56-1.44 (m, 2H). LC-MS purity (UV/MS): 100/100%, R$_t$ 9.24 min, M−1: 337.17.

4-(1-(3-Fluorophenyl)-[4-(trifluoromethyl)-cyclohexyl])-phenol (ERB-032)

The title compound was prepared according to GP5 from 4-fluoro-[4-(trifluoromethyl)-1-cyclohexen-1-yl]-benzene (200 mg, 1.0 mmol). Yield: 221 mg. The diastereomers were separated by flash chromatography.
ERB-032: $^1$H NMR (400 MHz, CDCl$_3$) δ 7.48-7.44 (m, 1H), 7.24-7.13 (m, 2H), 7.08-7.03 (m, 2H), 6.96-6.90 (m, 1H), 6.72-6.67 (m, 2H), 4.73 (br. s, 1H), 2.94-2.86 (m, 2H), 2.20-2.08 (m, 1H), 1.98-1.90 (m, 2H), 1.88-1.78 (m, 2H), 1.60-1.48 (m, 2H). LC-MS purity (UV/MS): 100/100%, R$_t$ 9.21 min, M−1: 337.17.
Isomer of ERB-032: $^1$H NMR (400 MHz, CDCl$_3$): δ 7.26-7.21 (m, 2H), 7.18-7.11 (m, 2H), 7.05-7.00 (m, 1H), 6.90-6.85 (m, 1H), 6.80-6.76 (m, 2H), 4.78 (br. s, 1H), 2.90-2.81 (m, 2H), 2.22-2.10 (m, 1H), 2.10-1.99 (m, 2H), 1.90-1.84 (m, 2H), 1.62-1.48 (m, 2H). LC-MS purity (UV/MS): 100/100%, R$_t$ 9.28 min, M−1: 337.17.

4-[1-(2-Fluoro-phenyl)-4-isopropyl-cyclohexyl]-phenol (ERB-039)

The title compound was prepared according to GP5 from 1-fluoro-2-[4-(1-i-propyl)-1-cyclohexen-1-yl]-benzene (200 mg, 1.0 mmol). Yield: 180 mg. The diastereomers were separated by flash chromatography
ERB-039: $^1$H NMR (400 MHz, CDCl$_3$): δ 7.68-7.52 (m, 1H), 7.24-7.10 (m, 2H), 7.10-7.04 (m, 2H), 6.95-6.86 (m, 1H), 6.71-6.64 (m, 2H), 4.66 (br. s, 1H), 2.84-2.75 (m, 3H), 1.90-1.73 (m, 4H), 1.40-1.25 (m, 3H), 0.83 (d, 6H, 7 Hz). LC-MS purity (UV/MS): 100/100%, R$_t$ 6.10 min, M−1: 311.51.
Isomer of ERB-039: $^1$H NMR (400 MHz, CDCl$_3$) δ 7.30-7.22 (m, 3H), 7.17-7.08 (m, 1H), 7.07-7.00 (m, 1H), 6.90-6.80 (m, 1H), 6.78-6.74 (m, 2H), 4.58 (br. s, 1H), 2.82-2.74 (m, 2H), 2.04-1.93 (m, 2H), 1.70-1.64 (m, 2H), 1.38-1.12 (m, 4H), 0.83 (d, 6H, 7 Hz). LC-MS purity (UV/MS): 100/86%, R$_t$ 6.16 min, M−1: 311.52.

4-[1-(3-Fluoro-phenyl)-4-isopropyl-cyclohexyl]-phenol (ERB-037)

The title compound was prepared according to GP5 from 1-fluoro-3-[4-(1-i-propyl)-1-cyclohexen-1-yl]-benzene (200 mg, 1.0 mmol). Yield: 150 mg. The diastereomers were separated by flash chromatography
ERB-037: $^1$H NMR (400 MHz, CDCl$_3$): δ 7.24-7.18 (m, 2H), 7.18-7.12 (m, 1H), 6.96-6.92 (m, 1H), 6.89-6.84 (m, 1H), 6.82-6.74 (m, 3H), 4.66 (br. s, 1H), 2.64-2.58 (m, 2H), 1.92-1.82 (m, 2H), 1.73-1.65 (m, 2H), 1.38-1.13 (m, 4H), 0.82 (d, 6H, 7 Hz). LC-MS purity (UV/MS): 100/-, R$_t$ 6.87 min, M−1: 311.
Isomer of ERB-037: $^1$H NMR (400 MHz, CDCl$_3$) δ 7.29-7.20 (m, 1H), 7.14-7.10 (m, 1H), 7.08-7.00 (m, 3H), 6.88-6.81 (m, 1H), 6.70-6.64 (m, 2H), 4.58 (br. s, 1H), 2.66-2.58

4-[4-Isopropyl-1-(3-methoxy-phenyl)-cyclohexyl]-phenol (ERB-038)

The title compound was prepared according to GP5 from 1-methoxy-3-[4-(1-i-propyl)-1-cyclohexen-1-yl]-benzene (200 mg, 1.0 mmol). The diastereomers were separated by flash chromatography ERB-038: $^1$H NMR (400 MHz, CDCl$_3$): δ 7.28-7.20 (m, 2H), 7.08-7.02 (m, 2H), 6.96-6.92 (m, 1H), 6.73-6.62 (m, 3H), 4.58 (br. s, 1H), 3.80 (s, 3H), 2.68-2.60 (m, 2H), 1.94-1.82 (m, 2H), 1.38-1.08 (m, 4H), 0.82 (d, 6H, 7 Hz). LC-MS purity (UV/MS): 100/100, R$_t$ 6.87 min, M−1: 323.

Isomer of ERB-038: $^1$H NMR (400 MHz, CDCl$_3$) δ 7.29-7.20 (m, 3H), 7.19-7.10 (m, 1H), 6.80-6.72 (m, 3H), 6.68-6.60 (m, 1H), 4.60 (br. s, 1H), 3.74 (s, 3H), 2.66-2.58 (m, 2H), 1.94-1.83 (m, 2H), 1.38-1.05 (m, 4H), 0.80 (d, 6H, 7 Hz). LC-MS purity (UV/MS): 100/100%, R$_t$ 6.16 min, M−1: 323.

4-(1-Phenyl-cycloheptyl)-phenol (ERB-012)

The title compound was prepared according to GP5 with a yield of 40%-70%. LC-MS purity (UV/MS): 100/100%, R$_t$ 5.35 min. $^1$H-NMR (400 MHz, CDCl$_3$) δ 7.28-7.10 (m, 5H), 7.04 (d, 2H, J=8.8 Hz), 6.70 (d, 2H, J=8.8 Hz), 4.55 (s, 1H), 2.35-2.20 (m, 4H), 1.78-1.60 (m, 4H), 1.60-1.50 (m, 4H).

4-[1-(4-Fluoro-phenyl)-cycloheptyl]-phenol (ERB-013)

The title compound was prepared according to GP5 with a yield of 40%-70%. LC-MS purity (UV/MS): 100/100%, R$_t$ 9.89 min. $^1$H-NMR (400 MHz, CDCl$_3$) δ 7.15 (m, 2H), 7.01 (d, 2H, J=8.7 Hz), 6.95 (m, 2H), 6.75 (d, 2H, J=8.7 Hz), 4.55 (br. s, 1H), 2.30-2.20 (m, 4H), 1.75-1.40 (m, 8H).

4-[1-(4-Fluoro-phenyl)-cycloheptyl]-benzene-1,2-diol (ERB-014)

The title compound was prepared according to GP5 with a yield of 40%-70%. LC-MS purity (UV/MS): 86/100%, R$_t$ 9.05 min. $^1$H-NMR (400 MHz, CDCl$_3$) δ 7.17-7.10 (m, 2H), 6.96-6.70 (m, 3H), 6.60 (m, 2H), 5.15-4.85 (m, 2-3H), 2.30-2.10 (m, 4H), 1.70-1.40 (m, 8H).

4-[1-(3-Fluoro-phenyl)-cycloheptyl]-phenol (ERB-015)

The title compound was prepared according to GP5 with a yield of 40%-70%. LC-MS purity (UV/MS): 99/93%, R$_t$ 9.88 min. $^1$H-NMR (400 MHz, CDCl$_3$) δ 7.30-6.68 (m, 4H), 7.12 (d, 2H, J=8.8 Hz), 6.74 (d, 2H, J=8.8 Hz), 4.55 (s, 1H), 2.26 (m, 1H), 2.0 (m, 1H), 1.72-1.50 (m, 8H), 1.30-1.10 (m, 2H).

4-[1-(2-Fluoro-phenyl)-cycloheptyl]-phenol (ERB-016)

The title compound was prepared according to GP5 with a yield of 40%-70%. $^1$H-NMR (400 MHz, CDCl$_3$) δ 7.44 (m, 1H), 7.22-7.10 (m, 1H), 7.02 (d, 2H, J=8.8 Hz), 6.92-6.86 (m, 1H), 6.70 (d, 2H, J=8.8 Hz), 4.51 (s, 1H), 2.42-2.26 (m, 4H), 1.82-1.52 (m, 8H). $^{13}$C-NMR (100 MHz, CDCl$_3$) δ 161.7 (d, J=249 Hz), 153.2, 143.2, 137.4 (d, J=11 Hz), 128.0 (d, J=5 Hz), 127.9 (d, J=9 Hz), 127.7 (2C), 123.5 (d, J=3 Hz), 116.8 (d, J=24 Hz), 114.9 (2C), 48.7 (d, J=2 Hz), 39.4 (d, J=2 Hz), 30.6, 24.6.

4-(1-Phenyl-cyclooctyl)-phenol (ERB-017)

The title compound was prepared according to GP5 with a yield of 40%-70%. $^1$H-NMR (400 MHz, CDCl$_3$) δ 7.26-7.10 (m, 5H), 7.09 (d, 2H, J=8.8 Hz), 6.71 (d, 2H, J=8.8 Hz), 2.34-2.28 (m, 4H), 1.68-1.54 (m, 6H), 1.46-1.38 (m, 4H).

4-(1-Phenyl-cycloheptyl)-benzene-1,2-diol (ERB-035)

The title compound was prepared according to GP5 with a yield of 40%-70%. $^1$H-NMR (400 MHz, CDCl$_3$) δ 7.28-7.10 (m, 5H), 6.76-6.72 (m, 1H), 6.67-6.63 (m, 2H), 4.90 (bs, 1H), 2.30-2.10 (m, 4H), 1.8-1.4 (m, 8H).

2-Methyl-4-[1-(3-Fluoro-phenyl)-cycloheptyl]-phenol (ERB-036)

The title compound was prepared according to GP5 with a yield of 40%-70%. LC-MS purity (UV/MS): 94/100%, R$_t$ 10.37 min.

4-(1-(2,4-Difluoro-phenyl)-cyclohexyl)-phenol (ERB-011)

The title compound was prepared according to GP5 with a yield of 40%-70%. $^1$H-NMR (400 MHz, CDCl$_3$) δ 7.34 (m, 1H), 7.12 (d, 2H, J=8.4 Hz), 6.82 (m, 1H), 6.72 (d, 2H, J=8.4 Hz), 6.64 (m, 1H), 4.50 (s, 1H), 2.36 (m, 2H), 2.18 (m, 2H), 1.66-1.40 (m, 6H).

4-(1-(2,5-Difluoro-phenyl)-cyclohexyl)-phenol (ERB-044)

The title compound was prepared according to GP5 with a yield of 40%-70%. $^1$H-NMR (400 MHz, CDCl$_3$) δ 7.14 (d, 2H, J=8.8 Hz), 7.14-7.06 (m, 1H), 6.83 (m, 2H), 6.73 (d, 2H, J=8.0 Hz), 4.50 (s, 1H), 2.35 (m, 2H), 2.20 (m, 2H), 1.66-1.40 (m, 6H).

4-(1-(2-Fluoro-5-chloro-phenyl)-cyclohexyl)-phenol (ERB-045)

The title compound was prepared according to GP5 with a yield of 40%-70%. $^1$H-NMR (400 MHz, CDCl$_3$) δ 7.38 (dd, 1H, J=8.0 Hz, 4.4 Hz), 7.17-7.09 (m, 1H), 7.14 (d, 2H, J=8.4 Hz), 6.86-6.74 (m, 1H), 6.73 (d, 2H, J=8.4 Hz), 4.58 (s, 1H), 2.33 (m, 2H), 2.21 (m, 2H), 1.54 (m, 6H).

Example 8 tert-Butyl 1-((4-(1-phenylcyclohexyl)phenoxy)carbonyl)-2-methylpropylcarbamate

To a stirred solution at room temperature of 4-(1-phenyl-cyclohexyl)phenol (311 mg, 1.23 mmol) in dry THF (2 mL) was added BocValOH (295 mg, 1.36 mmol) dissolved in THF (2 mL). A solution of DIC (231 μL; 1.48 mmol) in THF (2 mL) was added drop wise, which caused precipitation after a few minutes. After 5 min DMAP (166 mg; 1.36 mmol) was added and stirring was continued for 19 h. The reaction mixture was concentrated in vacuo and purified by flash chromatography (eluent: EtOAc (0-10%) in heptane) affording 517 mg (1.14 mmol; 93%) of colourless oil. LC-MS purity (UV/MS): 100/100%, $R_t$ 6.77 min, M+18: 469.53.

Example 9

4-(1-Phenylcyclohexyl)phenyl 2-amino-3-methylbutanoate

To a stirred solution at room temperature of tert-butyl 1-((4-(1-phenylcyclohexyl)phenoxy)carbonyl)-2-methyl-propylcarbamate (142 mg, 0.31 mmol) in dry DCM (3 mL) was added TFA (300 µL), which caused gas evolution. Stirring was continued. After 1 h the reaction mixture was concentrated in vacuo to afford 96 mg (0.21 mmol; 67%) of colourless oil. LC-MS purity (UV/MS): 92/97%, $R_t$ 5.45 min, M+1: 352.49. $^1$H NMR (400 MHz, CDCl$_3$): 11.12 (br s), 7.76 (br s), 7.29 (d, 2H, J=8.8 Hz), 7.27 (d, 4H, J=4.8 Hz), 7.13-7.16 (m, 1H), 6.95 (d, 2H, J=8.8 Hz), 6.16 (d, 1H, J=4.0 Hz), 2.40-2.48 (m, 1H), 2.18-2.33 (m, 4H), 1.50-1.58 (m, 6H), 1.05-1.08 (m, 6H).

Example 10

2-(2-tert-Butoxycarbonylamino-3-methyl-butyrylamino)-3-methyl-butyric acid 4-(1-phenyl-cyclohexyl)-phenyl ester To a stirred mixture at room temperature of PS-carbodiimide (1.2 g; 1.32 mmol) and 4-(cyclohexyl-phenyl)methyl-hydroxybenzene (152 mg, 0.60 mmol) in dry THF (2 mL) was added BocValValOH (285 mg, 0.90 mmol) dissolved in THF (2 mL). After 5 min, DMAP (81 mg; 0.66 mmol) was added and stirring was continued for 47 h. The reaction mixture was filtered and concentrated in vacuo and purified by CC using EtOAc (0-25%) in heptane affording 297 mg (0.54 mmol; 90%) of colourless oil. LCMS purity (UV/MS): 89/100%, $R_t$ 7.61 min, M+1: 551.53.

Example 11

2-(2-Amino-3-methyl-butyrylamino)-3-methyl-butyric acid 4-(1-phenyl-cyclohexyl)-phenyl ester To a stirred solution at room temperature of 4'-(cyclohexyl)-(phenyl)methyl-1'-(2-tert-butoxycarbonylamino-2-[2-methyl]ethyl)acetoxybenzene (297 mg, 0.54 mmol) in dry DCM (3 mL) was added TFA (300 µL), which caused gas evolution. Stirring was continued. After 1 h the reaction mixture was concentrated in vacuo to afford 240 mg (0.43 mmol; 79%) of colourless oil as a mixture of isomers. LCMS purity (UV/MS): 100/98%, $R_t$ 4.64/4.95 min, M+1: 451.56. $^1$H NMR (400 MHz, CDCl$_3$): 8.52 (br s), 7.63 (br s), 7.26-7.29 (m, 13H), 7.12-7.16 (m, 1H), 7.06 (d, 1H, J=7.6 Hz), 6.95 (d, 1H, J=8.8 Hz), 6.92 (d, 1H, J=8.8 Hz), 4.71-4.74 (m, 1H), 4.60-4.63 (m, 1H), 4.17-4.21 (m, 2H), 2.44 (m, 1H), 2.16-2.41 (m, 12H), 1.47-1.57 (m, 12H), 0.98-1.05 (m, 24H).

Example 12

2-Iodo-4-(1-phenyl-cyclohexyl)-phenol (ERB-026)

4-(1-Phenyl-cyclohexyl)-phenol (600 mg, 2.38 mmol) was dissolved in acetic acid (10 mL). N-iodosuccinimide (537 mg, 2.38 mmol) was added. The mixture was stirred for 4 h., concentrated and worked-up on the combiflash (10 g column, 0-10% ethyl acetate in heptane). 718 mg (80%) of the desired product, 90 mg (7.5%) of 2,6-diiodo-4-(1-phenyl-cyclohexyl)-phenol and 20 mg (3%) of starting material were isolated.
$^1$H NMR (400 MHz, CDCl$_3$): 7.58 (d, 1H, J=2.4 Hz), 7.34-7.24 (m, 4H), 7.19-7.14 (m, 1H), 7.12 (dd, 1H, J=2.4 Hz, J=8.6 Hz), 6.88 (d, 1H, J=8.6 Hz), 5.18 (br. s, 1H), 2.23-2.15 (m, 4H), 1.62-1.44 (m, 6H).

Example 13

2-Iodo-1-methoxy-4-(1-phenyl-cyclohexyl)-benzene

NaH (60% in mineral oil, 60 mg, 1.50 mmol) was added an ice-cooled solution of 2-iodo-4-(1-phenyl-cyclohexyl)-phenol (400 mg, 1.06 mmol) in DMF (10 mL). Methyl iodide (125 µL, 2.0 mmol) was added. The reaction temperature was allowed to reach room temperature. The mixture was stirred for 2 h, then quenched with water 10 mL and extracted with dichloromethane (2×20 mL). The combined organic phase was dried (Na$_2$SO$_4$) and concentrated in vacuo. The residue was taken up in water (20 mL) and extracted with dichloromethane. The organic phase was dried (Na$_2$SO$_4$) and concentrated in vacuo. $^1$H-nmr of the syrup (430 mg) indicated full conversion to the methyl ether. $^1$H NMR (400 MHz, CDCl$_3$): 7.71 (d, 1H, J=2.1 Hz), 7.32-7.25 (m, 4H), 7.18 (dd, 1H, J=2.1 Hz, J=8.8 Hz), 7.17-7.13 (m, 1H), 6.72 (d, 1H, J=8.8 Hz), 3.83 (s, 3H), 2.32-2.18 (m, 4H), 1.62-1.44 (m, 6H).

Example 14

2-Fluoro-1-methoxy-4-(1-phenyl-cyclohexyl)-benzene

A solution of n-butyl lithium in hexane (1 mL, 1.6 M, 1.6 mmol) was added dropwise to a solution of 2-iodo-1-methoxy-4-(1-phenyl-cyclohexyl)-benzene (200 mg, 0.51 mmol) and N-fluoro-benzenesulfonimide (320 mg, 1.02 mmol) in dry THF (5 mL) at −78° C. under an argon atmosphere. The mixtures was stirred at −78° C. for 2 h. A GC run after 1 h and 2 h indicated no further conversion of the starting material. A saturated solution of NH$_4$Cl (10 mL) was added. The mixture was extracted with dichloromethane (2×20 mL), the combined organic phase was dried (Na$_2$SO$_4$) and concentrated in vacuo and worked-up by flash-chromatography. The desired product was isolated in an approx. 75% purity according to a $^1$H nmr spectrum of the isolated mixture. The mixture was used without further purification in the next reaction.
$^1$H NMR (400 MHz, CDCl$_3$): 7.32-7.24 (m, 4H), 7.20-7.11 (m, 1H), 7.04-6.95 (m, 1H), 7.02-6.94 (m, 2H), 6.89-6.84 (m, 1H), 3.85 (s, 3H), 2.32-2.18 (m, 4H), 1.61-1.50 (m, 6H).

Example 15

2-Fluoro-4-(1-phenyl-cyclohexyl)-phenol (ERB-006)

A solution of the crude 2-fluoro-1-methoxy-4-(1-phenyl-cyclohexyl)-benzene in dichloromethane (100 mg, 0.25 mmol, 2 mL) was added to a solution of borane tribromide in dichloromethane (1 M, 0.25 ml, 025 mmol) at −78° C. under an argon atmosphere and stirred at r.t for 3 h. Water (10 mL) was added and the mixture was extracted with dichloromethane (2×10 mL). The combined organic phase was dried (Na$_2$SO$_4$) and concentrated to a syrup. Work-up by flash-chromatography (eluent: 30→80% dichloromethane in heptane) gave the title product in a yield of 50 mg.
LC-MS purity (UV/MS): 100/100%, $R_t$ 5.15/5.19 min, M−1: 269.6. $^1$H NMR 7.31-7.24 (m, 5H), 7.17-7.12 (m, 1H), 6.96 (ddd, 1H, J=2.0 Hz, J=12.9 Hz, J=14.7 Hz.), 6.91 (dd, 1H, J=8.4 Hz, J=17.1 Hz), 4.98 (br. s, 1H), 2.28-2.18 (m, 4H), 1.61-1.48 (m, 6H).

Example 16

1-Methoxy-4-(1-phenyl-cyclohexyl)-benzene, procedure A

A mixture of $AuCl_3$ (7.6 mg, 0.025 mmol) and AgOTf (19.3 mg, 0.075 mmol) was stirred in dichloromethane (2 mL) for 30 min. Anisole (54 mg, 0.5 mmol) and 1-Phenyl-1-cyclohexene (158 mg, 1 mmol) were then added sequentially. The resulting mixture was stirred at room temperature overnight. Evaporation of the solvent under reduced pressure gave 130 mg of crude material. Flash chromatography (heptane:ethyl acetate 95:5) afforded 90 mg of a as a colorless oil. $R_f$=0.33 (heptane:ethyl acetate 95:5). $^1$H-NMR (400 MHz, $CDCl_3$) δ 7.27-7.25 (m, 4H), 7.19 (d, 2H, J=8.8 Hz), 7.12 (m, 1H), 6.81 (d, 2H, J=8.8 Hz), 3.77 (s, 3H), 2.30-2.20 (m, 4H), 1.62-1.44 (m, 6H). $^{13}$C-NMR (100 MHz, $CDCl_3$) δ 157.4, 149.2, 140.9, 128.4 (two carbons), 128.4 (two carbons), 127.3 (two carbons), 125.5, 113.8 (two carbons), 55.4, 45.9, 37.5 (two carbons), 26.7, 23.2 (two carbons).

Example 17

1-Methoxy-4-(1-phenyl-cyclohexyl)-benzene (B), procedure B 4-(1-phenylcyclohexyl)phenol (20 mg, 0.08 mmol) was dissolved in DMF (2 mL). A suspension of NaH in oil (60%, 5 mg, 0.125 mmol) was added. After stirring for 5 minutes methyl iodide (0.05 mL; 0.8 mmol) was added. The reaction mixture was stirred for 2 h. (tic indicated full conversion of the starting material) then quenched with water (10 mL). Dichloromethane (10 mL) was added. The mixture was shaken and the organic phase separated off, dried ($Na_2SO_4$) and concentrated to syrup. The title product was afforded after work-up by flash-chromatography (eluent dichloromethane). Yield: 20 mg, quantitatively. LC-MS purity (UV/MS): 100/-, $R_t$ 6.48 min. $^1$H NMR data were in accordance with the data written above.

Example 18

Acetic acid 4-(1-phenyl-cyclohexyl)-phenyl ester 4-(1-phenylcyclohexyl)phenol (100 mg, 0.40 mmol) was dissolved in dichloromethane (5 mL). Pyridine (1 mL) and the acylating reagent were added (1.60 mmol, 5 equiv.). The reaction mixture was stirred for 2 h. at room temperature (tic indicated full conversion of the starting material) then quenched with water (10 mL). Dichloromethane (10 mL) was added. The mixture was shaken and the organic phase separated off, dried ($Na_2SO_4$) and concentrated to syrup. The acylated product was afforded after flushing the product through a block of silica (eluent dichloromethane) Yield 120 mg, isolated as a crystalline product. $^1$H-NMR (400 MHz, $CDCl_3$) δ 7.30-7.24 (m, 6H), 7.17-7.10 (m, 1H), 7.01-6.96 (m, 2H), 2.36-2.19 (m, 7H), 1.62-1.45 (m, 6H).

Example 19

2,2-Dimethyl-propionic acid 4-(1-phenyl-cyclohexyl)-phenyl ester 4-(1-phenylcyclohexyl)phenol (100 mg, 0.40 mmol) was dissolved in dichloromethane (5 mL). Pyridine (1 mL) and the acylating reagent were added (1.60 mmol, 5 equiv.). The reaction mixture was stirred for 2 h. at room temperature (tlc indicated full conversion of the starting material) then quenched with water (10 mL). Dichloromethane (10 mL) was added. The mixture was shaken and the organic phase separated off, dried ($Na_2SO_4$) and concentrated to syrup. The acylated product was afforded after flushing the product through a block of silica (eluent dichloromethane) Yield: 110 mg, isolated as crystalline product $^1$H-NMR (400 MHz, $CDCl_3$) δ 7.29-7.23 (m, 6H), 7.16-7.10 (m, 1H), 6.98-6.93 (m, 2H), 2.34-2.20 (m, 4H), 1.61-1.45 (m, 6H), 1.33 (s, 9H).

Example 20

Dimethyl-sulfamic acid 4-(1-phenyl-cyclohexyl)-phenyl ester

DMAP (20 mg, 0.16 mmol) and dimethylcarbamoylchloride (568 mg, 4.0 mmol) was added sequentially to a mixture of 4-(1-phenylcyclohexyl)phenol (200 mg, 0.79 mmol) and $Et_3N$ (400 mg, 4.0 mmol) in $CH_2Cl_2$ (10 mL). The resulting mixture was stirred at room temperature overnight. The solution was further washed with 2M HCL (aq) (20 mL), water (20 mL), saturated $NaHCO_3$ (20 mL) and water (20 mL) and dried over $Na_2SO_4$. Evaporation of the solvent under reduced pressure gave 180 mg of crude material. Flash chromatography (heptane:ethyl acetate 95:5) afforded 120 mg (42%) of a as a slightly yellowish oil. $R_f$=0.21 (heptane:ethyl acetate 90:10). $^1$H-NMR (400 MHz, $CDCl_3$) δ 7.30-7.12 (m, 7H), 7.17 (d, 2H, J=9.2 Hz), 2.94 (s, 6H), 2.34-2.18 (m, 4H), 1.66-1.44 (m, 6H). $^{13}$C-NMR (100 MHz, $CDCl_3$) δ 148.2, 148.0, 147.7, 128.8 (two carbons), 128.5 (two carbons), 127.4 (two carbons), 125.8, 121.4 (two carbons), 46.3, 39.0 (two carbons), 37.4 (two carbons), 26.5, 23.0 (two carbons).

Example 21

Phosphoric acid dibenzyl ester 4-(1-phenyl-cyclohexyl)-phenyl ester 1H-tetrazole (6 g of a 3% solution in $CH_3CN$, 2.6 mmol) was added to a stirred solution of 4-(1-phenylcyclohexyl)phenol (200 mg, 0.79 mmol) and dibenzyl-N,N-diisopropyl phosphoramidite (575 mg, 1.7 mmol) in $CH_2Cl_2$ (10 mL). After 30 min, the mixture was cooled to 0° C. and m-CPBA (570 mg, 2.3 mmol, 70%) was added. The mixture was stirred for 40 min, washed with 10% aqueous $Na_2S_2O_3$ and $NaHCO_3$ (saturated), dried over $Na_2SO_4$, filtered and the solvent was evaporated under reduced pressure. Flash chromatography (heptane:ethyl acetate 80:20) afforded 90 mg of a as a colorless oil. $R_f$=0.58 (heptane:ethyl acetate 50:50). $^1$H-NMR (400 MHz, $CDCl_3$) δ 7.34-7.10 (m, 15H), 7.19 (d, 2H, J=8.8 Hz), 7.04 (d, 2H, J=8.8 Hz), 5.04 (d, 2H, J=8.4 Hz), 5.04 (d, 2H, J=8.4 Hz), 2.32-2.18 (m, 4H), 1.60-1.46 (m, 6H). $^{13}$C-NMR (100 MHz, $CDCl_3$) δ 151.6, 148.4 (d, J=15 Hz), 145.7, 135.8 (two carbons, d, J=8.6 Hz), 128.8 (two carbons), 128.8 (four carbons), 128.7 (two carbons), 128.5 (two carbons), 128.2 (four carbons), 127.3 (two carbons), 125.7, 119.8 (two carbons, d, J=4.9 Hz), 70.1 (two carbons, d, J=5.7 Hz), 46.1, 37.4 (two carbons), 26.5, 23.1 (two carbons).

Example 22

Phosphoric acid mono-[4-(1-phenyl-cyclohexyl)-phenyl]ester

A mixture of phosphoric acid dibenzyl ester 4-(1-phenylcyclohexyl)-phenyl ester (133 mg, 2.6 mmol) and 10% palladium on carbon (100 mg) in EtOAc (10 mL) was stirred under H$_2$ (one atmosphere) for two hours. The mixture was filtered through a pad of Celite, and the solvent was evaporated under reduced pressure to yield 79 mg (92%) of a colourless semisolid. R$_f$=0.22 (CHCl$_3$:MeOH:H$_2$O 65:25:4). $^1$H-NMR (400 MHz, CDCl$_3$) δ 7.40-6.90 (m, 9H), 2.30-2.00 (m, 4H), 1.60-1.30 (m, 6H).

Example 23

(4-Benzyloxy-phenyl)-phenyl-methanone

NaH (60% in mineral oil, 1.2 g, 30 mmol) was added to an ice-cooled solution of (4-hydroxy-phenyl)-phenyl-methanone (5 g, 25.2 mmol) in DMF (25 mL). Stirred for 20 minutes at room temperature. Benzyl bromide (6.1 ml, 50 mmol) was added at 0° C. The reaction temperature was raised to room temperature after 1 h. Stirred 2 h. Water (20 mL) was added and aqueous phase was extracted dichloromethane (2×30 mL). The combined organic phase was concentrated and purified by flash chromatography (eluent: dichloromethane). $^1$H nmr revealed the product was pure. Yield: 7.0 g, 96%

$^1$H NMR (400 MHz, CDCl$_3$): 7.83 (d, 2H, J=8.4 Hz), 7.77 (d, 2H, J=7.2 Hz), 7.58-7.52 (m, 1H), 7.50-7.32 (m, 6H), 7.03 (d, J=8.4 Hz), 5.17 (s, 2H).

Example 24

1-(1-Allyloxy-1-phenyl-but-3-enyl)-4-benzyloxy-benzene

A solution of allylmagnesium bromide in diethyl ether (1 M, 15 ml) was added to an ice water cooled solution of the (4-benzyloxy-phenyl)-phenyl-methanone (4.0 g, 13.87 mol) in THF (20 mL). The mixture was stirred for 1 h at r.t, and then quenched with water (20 mL). The aqueous phase was extracted with dichloromethane (2×30 ml). The combined organic phase was dried (Na$_2$SO$_4$) and concentrated to syrup. The crude was dissolved in DMF (10 mL) cooled in an ice-water bath. NaH (600 mg, appr. 15 mmol) was added and the mixture was stirred for ½ h. Allylbromide (1.25 mL, 15.0 mmol) was added and the mixture was stirred at 40° C. for 1 h. Water (20 mL) was added and aqueous phase was extracted dichloromethane (2×30 mL). The combined organic phase was concentrated. Purification using the combiflash (10 g, column, 0-10 ethyl acetate in heptane) gave the diene in an yield of 4.2 g (81%).

$^1$H NMR (400 MHz, CDCl$_3$): 7.53-7.26 (m, 12H), 6.98 (d, 2H, J=8.6 Hz), 6.05-5.94 (m, 1H), 5.78-5.65 (m, 1H), 5.47-5.39 (m, 1H), 5.24-5.03 (m, 5H), 3.84-3.80 (m, 2H), 3.22-3.17 (m, 2H).

Example 25

2-(4-Benzyloxy-phenyl)-2-phenyl-3,6-dihydro-2H-pyran 1-(1-Allyloxy-1-phenyl-but-3-enyl)-4-benzyloxy-benzene (4.2 g, 10.1 mmol) was dissolved in dichloromethane (50 mL) and bis(tricyclohexylphosphine)benzylidene ruthenium (IV) dichloride (25 mg, 0.03 mmol) was added. Stirred at r.t. for 1 h. TLC indicated full conversion of the starting material. A solution of methylamine in THF (1 M, 1 mL) was added. The solution was eluted through a block of silica. The silica was washed with a solution of dichloromethane and ethyl acetate (1:1, 100 mL). The combined organic phase was concentrated to slightly coloured syrup (4.1 g, quantitatively).

$^1$H NMR (400 MHz, CDCl$_3$): 7.46-7.24 (m, 12H), 6.95 (d, 2H, J=8.8 Hz), 6.05-5.98 (m, 1H), 5.72-5.65 (m, 1H), 4.16-4.00 (m, 2H), 2.90-2.76 (m, 2H).

Example 26

4-(2-Phenyl-tetrahydro-pyran-2-yl)-phenol 2-(4-Benzyloxy-phenyl)-2-phenyl-3,6-dihydro-2H-pyran (4.1 g) was dissolved in methanol (25 mL) and ethyl acetate (5 mL). 5% Palladium on carbon (10 mg) was added. Nitrogen was bubbled through the solution. Ammonium acetate (4 g) was added. The mixture was stirred for 6 h, filtered through a block of celite and concentrated to a solid. NMR indicated full conversion to the title product (3.1 g, 12.2 mmol).

$^1$H NMR (400 MHz, CDCl$_3$): 7.39-7.16 (m, 7H), 6.78-6.73 (m, 2H), 3.71 (t, 2H, J=5.4 Hz), 2.26 (ddd, 2H, J=2.6 Hz, J=5.4 Hz, 9.2 Hz), 1.76-1.70 (2H, m), 1.64-1.57 (m, 2H).

Example 27

Acetic acid
4-(2-phenyl-tetrahydro-pyran-2-yl)-phenyl ester 4-(2-Phenyl-tetrahydro-pyran-2-yl)-phenol (500 mg, 2 mmol) was dissolved in pyridine (10 mL). Acetic anhydride (1 mL) was added at drop wise at 0° C. The reaction temperature was allowed to raise to room temperature. After 1 h the reaction was quenched the addition of water (5 mL). Dichloromethane (20 mL) was added. The organic phase was washed with aqueous HCl (1M, 2×10 mL), brine (10 mL), dried (Na$_2$SO$_4$) and concentrated in vacuo. Purified on a short column (eluent: dichloromethane). Yield: 560 mg.

$^1$H NMR (400 MHz, CDCl$_3$): 7.39-7.66 (m, 2H), 7.32-7.19 (m, 5H), 7.02-7.00 (m, 2H), 3.73-3.69 (m, 2H), 2.25 (s, 3H), 1.73 (t, 2H, J=6 Hz), 1.65-1.57 (2H, m), 1.30-1.25 (m, 2H).

Example 28

Enzymatic Resolution

Acetic acid 4-(2-phenyl-tetrahydro-pyran-2-yl)-phenyl ester (50 mg, 0.17 mmol) was dissolved in a mixture of isopropylether (0.5 mL) and THF (0.2 mL). Phosphate buffer (100 mmol, pH=7, 2 mL) and Amono Lipase AK, from *Pseudomonas Fluorescens* (50 mg) were added. Stirred at room temperature for 2 h. The mixture was filtered, dichloromethane (10 mL) was added. The organic phase was washed with water (10 mL), dried (Na$_2$SO$_4$) and concentrated in vacuo. Chiral LC-MS indicated that 4-(2-phenyl-tetrahydro-pyran-2-yl)-phenol was formed in an ee of 71%, the absolute configuration of the enantiomer was not determined.

Example 29

4-Phenyl-3,6-dihydro-2H-pyridine-1-carboxylic acid 9H-fluoren-9-ylmethyl ester

4-Phenyl-1,2,3,6-tetrahydropyridine (200 mg, 1.26 mmol) was dissolved in dry acetonitrile (5 mL) and cooled in ice-water bath. N-(9-Fluoroenylmethoxycarbonyloxy)-succinimide (475 mg, 1.4 mmol) was added. Stirred over night at room temperature. TLC indicated full conversion of the starting material. An aqueous solution of saturated NaHCO$_3$ (5 mL) was added and the mixture was extracted with dichloromethane (2×20 mL). The combined organic phase was dried (Na$_2$SO$_4$) and concentrated in vacuo. The product was isolated after column chromatography (gradient dichloromethane→ethylacetate). Yield: 390 mg. The product was pure according to $^1$H nmr.

$^1$H NMR (400 MHz, CDCl$_3$): 7.79 (d, 2H, J=7.4 Hz), 7.63 (d, 2H, J=7.4 Hz), 7.44-7.25 (m, 9H), 6.07 (br. s, 1H), 4.49 (d, 2H, J=6.9 Hz), 4.30 (t, 1H, J=6.9 Hz), 4.16 (br. s, 2H), 3.72 (br. s, 2H), 2.55 (br. s, 2H).

Example 30

4-(4-Hydroxy-phenyl)-4-phenyl-piperidine-1-carboxylic acid 9H-fluoren-9-ylmethyl ester 4-Phenyl-3,6-dihydro-2H-pyridine-1-carboxylic acid 9H-fluoren-9-ylmethyl ester (200 mg, 0.52 mmol) was treated with a drop of BF$_3$*H$_3$PO$_4$ and phenol (200 mg, 2.1 mmol) at 60° C. for 6 h. Water (10 mL) was added and aqueous phase was extracted dichloromethane (2×10 mL). The combined organic phase was concentrated. $^1$H nmr indicated full conversion of the starting material. The desired product was isolated after flash chromatography. Yield: 270 mg. LC/MS purity (UV/MS): 96/91%, R$_t$ 7.32 min. M+1: 432.

$^1$H NMR (400 MHz, CDCl$_3$): 7.76 (d, 2H, J=7.2 Hz), 7.58 (d, 2H, J=7.2 Hz), 7.42-7.15 (m, 9H), 7.13-7.08 (m, 2H), 6.80-6.75 (m, 2H), 4.45 (d, 2H, J=6.7 Hz), 4.23 (t, 1H, J=6.7 Hz), 3.52 (br. s, 4H), 2.30 (br. s., 4H).

Example 31

4-(4-Phenyl-piperidin-4-yl)-phenol 4-(4-Hydroxy-phenyl)-4-phenyl-piperidine-1-carboxylic acid 9H-fluoren-9-ylmethyl ester (270 mg, 0.57 mmol) was treated with a solution of piperidine in DMF (20%, 5 mL) for 2 h. TLC indicated full conversion of the starting material. Concentrated in vacuo to a solid. Worked-up by flash chromatography. LC-MS indicated formation of a complex mixture. The title product was isolated in an analytical amount. LC/MS purity (UV/MS): 90/90%, R$_t$ 3.15 min. M+1: 254

$^1$H NMR (400 MHz, CD$_3$OD): 7.30-7.29 (m, 4H), 7.19-7.13 (m, 3H), 6.78-6.74 (m, 2H), 4.58 (br s, 3H), 3.21 (t, 4H, J=5.8 Hz), 2.66-2.62 (m, 4H).

Example 32

4-(4-Phenyl-tetrahydro-pyran-4-yl)-phenol

4-Phenyl-tetrahydro-pyram-4-ol (20 mg) and phenol (100 mg) were melted and FeCl$_3$ (few crystals) was added. The mixture was stirred at 50° C. for ½ h. GC-MS indicated full conversion to the desired compound. TLC revealed formation of a compound with an R$_f$ value just below phenol (eluent: dichloromethane Phenol, R$_f$=0.28, product, R$_f$=0.26).

Dichloromethane (10 mL) was added. The organic phase was washed with water (10 mL), dried (Na$_2$SO$_4$) and concentrated in vacuo. Purified by flash chromatography (eluent 5% ethyl acetate in dichloromethane→25% ethyl acetate in dichloromethane). Yield: 32 mg. LC/MS purity (UV/MS): 100/100%, R$_t$ 2.98 min. M−1: 253

$^1$H NMR (400 MHz, CD$_3$OD): 7.29-7.22 (m, 4H), 7.14-7.07 (m, 3H), 6.72-6.67 (m, 2H), 3.71 (br. t, 4H, J=5.4 Hz), 2.39 (br. t, 4H, J=5.4 Hz).

Example 33

2-(1-Phenyl-cyclohexyl)-thiophene

Phenyl cyclohexene (50 mg) and thiophene (100 mg) were dissolved in 33% HBr in acetic acid (0.5 mL). The mixture was stirred at room temperature over night. Tlc indicated full conversion of the starting material. Dichloromethane (10 mL) was added. The organic phase was washed with saturated NaHCO$_3$ (3×10 mL), dried Na$_2$SO$_4$ and concentrated in vacuo. The desired product was afforded after flash chromatography (eluent: dichloromethane). Yield: 39 mg. LC/MS purity (UV/MS): 100/90%, R$_t$ 6.22 min. M+1: 243

$^1$H NMR (400 MHz, CD$_3$Cl): 7.29-7.17 (m, 4H), 7.12-7.07 (m, 1H), 7.06 (dd, 1H, J=5.0 Hz, J=1.0 Hz), 6.83 (dd, 1H, J=5.0 Hz, J=3.5 Hz, 1H), 6.71 (dd, J=3.5 Hz, J=1.0 Hz, 1H), 2.35-2.24 (m, 4H), 1.62-1.35 (m, 6H).

Example 34

4-(1-Pyridin-3-yl-cyclohexyl)-phenol

The pyridine-boronic acid (1 g, 8.1 mmol), 1-cyclohexenyl-1-trifluoromethanesulfonate the triflate (2 g, 8.1 mmol) (TLC indicated that the triflate was partly decomposed (estimated purity 30%)) and potassium fluoride (200 mg) were suspended in dioxane. Argon was bubbled through the mixture. The palladium catalyst (50 mg) was added and the reaction mixture was stirred at 100° C. for 20 h. The mixture was stirred at 100° C. for 1 day. Dichloromethane (20 mL) and aqueous HCl (1 n, 20 mL) were added. The organic phase was separated off. The aqueous phase was neutralised with saturated NaHCO$_3$ (pH 7-8) and extracted with dichloromethane (2×30 mL). The combined organic phase was dried (Na$_2$SO$_4$) and concentrated in vacuo. The desired product was obtained after purification with flash chromatography. Yield: 150 mg syrup.

The syrup (75 mg) was dissolved in phenol (200 mg). Triflic acid (1 drop) was added. Stirred at 80° C. over night. The desired product was afforded after purification by flash chromatography. Yield: 25 mg. LC/MS purity (UV/MS): 100/100%, R$_t$ 3.20 min. M+1: 254

$^1$H NMR (400 MHz, CD$_3$Cl): 8.49 (d, J=2.2 Hz, 1H), 8.36 (dd, J=4.9 Hz, J=1.5 Hz, 1H), 7.62 (ddd, 1H, J=8.0 Hz, J=2.2 Hz, J=1.5 Hz), 7.24 (dd, 1H, J=8.0 Hz, J=4.9 Hz, 1H), 7.10-7.06 (m, 2H), 6.76-6.72 (m, 2H), 2.33-2.16 (m, 4H), 1.64-1.46 (m, 6H).

Example 35

1-(4-Hydroxy-phenyl)-cyclohexanecarbonitrile 1-(4-Methoxyphenyl)-1-cyclohexanexanecarbonitrile (100 mg, 0.46 mmol) was dissolved in dichloromethane (5 mL) and a solution of boron tribromide in dichloromethane (1M; 0.5 mmol, 0.5 mL) was added dropwise. Stirred at room temperature for 1 h, concentrated. $^1$H nmr the reaction had proceeded 20%. The syrup was dissolved in dichloromethane and a solution of boron tribromide in dichloromethane (1 mL, 1.0 mmol) was added. The solution was stirred for 24 h, concentrated and worked-up by flash chromatography. Yield: 82 mg. LC/MS purity (UV/MS): 100/90%, R$_t$ 6.0 min. M−1: 200

$^1$H NMR (400 MHz, CD$_3$Cl): 7.34-7.29 (m, 2H), 6.87-6.83 (m, 2H), 2.16-2.10 (m, 2H), 1.90-1.66 (m, 8H).

Example 36

Thiophene-3-yl cyclohexene

3-Thiophene boronic acid (128 mg, 1.00 mmol), cyclohexenyl triflate (230.2 mg, 1.00 mmol) was dissolved in $Et_2O$ (4 mL) and 2M $Na_2CO_3$ (1 mL). The mixture was degassed and $Pd(PPh_3)_4$ (0.05 mmol) added. After stirring at room temperature for 4 h the mixture was filtered through celite, rinsed with $Et_2O$, dried ($Na_2SO_4$) and subjected to column chromatography (silica, pentane) to yield 150 mg of a volatile liquid. GC-MS: $M^+$=164.

$^1$H-NMR (400 MHz, $CDCl_3$): 7.26-7.23 (m, 2H), 7.09-7.07 (m, 1H), 6.19-6.17 (m, 1H), 2.43-2.38 (m, 2H), 2.22-2.18 (m, 2H), 1.81-1.75 (m, 2H), 1.69-1.63 (m, 2H). $^{13}$C-NMR (125 MHz, $CDCl_3$): 144.3, 132.1, 125.4, 124.9, 124.1, 118.0, 27.5, 25.8, 23.1, 22.5.

Example 37

1-(4-Hydroxyphenyl)-thiophene-3-yl cyclohexane

Thiophene-3-yl cyclohexene (72.3 mg, 0.44 mmol), and phenol (82.8 mg, 0.88 mmol) was mixed and gently heated until uniform and $BF_3*H_3PO_4$ (4 uL, 0.044 mmol) was added. The mixture was heated at 70° C. overnight and the dark residue was diluted with EtOAc, washed with sat. $NaHCO_3$, dried and concentrated. Column chromatography (silica, 0-20% EtOAc) gave a mixture of isomers and the desired product could be isolated by preparative TLC (DCM eluent). Yield: 3.7 mg, off-white/pale yellow solid. GC-MS: $M^+$=258.

$^1$H-NMR (400 MHz, $CDCl_3$): 7.20 (dd, J=5.08 Hz, 2.93 Hz, 1H), 7.13 (d, J=8.80 Hz, 2H), 6.92 (dd, J=2.93 Hz, 1.37 Hz, 1H), 6.87 (dd, J=5.08 Hz, 1.37 Hz, 1H), 6.74 (d, J=8.80 Hz, 2H), 2.21-2.17 (m, 4H), 1.57-1.44 (m, 6H).

Example 38

Receptor Selection and Amplification Technology Assay

The functional receptor assay, Receptor Selection and Amplification Technology (R-SAT™), was used with minor modifications from the procedure described in U.S. Pat. No. 5,707,798, which is hereby incorporated by reference in its entirety, to screen compounds for efficacy at the Estrogen receptors alpha and beta (ERα, ERβ). NIH3T3 cells were grown in roller bottles to 70-80% confluence. Cells were then transfected for 12-16 h with plasmid DNAs using Polyfect (Qiagen Inc.) as per the manufacturer's protocol. R-SAT assays were typically performed by transfecting 30 ug/bottle of receptor and 50 ug/bottle of β-galactosidase plasmid DNA. All receptor and helper constructs used were in mammalian expression vectors. Helpers are defined as signaling molecules that modulate both ligand-dependent and/or ligand-independent function of the ER receptors, typically co-activators and kinases. NIH3T3 cells were transfected for 12-16 h, then trypsinized and frozen in DMSO. Frozen cells were later thawed, plated at 10,000-40,000 cells per well of a 96 well plate containing 4-(1-Phenyl-cyclohexyl)-phenol. Cells were then grown in a humidified atmosphere with 5% ambient $CO_2$ for five days. Media was then removed from the plates and marker gene activity was measured by the addition of the β-galactosidase substrate o-nitrophenyl β-D-galactopyranoside (ONPG, in PBS with 5% NP-40). The resulting colorimetric reaction was measured in a spectrophotometric plate reader (Titertek Inc.) at 420 nM. All data were analyzed using the computer program XLFit (IDBSm).

These experiments provided a molecular profile, or fingerprint, for each agent tested at the human Estrogen receptors. As can be seen in Table 1 and FIG. 1, 4-(1-Phenyl-cyclohexyl)-phenol (ERB-002) selectively activates Estrogen beta receptor (ERβ) relative to the Estrogen alpha receptor (ERα).

TABLE 1

| Compound | $pEC_{50}$ ERα | % Efficacy ERα | $pEC_{50}$ ERβ | % Efficacy ERβ |
|---|---|---|---|---|
| ERB-002 | 5.5 | 50 | 7.2 | 85 |
| ERB-004 | 5.5 | 77 | 7.5 | 90 |
| ERB-005 | 5.4 | 48 | 7.2 | 63 |
| ERB-007 | 5.8 | 30 | 7.1 | 57 |
| ERB-009 | 5.4 | 100 | 7.2 | 138 |
| ERB-011 | <5.0 | 20 | 7.1 | 37 |
| ERB-012 | 6.2 | 69 | 6.9 | 41 |
| ERB-014 | 5.9 | 120 | 7.1 | 87 |
| ERB-017 | 6.6 | 80 | 8.2 | 46 |
| ERB-030 | 5.6 | 95 | 7.2 | 46 |
| ERB-031 | 5.6 | 124 | 6.1 | 62 |
| ERB-037 | 5.8 | 114 | 8.1 | 48 |
| ERB-043 | <5.0 | 13 | 7.0 | 25 |

Efficacy is relative to the reference ligand Estrone.

Example 39

CFA Induced Arthritis Rat Model Assay

Figure 2:
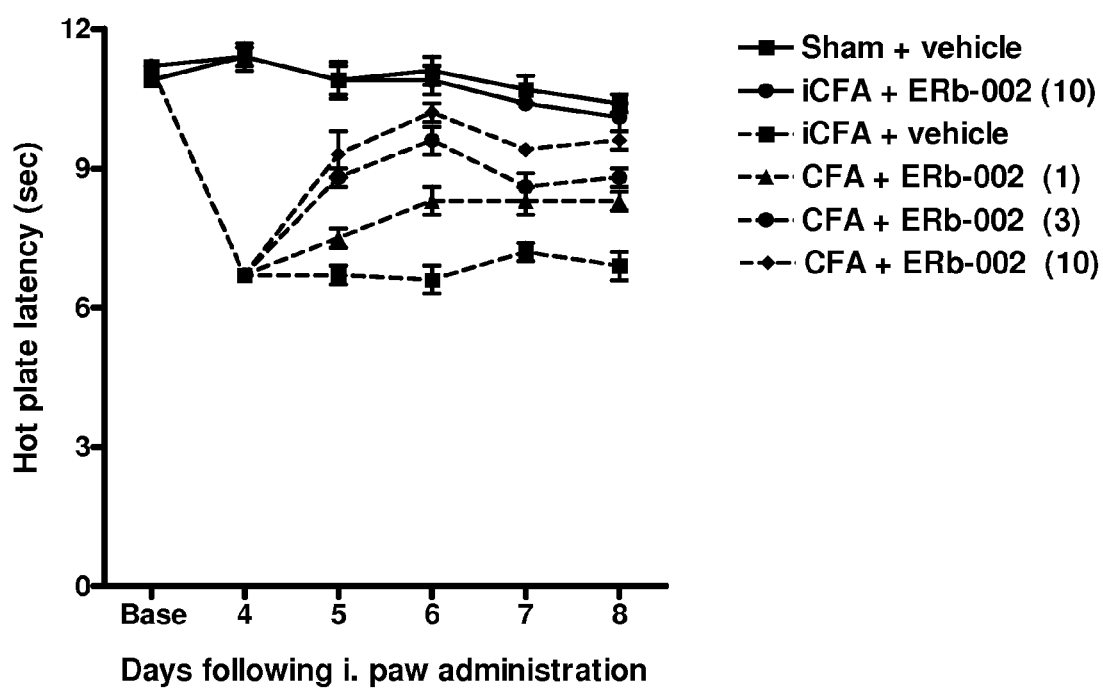
FIG. 2 is a graph depicting rat paw hot plate latency illustrating the reversal of thermal hyperalgesia by ERB-002.
Figure 3:
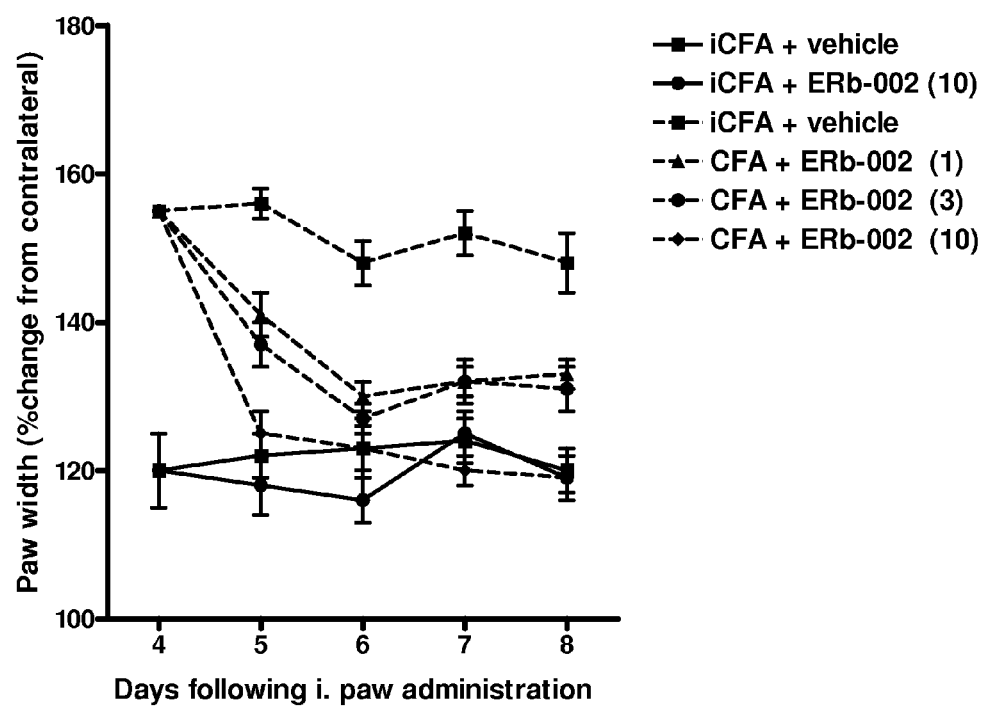
FIG. 3 is a graph depicting rat paw thickness illustrating the reversal of edema by ERB-002.

Naïve, male Sprague-Dawley rats (225-250 g; n=6 per group) served as subjects. Response latencies to a noxious thermal stimulus were measured using the 52° C. hot plate test. After obtaining baseline responses, 0.1 ml of Freund's complete adjuvant (CFA) or vehicle (inactivated CFA (iCFA)) was injected into the dorsal surface of the left hind paw. Response latencies were again measured 4 days following CFA (or iCFA) administration, a time point when thermal hyperalgesia is stable. A significant decrease in the hot plate latency was interpreted as the presence of thermal hyperalgesia. Following testing, thickness of both hind paws were measured (using a micrometer) in order to quantify possible edema formation at the injection site. Various doses of 4-(1-Phenyl-cyclohexyl)-phenol (ERB-002) (1.0, 3.0 or 10 mg/kg) or vehicle (DMSO) were administered (s.c.) following testing on Day 4, and then daily following testing for a period of 3 days. FIG. 2 illustrates the dose dependent reversal of thermal hyperalgesia in this model. FIG. 3 illustrates the dose dependent reversal of edema in this model.

Example 40

Uterotrophic In Vivo Assay

Figure 4:
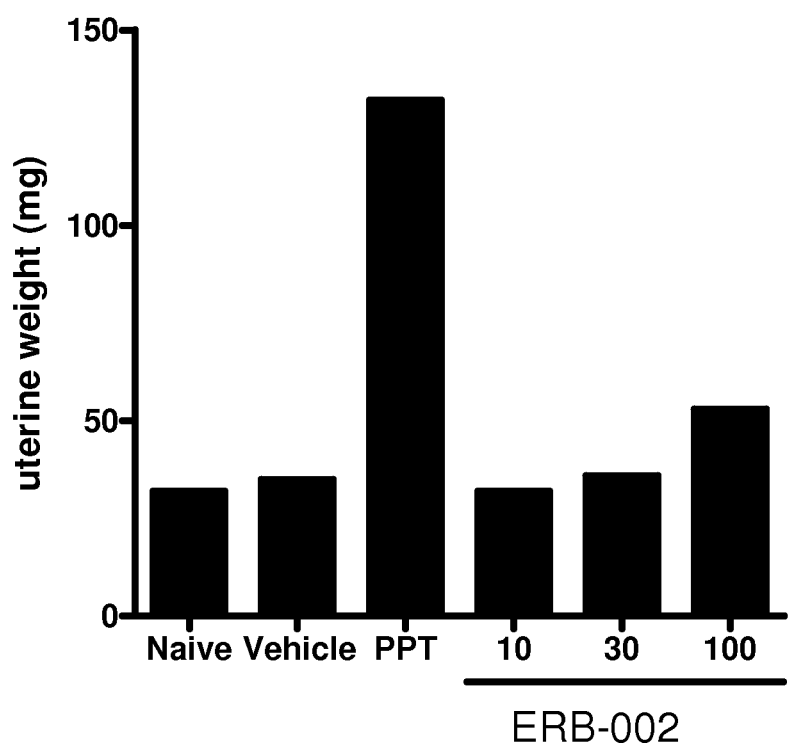
FIG. 4 is a bar graph depicting uterine weight illustrating that ERB-002 does not display uterotrophic properties in vivo in immature female rats.

The effect of ERB-002 on uterine weight was assessed based on the previously published method of Harris et al., Endocrin, 2003, 143:4172, which is hereby incorporated by reference in its entirety. Naïve, female Sprague-Dawley rats (30-40 g; n=6 per group) served as subjects. Rats received daily subcutaneous injections of vehicle (100% DMSO), PPT (1.0 mg/rat)), a reportedly selective ERa agonist (Stauffer, 2000, J Med Chem 43:4934) or various doses of ERB-002 (10, 30 or 100 mg/kg) for a total of 3 days. Approximately 24 hours after the final injection, the rats were sacrificed, the uteri removed, trimmed of adhesions, fluid expelled and then weighed. Uterine weight was normalized as a percentage of total body weight by the following formula: % TBW=[(uterus weight (in mg)/1000)/(body weight (in g))]*100. FIG. 4 illustrates that ERB-002 does not display uterotrophic properties in vivo in immature female rats.

What is claimed is:

1. A method of treating a disorder selected from the group consisting of Alzheimer's disease, Huntington's disease, Parkinson's disease, stroke; multiple sclerosis, acute or chronic pain, and symptoms associated therewith, the method comprising:
   identifying a subject in need of said treating; and
   administering to the subject a pharmaceutically effective amount of a compound of formula I:

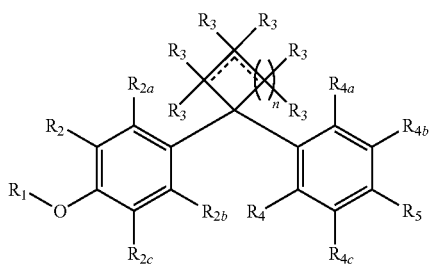

(I)

or a pharmaceutically acceptable salt or prodrug thereof, wherein:
   n is an integer selected from the group consisting of 3, 4, 5 and 6;
   $R_1$ is selected from the group consisting of hydrogen, $C_1$-$C_8$ straight chained or branched alkyl, $C_1$-$C_8$ straight chained or branched alkenyl, cycloalkyl, cycloalkenyl, substituted or unsubstituted aryl, and $C_1$-$C_8$ straight chained or branched perhaloalkyl;
   each of $R_2$, $R_{2a}$, $R_{2b}$, and $R_{2c}$ is separately selected from the group consisting of hydrogen, alkyl, alkenyl, cycloalkyl, cycloalkenyl, substituted or unsubstituted aryl, substituted or unsubstituted heteroaryl, substituted or unsubstituted heteroalicyclyl, hydroxy, halogen, sulfonyl, perhaloalkyl, —CN, —$OR_6$, —$NR_6R_{6a}$, —$NR_6NR_{6a}R_{6b}$, —$NR_6N$=$CR_{6a}R_{6b}$, —$N(R_6)C(R_{6a})$=$NR_{6b}$, —C(=Z)$R_6$, —C(=Z)$OR_6$, —C(=Z)$NR_6R_{6a}$, —N($R_6$)—C(=Z)$R_{6a}$, —N($R_6$)—C(=Z)$NR_{6b}R_{6a}$, —OC(=Z)$R_6$, —N($R_6$)—S (=O)$_2R_{6a}$, and —$SR_6$;
   $R_3$, located in one or more sites, is separately selected from the group consisting of hydrogen, alkyl, alkenyl, cycloalkyl, cycloalkenyl, substituted or unsubstituted aryl, substituted or unsubstituted heteroaryl, substituted or unsubstituted heteroalicyclyl, hydroxy, halogen, sulfonyl, perhaloalkyl, —CN, =O, and —$OR_6$, or is each separately absent to accommodate a double bond;
   two $R_3$ groups are optionally bound together to form a substituted or unsubstituted $C_3$-$C_9$ cycloalkyl or $C_3$-$C_9$ heteroalicyclyl;
   any bond represented by a dashed and solid line represents a bond selected from the group consisting of a single bond and a double bond;
   each of $R_4$, $R_{4a}$, $R_{4b}$, and $R_{4c}$ is separately selected from the group consisting of hydrogen, alkyl, alkenyl, cycloalkyl, cycloalkenyl, substituted or unsubstituted aryl, substituted or unsubstituted heteroaryl, substituted or unsubstituted heteroalicyclyl, hydroxy, halogen, nitro, sulfonyl, perhaloalkyl, —$OR_6$, —$NR_6R_{6a}$, —$NR_6NR_{6a}R_{6b}$, —$NR_6N$=$CR_{6a}R_{6b}$, —$N(R_6)C(R_{6a})$=$NR_{6b}$, —CN, —C(=Z)$R_6$, —C(=Z)$OR_6$, —C(=Z)$NR_6R_{6a}$, —S(=Z)$NR_6R_{6a}$, —N($R_6$)—C(=Z)$R_{6a}$, —N($R_6$)—C(=Z)$NR_{6b}R_{6a}$, —OC(=Z)$R_6$, —N($R_6$)—S (=O)$_2R_{6a}$, and —$SR_6$;
   $R_{4a}$ and $R_{4b}$ are optionally bound together to form an aryl, heteroaryl, or heteroalicyclyl;
   $R_5$ is selected from the group consisting of hydrogen, alkyl, alkenyl, cycloalkyl, cycloalkenyl, halogen, —CN, —$SR_6$, sulfonyl, —C(=O)$NR_6R_{6a}$, —C(=O)$R_6$, —$NR_6R_{6a}$, —$COOR_6$, —$OCF_3$, and perhaloalkyl;
   Z is oxygen or sulfur; and
   each of $R_6$, $R_{6a}$ and $R_{6b}$ is separately selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, and substituted or unsubstituted heteroalicyclyl;
   wherein when $R_1$ is hydrogen, and only one of $R_4$, $R_{4a}$, $R_{4b}$, $R_{4c}$, and $R_5$ is not hydrogen, then at least one of $R_2$, $R_{2a}$, $R_{2b}$, and $R_{2c}$ is not hydrogen, and
   wherein when $R_1$, $R_2$, $R_{2a}$, $R_{2b}$, and $R_{2c}$ are hydrogen, then at least two of $R_4$, $R_{4a}$, $R_{4b}$, $R_{4c}$, and $R_5$ are not hydrogen;
   provided that the compound is not selected from the group consisting of:

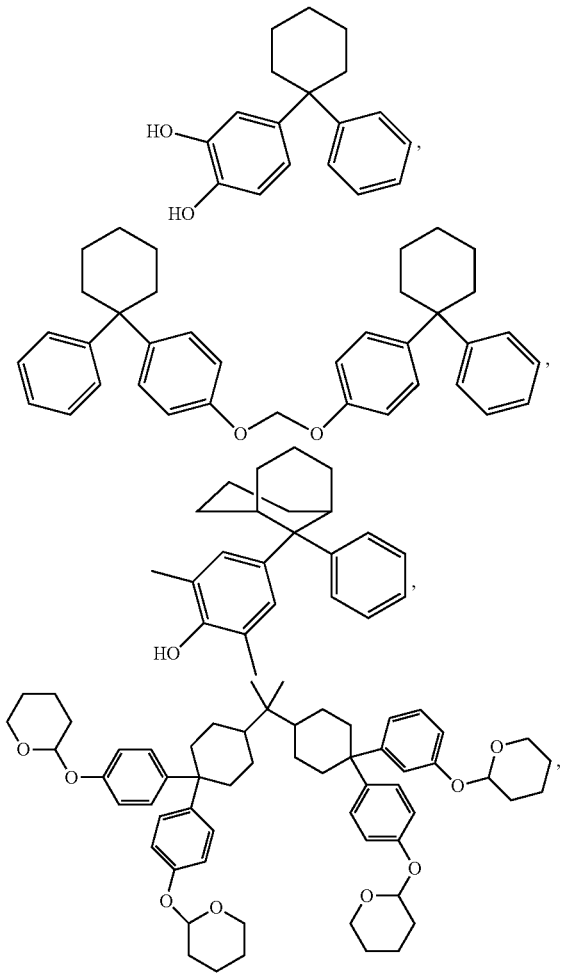

107
-continued
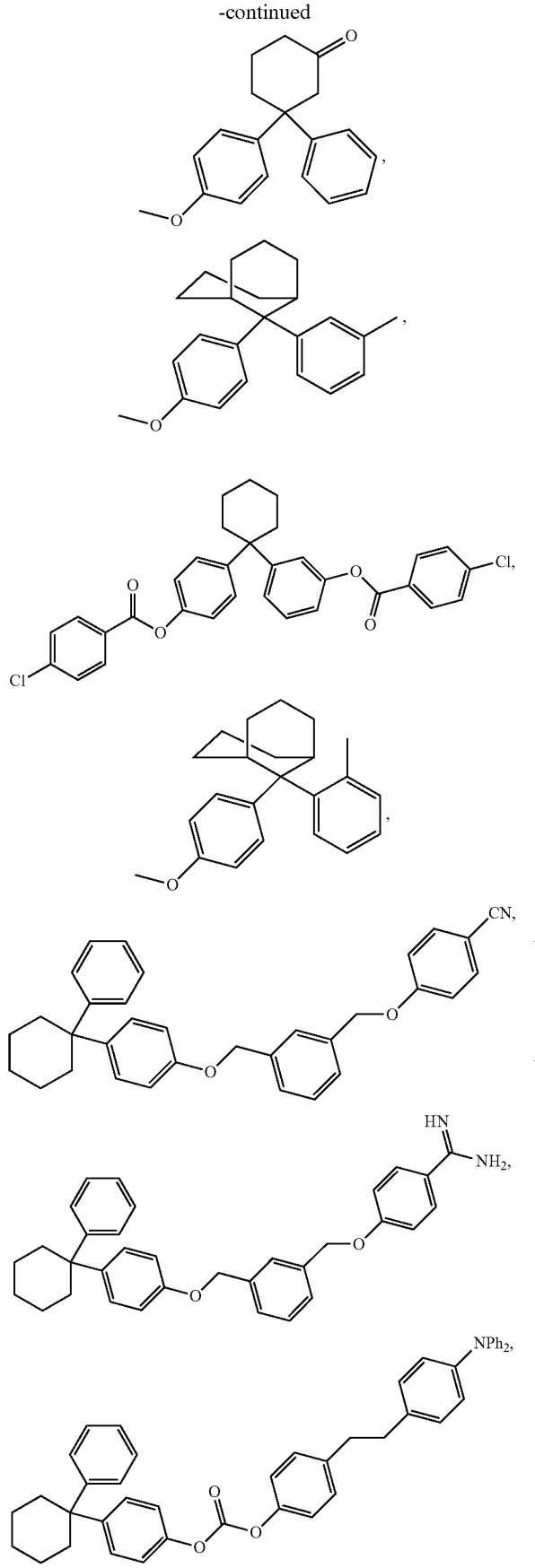
108
-continued
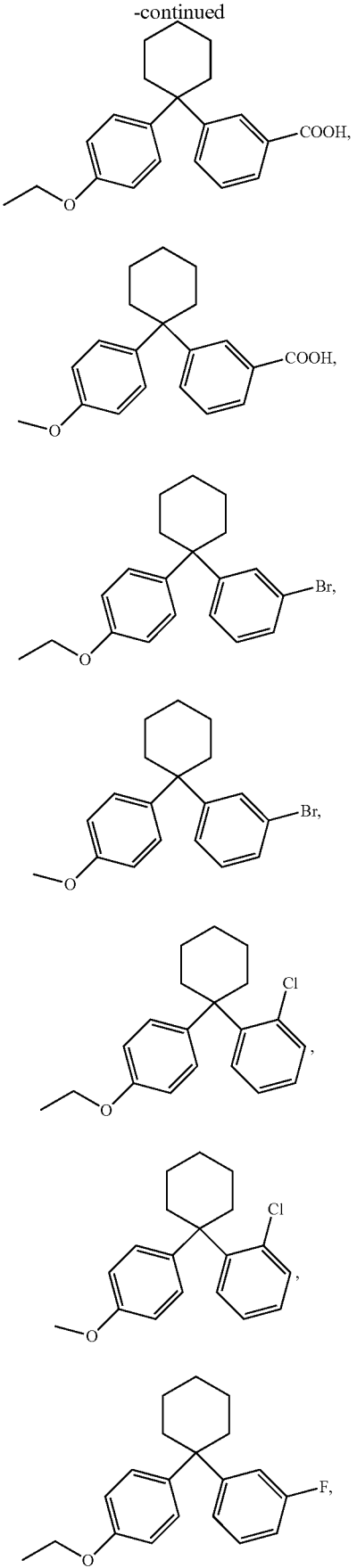

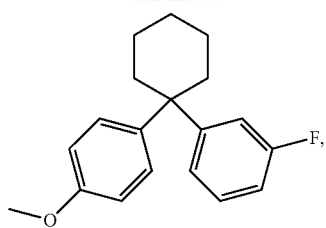
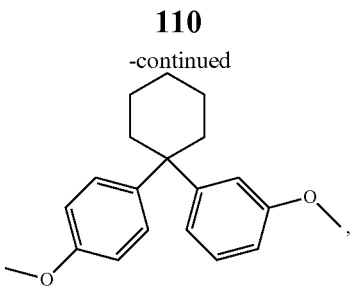
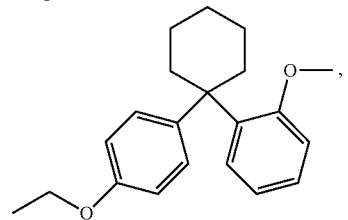
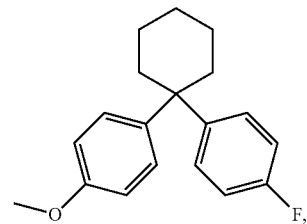
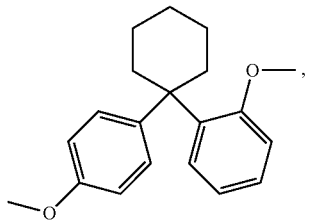
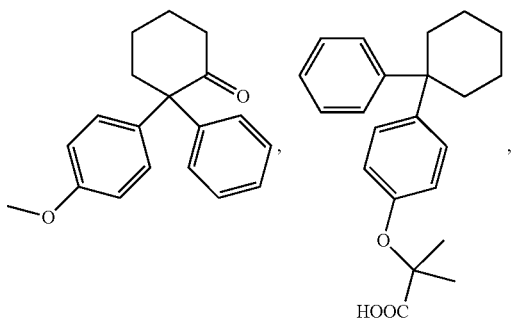
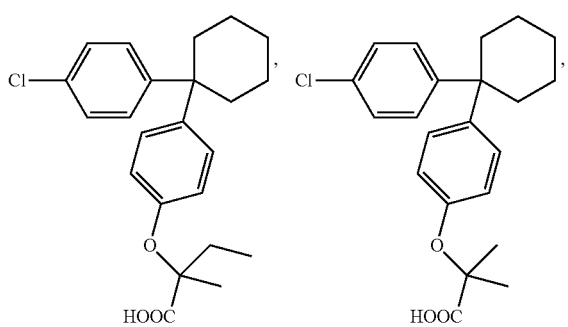
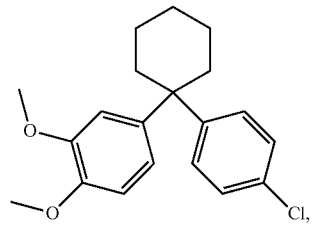
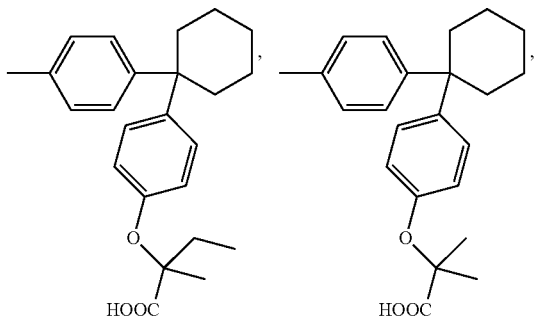
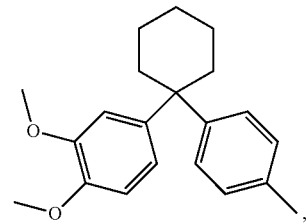
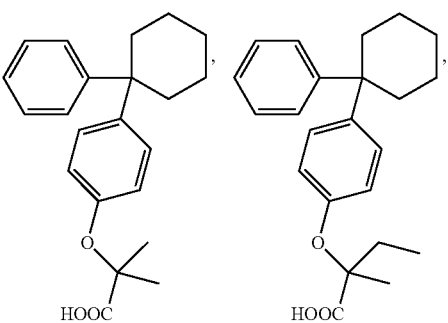
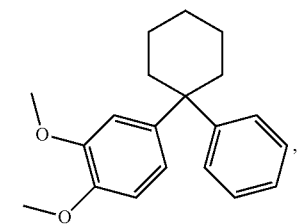

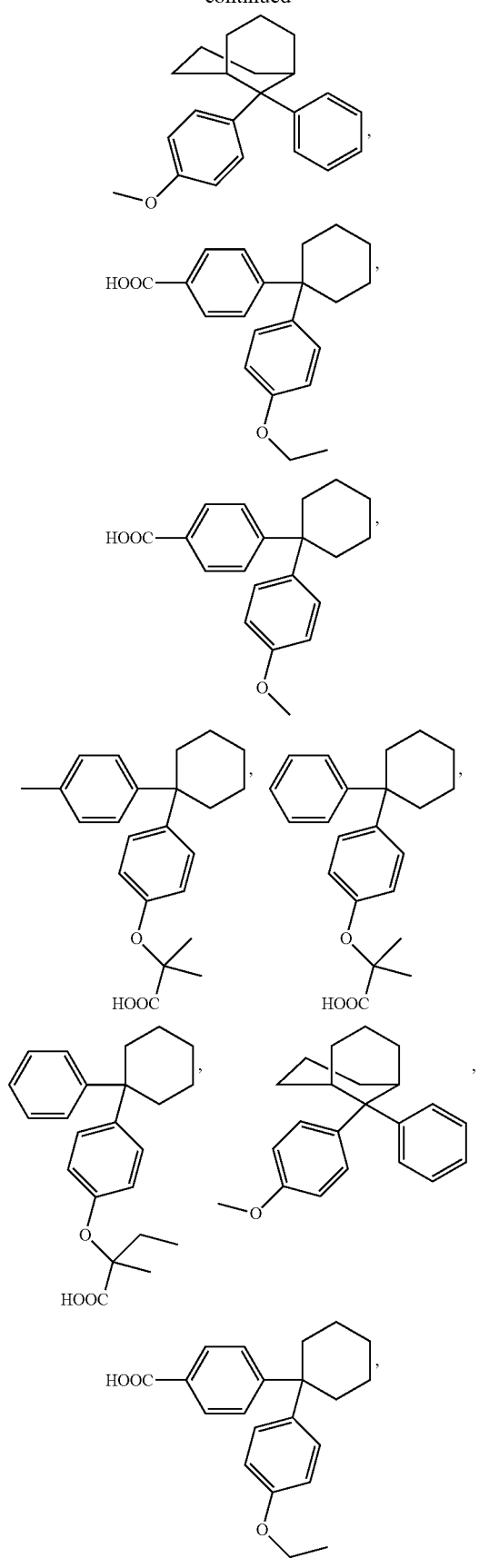

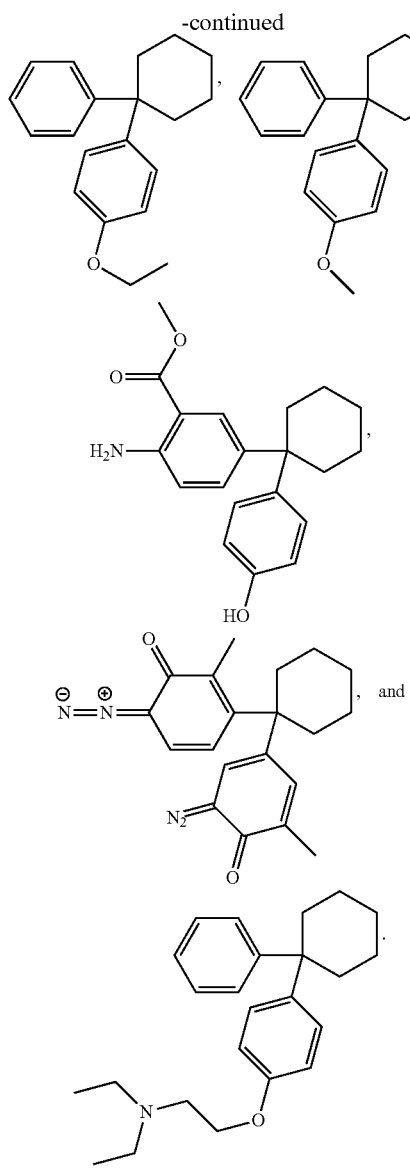

2. The method of claim 1, wherein;

n is an integer selected from the group consisting of 3, 4, and 5;

$R_1$ is selected from the group consisting of hydrogen, $C_1$-$C_4$ straight chained or branched alkyl, $C_1$-$C_4$ straight chained or branched alkenyl, $C_1$-$C_4$ straight chained or branched perhaloalkyl, and substituted or unsubstituted aryl;

each of $R_2$, $R_{2a}$, $R_{2b}$, and $R_{2c}$ is separately selected from the group consisting of hydrogen, $C_1$-$C_5$ straight chained or branched alkyl, $C_1$-$C_5$ alkenyl, hydroxy, halogen, sulfonyl, perhaloalkyl, —CN, —$OR_6$, —C(=O)$R_6$, —C(=O)$OR_6$, —C(=O)$NR_6R_{6a}$, —N($R_6$)—C(=O)$R_{6a}$, —N($R_6$)—S(=O)$_2R_{6a}$, —OC(=O)$R_6$, and —$SR_6$;

$R_3$, located in one or more sites, is separately selected from the group consisting of hydrogen, $C_1$-$C_5$ straight chained or branched alkyl, $C_1$-$C_5$ alkenyl, cycloalkyl, cycloalkenyl, hydroxy, halogen, sulfonyl, perhaloalkyl, —CN, =O, and —$OR_6$, or is each separately absent to accommodate a double bond;

each of $R_4$, $R_{4a}$, $R_{4b}$, and $R_{4c}$ is separately selected from the group consisting of hydrogen, $C_1$-$C_5$ straight chained or branched alkyl, $C_1$-$C_5$ alkenyl, hydroxy, halogen, sulfonyl, perhaloalkyl, —$OR_6$, —CN, —C(=O)$R_6$, —C(=O)$OR_6$, —C(=O)$NR_6R_{6a}$, —N($R_6$)—C(=O)$R_{6a}$, —OC(=Z)$R_6$, —N($R_6$)—S(=O)$_2R_{6a}$, and —$SR_6$; and $R_5$ is selected from the group consisting of hydrogen, $C_1$-$C_5$ straight chained or branched alkyl, halogen, —CN, —$SR_6$, sulfonyl, —$OCF_3$, and perhaloalkyl.

3. The method of claim 2 wherein;

n is 3;

$R_1$ is selected from the group consisting of hydrogen, $C_1$-$C_4$ straight chained or branched alkyl, substituted or unsubstituted aryl;

each of $R_2$, $R_{2a}$, $R_{2b}$, and $R_{2c}$ is separately selected from the group consisting of hydrogen, $C_1$-$C_5$ straight chained or branched alkyl, F, Cl, Br, perhaloalkyl, —CN,—$OR_6$, —C(=O), and —$SR_6$;

$R_3$, located in one or more sites, is separately selected from the group consisting of hydrogen, $C_1$-$C_5$ straight chained or branched alkyl, $C_1$-$C_5$ alkenyl, cycloalkyl, halogen, perhaloalkyl, —CN, and —$OR_6$, or is each separately absent to accommodate a double bond;

each of $R_4$, $R_{4a}$, $R_{4b}$, and $R_{4c}$ is separately selected from the group consisting of hydrogen, $C_1$-$C_5$ straight chained or branched alkyl, halogen, sulfonyl, perhaloalkyl, —$OR_6$, —CN, —N($R_6$)—S(=O)$_2R_{6a}$, and —$SR_6$; and $R_5$ is selected from the group consisting of hydrogen, $C_1$-$C_5$ straight chained or branched alkyl, F, Cl, —CN, —$SR_6$, —$OCF_3$, and $CF_3$.

4. The method of claim 2, wherein the compound of formula I is selected from the group consisting of:

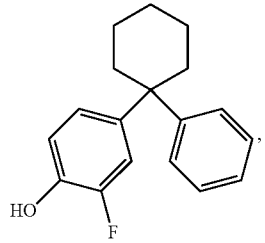

ERB-006

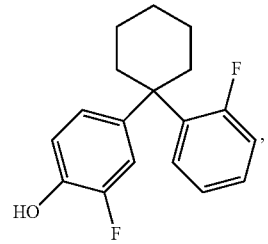

ERB-007

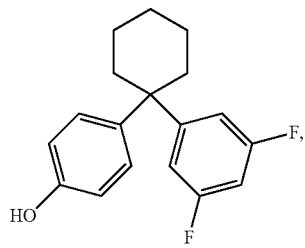

ERB-008

ERB-009
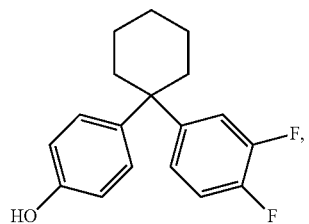
ERB-010
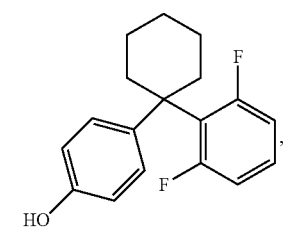
ERB-011
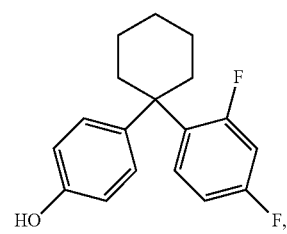
ERB-014
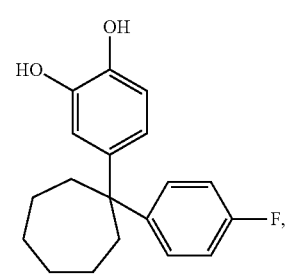
ERB-026
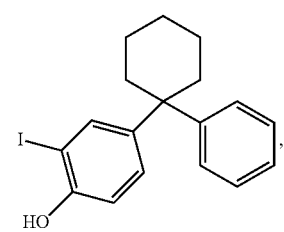
ERB-027
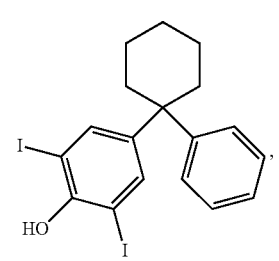
ERB-034
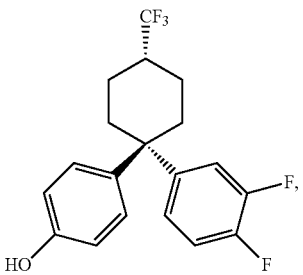
ERB-035
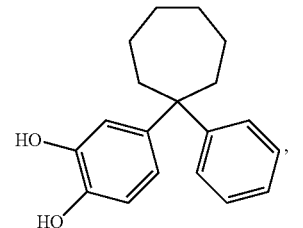
ERB-036
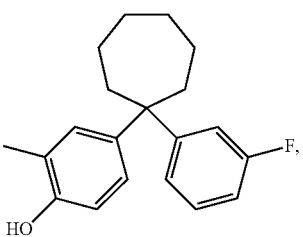
ERB-043
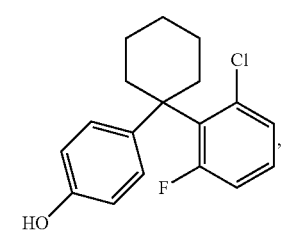
ERB-044
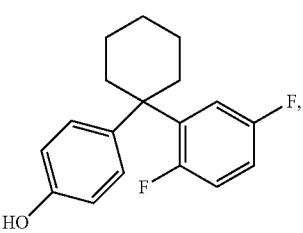
ERB-045
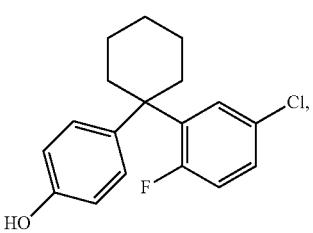
and a pharmaceutically acceptable salt or prodrug thereof.
5. The method of claim 1, wherein $R_1$ is selected from the group consisting of hydrogen, $C_1$-$C_8$ straight chained or branched alkyl, $C_1$-$C_8$ straight chained or branched alkenyl, and $C_1$-$C_8$ straight chained or branched perhaloalkyl.

6. The method of claim 1, wherein, $R_1$ is selected from the group consisting of hydrogen, cycloalkyl, cycloalkenyl, and substituted or unsubstituted aryl.

7. The method of claim 1, wherein each of $R_2$, $R_{2a}$, $R_{2b}$, and $R_{2c}$ is separately selected from the group consisting of hydrogen, alkyl, alkenyl, hydroxy, halogen, and perhaloalkyl.

8. The method of claim 1, wherein each of $R_2$, $R_{2a}$, $R_{2b}$, and $R_{2c}$ is separately selected from the group consisting of hydrogen, alkyl, hydroxy, halogen, cycloalkyl, cycloalkenyl, substituted or unsubstituted aryl, substituted or unsubstituted heteroaryl, and substituted or unsubstituted heteroalicyclyl.

9. The method of claim 1, wherein each of $R_2$, $R_{2a}$, $R_{2b}$, and $R_{2c}$ is separately selected from the group consisting of hydrogen, alkyl, hydroxy, and halogen, wherein the halogen is fluoro, chloro, or iodo.

10. The method of claim 1, wherein each of $R_2$, $R_{2a}$, $R_{2b}$, and $R_{2c}$ is separately selected from the group consisting of hydrogen, alkyl, hydroxy, and halogen, wherein the halogen is fluoro or iodo.

11. The method of claim 1, wherein each of $R_2$, $R_{2a}$, $R_{2b}$, and $R_{2c}$ is separately selected from the group consisting of hydrogen, alkyl, hydroxy, and halogen, wherein the alkyl is selected from the group consisting of methyl, ethyl, propyl, n-butyl, isobutyl, and tert-butyl.

12. The method of claim 1, wherein each of $R_2$, $R_{2a}$, $R_{2b}$, and $R_{2c}$ is separately selected from the group consisting of hydrogen, alkyl, hydroxy, and halogen, wherein the alkyl is methyl and wherein the halogen is fluoro or iodo.

13. The method of claim 1, wherein $R_3$, located in one or more sites, is separately selected from the group consisting of hydrogen, alkyl, alkenyl, and perhaloalkyl.

14. The method of claim 1, wherein $R_3$, located in one or more sites, is separately selected from the group consisting of hydrogen, isopropyl, and trifluoromethyl.

15. The method of claim 1, wherein each of $R_4$, $R_{4a}$, $R_{4b}$, $R_{4c}$ is separately selected from the group consisting of hydrogen, alkyl, hydroxy, halogen, and —$OR_6$.

16. The method of claim 1, wherein each of $R_4$, $R_{4a}$, $R_{4b}$, and $R_{4c}$ is separately selected from the group consisting of hydrogen, halogen, and —$OR_6$, wherein the halogen is chloro or fluoro, and wherein $R_6$ is hydrogen.

17. The method of claim 1, wherein $R_5$ is hydrogen or halogen, wherein the halogen is fluoro.

18. The method claim 1, wherein the compound of formula (I) is:

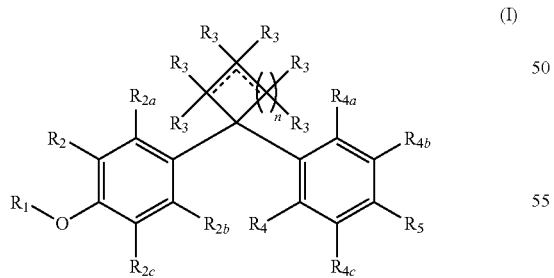

(I)

or a pharmaceutically acceptable salt or prodrug thereof, wherein:
n is 3;
$R_1$ is hydrogen;
$R_2$, $R_{2a}$, $R_{2b}$, and $R_{2c}$ is each separately hydrogen or fluoro;
$R_3$, located in one or more sites, is hydrogen;
each of $R_4$, $R_{4a}$, $R_{4b}$, and $R_{4c}$ is separately hydrogen or fluoro; and $R_5$ is hydrogen,
wherein when only one of $R_4$, $R_{4a}$, $R_{4b}$, and $R_{4c}$ is fluoro, then at least one of $R_2$, $R_{2a}$, $R_{2b}$, and $R_{2c}$ is fluoro, and
wherein when $R_2$, $R_{2a}$, $R_{2b}$, and $R_{2c}$ are hydrogen, then at least two of $R_4$, $R_{4a}$, $R_{4b}$, and $R_{4c}$ are fluoro.

19. The method of claim 1, wherein the compound of formula I is 2-Fluoro-4-(1-(2-fluorophenyl)cyclohexyl)phenol.

20. A method of hormonal replacement therapy in a subject, the method comprising:
identifying a subject in need thereof; and
administering to the subject a pharmaceutically effective amount of a compound of formula I:

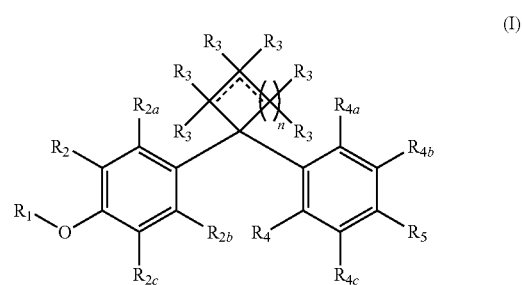

(I)

or a pharmaceutically acceptable salt or prodrug thereof, wherein:
n is an integer selected from the group consisting of 3, 4, 5 and 6;
$R_1$ is selected from the group consisting of hydrogen, $C_1$-$C_8$ straight chained or branched alkyl, $C_1$-$C_8$ straight chained or branched alkenyl, cycloalkyl, cycloalkenyl, substituted or unsubstituted aryl, and $C_1$-$C_8$ straight chained or branched perhaloalkyl;
each of $R_2$, $R_{2a}$, $R_{2b}$, and $R_{2c}$ is separately selected from the group consisting of hydrogen, alkyl, alkenyl, cycloalkyl, cycloalkenyl, substituted or unsubstituted aryl, substituted or unsubstituted heteroaryl, substituted or unsubstituted heteroalicyclyl, hydroxy, halogen, sulfonyl, perhaloalkyl, —CN, —$OR_6$, —$NR_6R_{6a}$, —$NR_6NR_{6a}R_{6b}$, —$NR_6N$=$CR_{6a}R_{6b}$, —$N(R_6)C(R_{6a})$=$NR_{6b}$, —$C$(=$Z$)$R_6$, —$C$(=$Z$)$OR_6$, —$C$(=$Z$)$NR_6R_{6a}$, —$N(R_6)$—$C$(=$Z$)$R_{6a}$, —$N(R_6)$—$C$(=$Z$)$NR_{6b}R_{6a}$, —$OC$(=$Z$)$R_6$, —$N(R_6)$—$S$(=$O$)$_2R_{6a}$, and —$SR_6$;
$R_3$, located in one or more sites, is separately selected from the group consisting of hydrogen, alkyl, alkenyl, cycloalkyl, cycloalkenyl, substituted or unsubstituted aryl, substituted or unsubstituted heteroaryl, substituted or unsubstituted heteroalicyclyl, hydroxy, halogen, sulfonyl, perhaloalkyl, —CN, =O, and —$OR_6$, or is each separately absent to accommodate a double bond;
two $R_3$ groups are optionally bound together to form a substituted or unsubstituted $C_3$-$C_9$ cycloalkyl or $C_3$-$C_9$ heteroalicyclyl;
any bond represented by a dashed and solid line represents a bond selected from the group consisting of a single bond and a double bond;
each of $R_4$, $R_{4a}$, $R_{4b}$, and $R_{4c}$ is separately selected from the group consisting of hydrogen, alkyl, alkenyl, cycloalkyl, cycloalkenyl, substituted or unsubstituted aryl, substituted or unsubstituted heteroaryl, substituted or unsubstituted heteroalicyclyl, hydroxy, nitro, halogen, sulfonyl, perhaloalkyl, —$OR_6$, —$NR_6R_{6a}$, —$NR_6NR_{6a}R_{6b}$, —$NR_6N$=$CR_{6a}R_{6b}$, —$N(R_6)C(R_{6a})$=$NR_{6b}$, —CN, —$C$(=$Z$)$R_6$, —$C$(=$Z$)$OR_6$, —$C$(=$Z$)$NR_6R_{6a}$, —S(=Z)NR$_6$R$_{6a}$, —N(R$_6$)—C(=Z)R$_{6a}$, —N(R$_6$)—C(=Z)NR$_{6b}$R$_{6a}$, —OC(=Z)R$_6$, —N(R$_6$)—S(=O)$_2$R$_{6a}$, and —SR$_6$;

R$_{4a}$ and R$_{4b}$ are optionally bound together to form an aryl, heteroaryl, or heteroalicyclyl;

R$_5$ is selected from the group consisting of hydrogen, alkyl, alkenyl, cycloalkyl, cycloalkenyl, halogen, —CN, —SR$_6$, sulfonyl, —C(=O)NR$_6$R$_{6a}$, —C(=O)R$_6$, —NR$_6$R$_{6a}$, —COOR$_6$, —OCF$_3$, and perhaloalkyl;

Z is oxygen or sulfur; and each of R$_6$, R$_{6a}$ and R$_{6b}$ is separately selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, and substituted or unsubstituted heteroalicyclyl;

wherein when R$_1$ is hydrogen, and only one of R$_4$, R$_{4a}$, R$_{4b}$, R$_{4c}$, and R$_5$ is not hydrogen, then at least one of R$_2$, $R_{2a}$, R$_{2b}$, and R$_{2c}$ is not hydrogen, and wherein when R$_1$, R$_2$, R$_{2a}$, R$_{2b}$, and R$_{2c}$ are hydrogen, then at least two of R$_4$, R$_{4a}$, R$_{4b}$, R$_{4c}$, and R$_5$ are not hydrogen;

provided that the compound is not selected from the group consisting of:

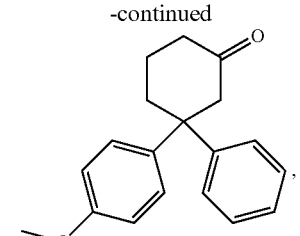

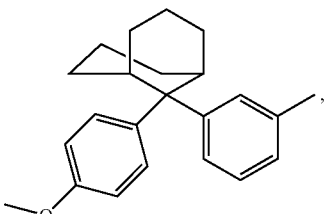

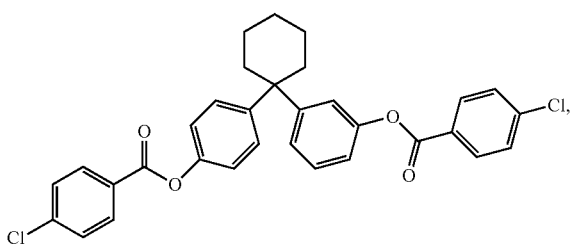

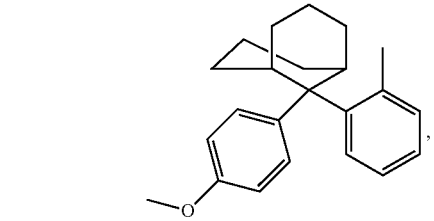

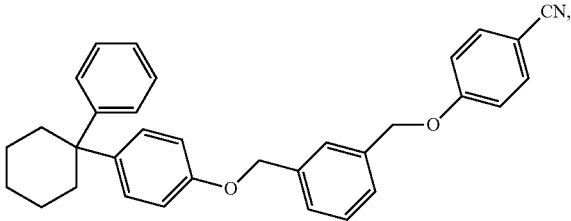

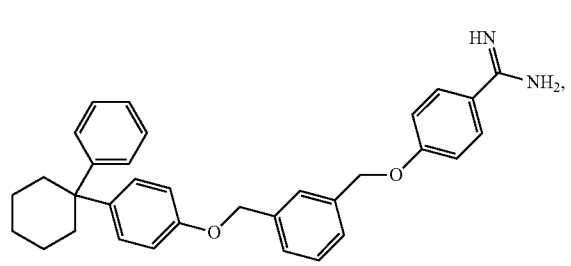

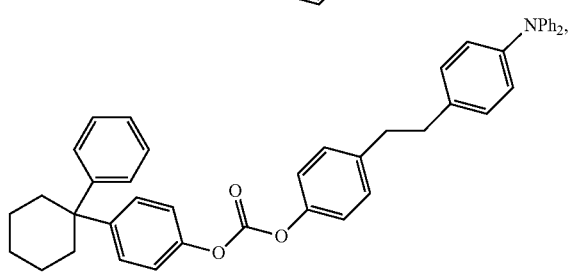

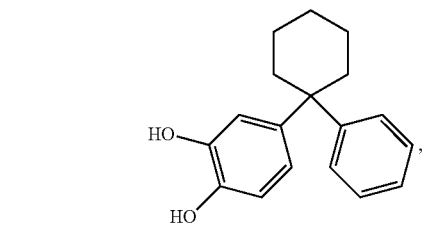

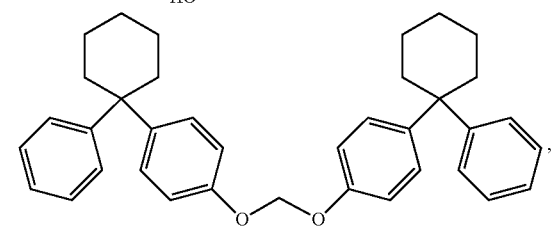

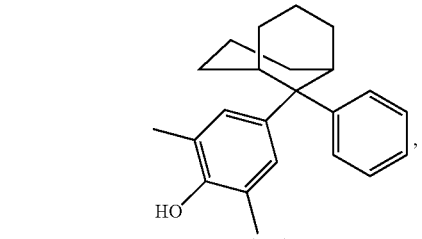

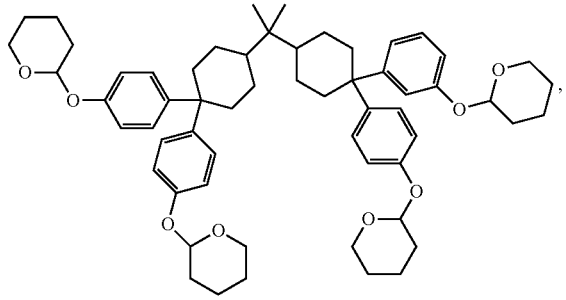

-continued
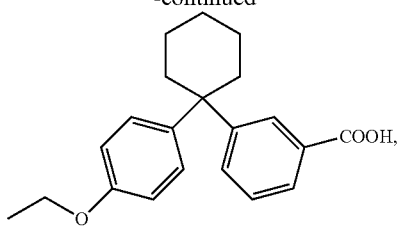
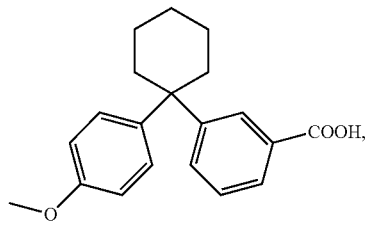
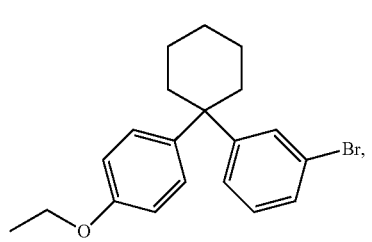
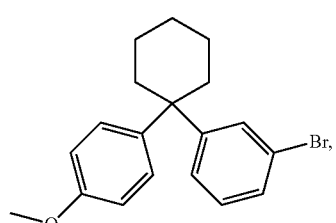
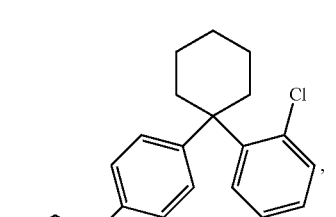
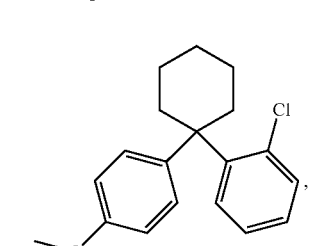
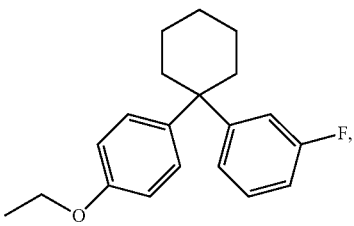
-continued
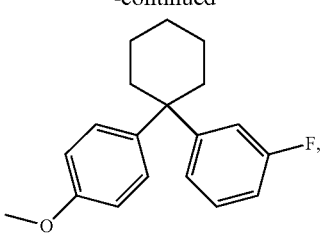
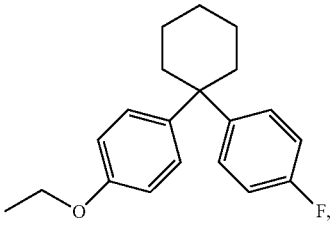
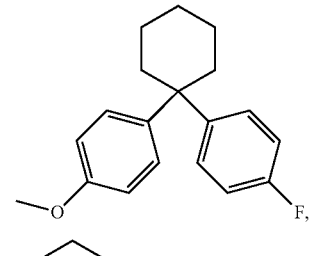
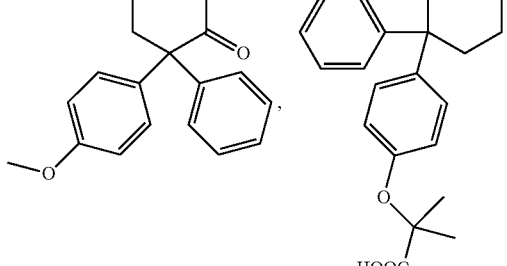
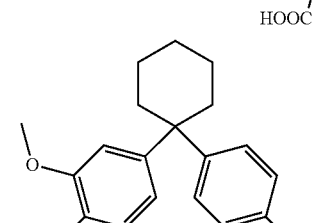
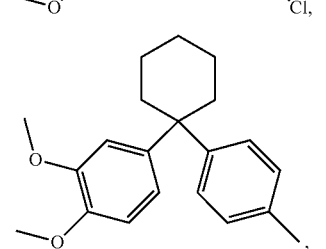
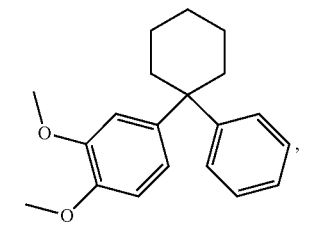

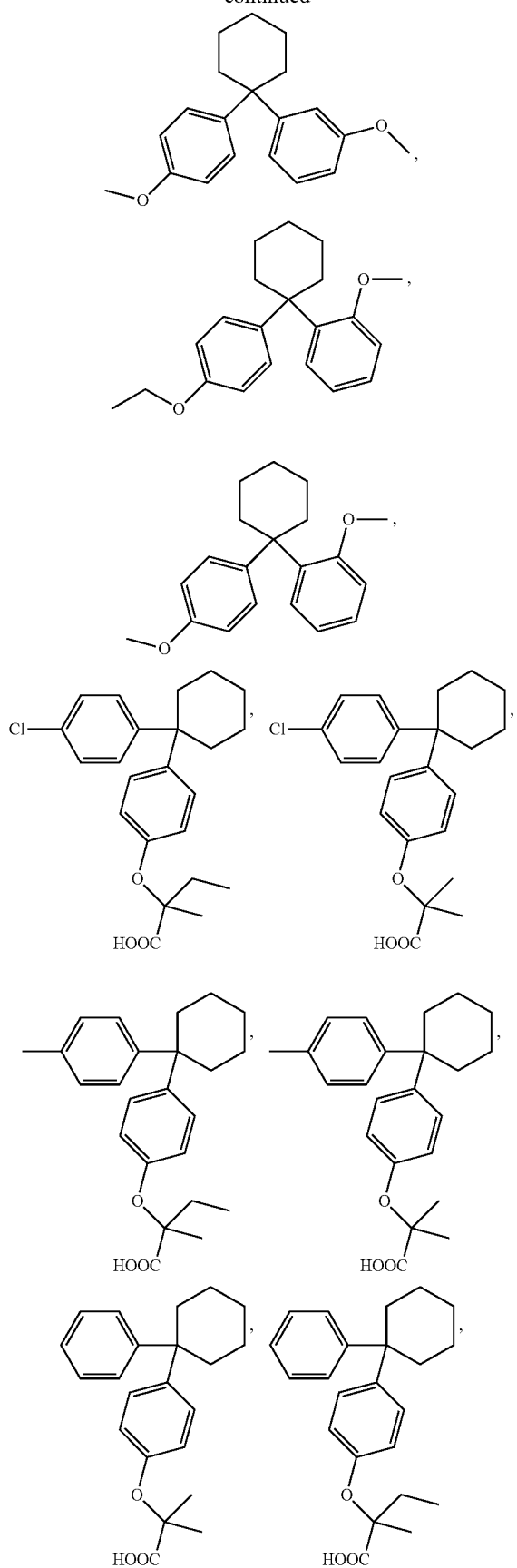
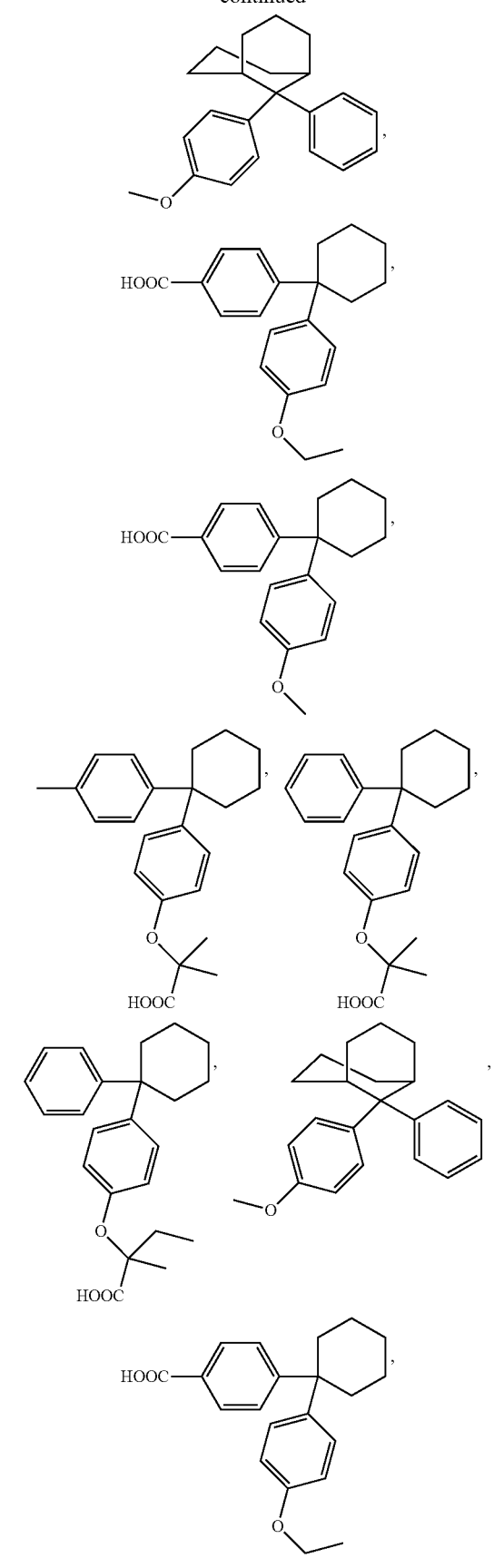

-continued
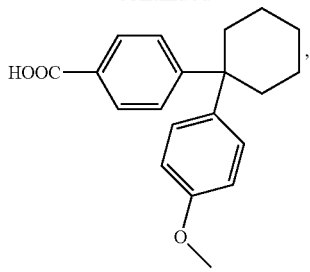
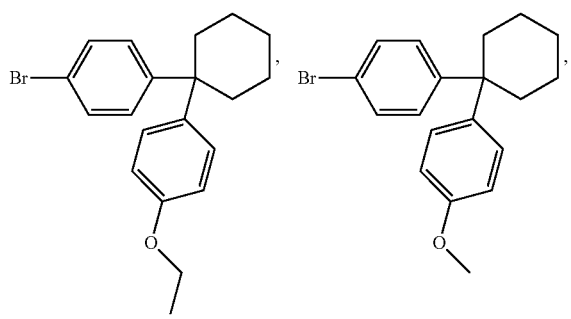
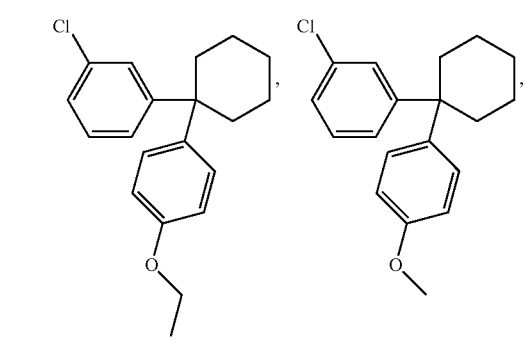
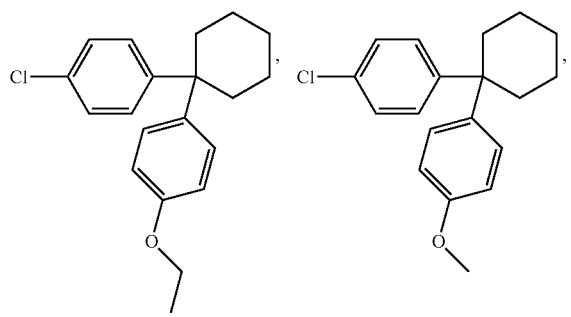
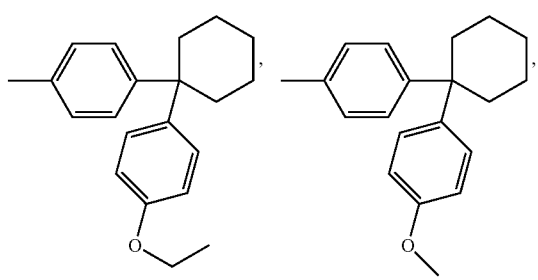
-continued
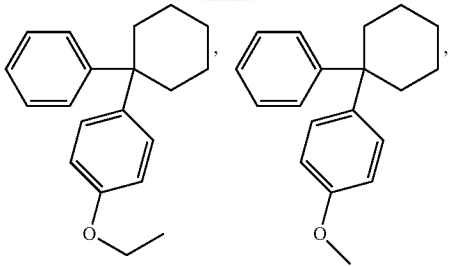
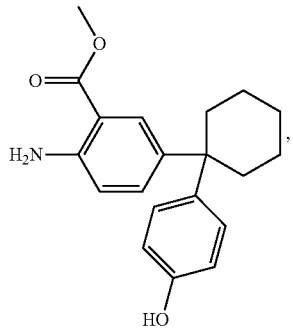
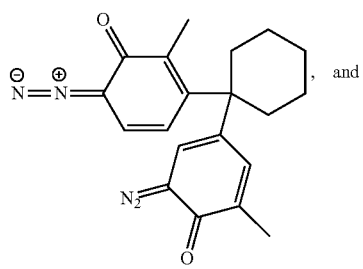
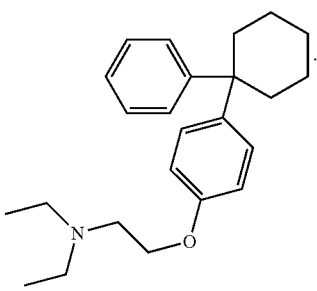
21. The method of claim 20, wherein the compound is selected from the group consisting of:
ERB-003
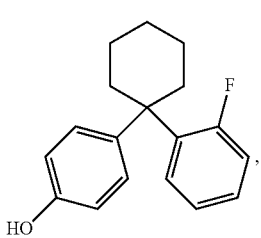

ERB-006 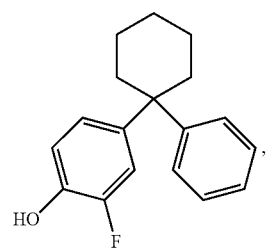
ERB-007 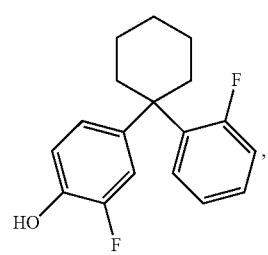
ERB-008 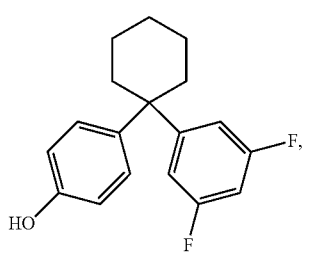
ERB-009 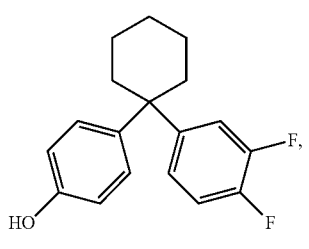
ERB-010 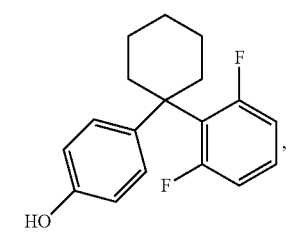
ERB-011 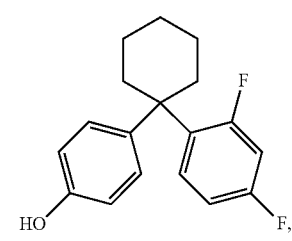
ERB-012 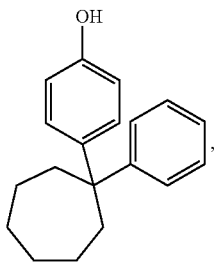
ERB-013 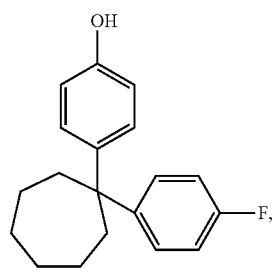
ERB-014 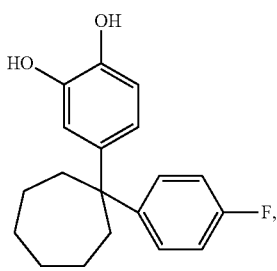
ERB-015 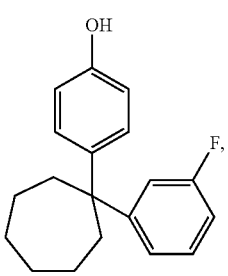
ERB-016 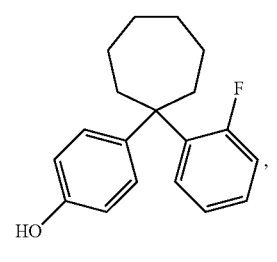
ERB-017 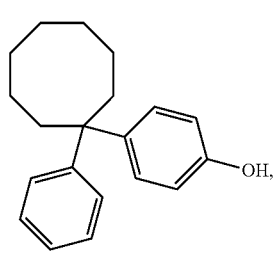

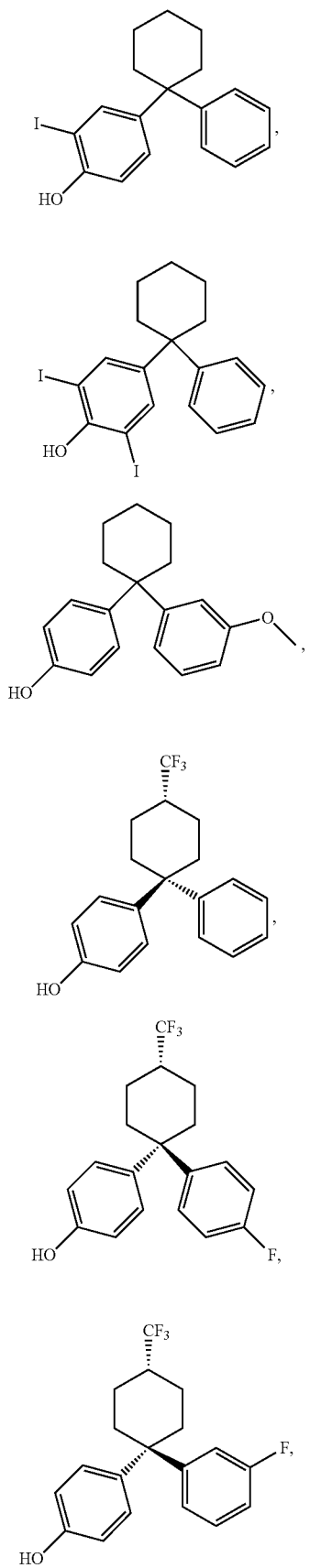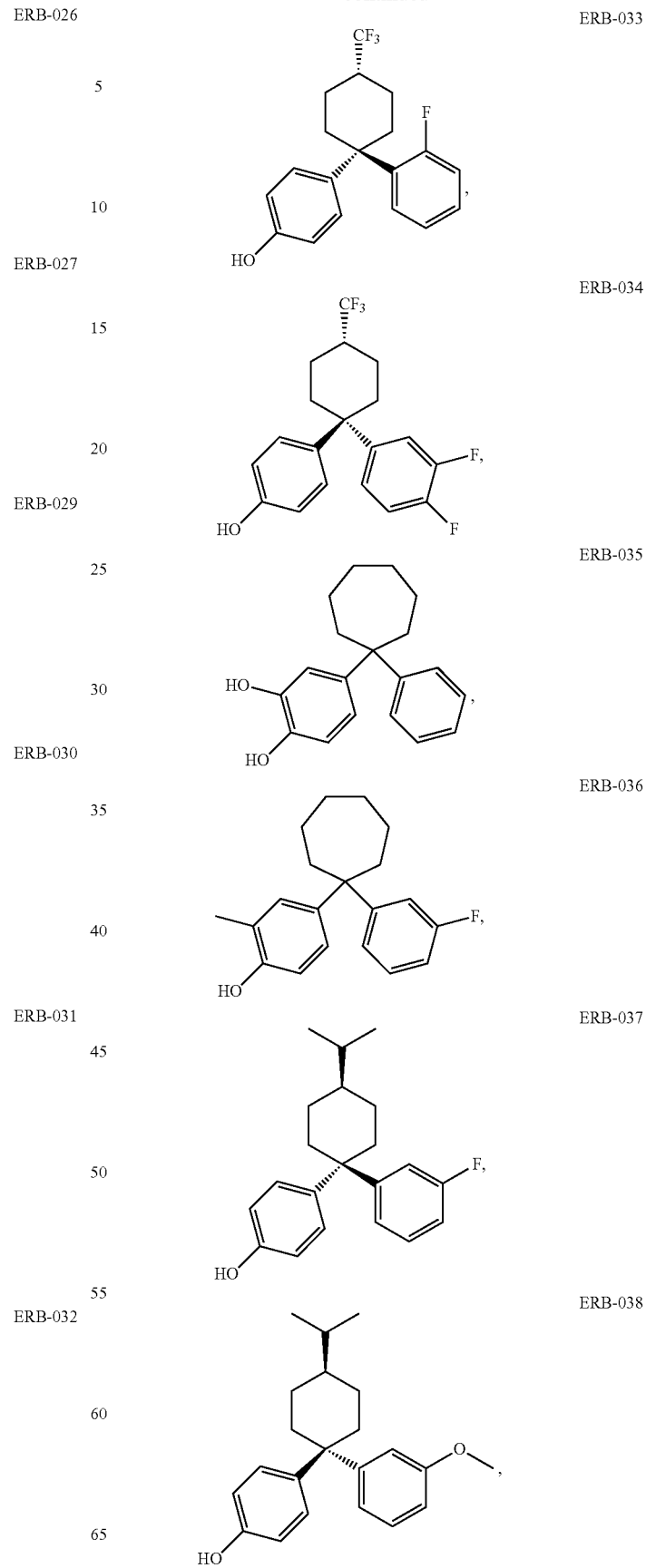

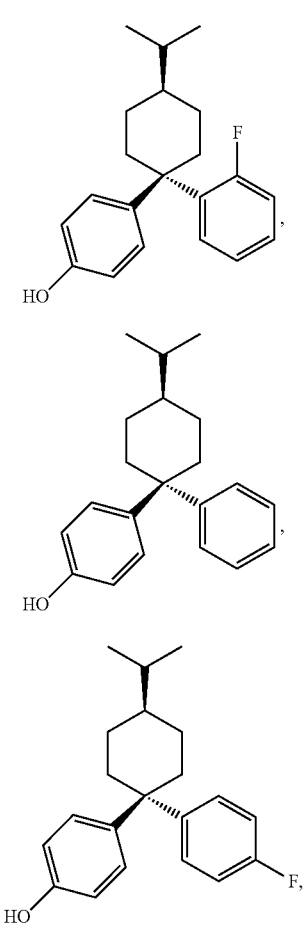
ERB-039
ERB-040
ERB-041
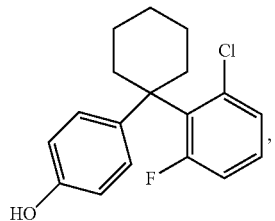
ERB-043
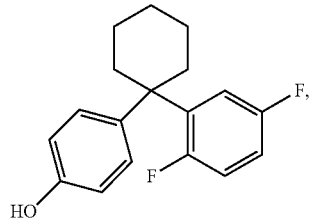
ERB-044
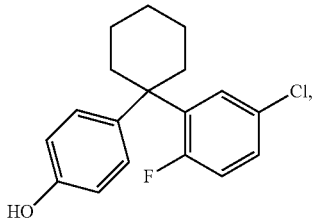
ERB-045
and a pharmaceutically acceptable salt or prodrug thereof.
* * * * *